(12) United States Patent
Masukawa et al.

(10) Patent No.: US 8,999,197 B2
(45) Date of Patent: *Apr. 7, 2015

(54) COMPOUND HAVING A FIVE-MEMBERED RING, THE LIQUID CRYSTAL COMPOSITION AND THE LIQUID CRYSTAL DISPLAY DEVICE

(71) Applicants: JNC Corporation, Tokyo (JP); JNC Petrochemical Corporation, Tokyo (JP)

(72) Inventors: Tokifumi Masukawa, Ichihara (JP); Yasuyuki Goto, Ichihara (JP); Tomohiro Yano, Ichihara (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/062,275

(22) Filed: Oct. 24, 2013

(65) Prior Publication Data

US 2014/0054499 A1 Feb. 27, 2014

Related U.S. Application Data

(63) Continuation of application No. 13/157,908, filed on Jun. 10, 2011, now Pat. No. 8,685,274.

(30) Foreign Application Priority Data

Jun. 18, 2010 (JP) ................................. 2010-139241

(51) Int. Cl.

| | |
|---|---|
| *C09K 19/34* | (2006.01) |
| *C09K 19/30* | (2006.01) |
| *C09K 19/52* | (2006.01) |
| *C09K 19/06* | (2006.01) |
| *C09K 19/00* | (2006.01) |
| *C07D 307/00* | (2006.01) |
| *C07C 43/02* | (2006.01) |
| *C07C 13/00* | (2006.01) |
| *C07C 43/18* | (2006.01) |
| *C07C 43/20* | (2006.01) |
| *C07D 307/10* | (2006.01) |
| *C07D 307/12* | (2006.01) |
| *C07D 307/20* | (2006.01) |
| *C09K 19/04* | (2006.01) |

(52) U.S. Cl.
CPC .......... *C09K 19/3066* (2013.01); *C07D 307/10* (2013.01); *C07D 307/12* (2013.01); *C07D 307/20* (2013.01); *C09K 19/30* (2013.01); *C09K 19/3405* (2013.01); *C09K 2019/0459* (2013.01); *C09K 2019/0466* (2013.01); *C09K 19/3003* (2013.01)

(58) Field of Classification Search
USPC .............. 428/1.1; 252/299.01, 299.6, 299.61, 252/299.63; 585/20; 568/642, 645, 647, 568/664; 549/429, 475, 497

See application file for complete search history.

(56) References Cited

U.S. PATENT DOCUMENTS

| | | |
|---|---|---|
| 4,873,019 A | 10/1989 | Krause |
| 5,384,070 A | 1/1995 | Hemmerling et al. |
| 5,759,443 A | 6/1998 | Funfschilling et al. |
| 8,685,274 B2 * | 4/2014 | Masukawa et al. ...... 252/299.61 |

FOREIGN PATENT DOCUMENTS

| | | |
|---|---|---|
| DE | 3739588 A1 | 7/1988 |
| GB | 2 220 658 A | 1/1990 |
| JP | 06-073041 A | 3/1994 |

OTHER PUBLICATIONS

Karamysheva, L.A., et al., 1991, Liquid-crystalline 1,4-disubstituted cycloheptanes, Liq. Cryst., 10, 875-879.
Karamysheva, L.A., et al., 1990, Liquid-crystalline 1,3-disubstituted cyclopentanes, Mol. Cryst. Liq. Cryst., 191, 237-246.
Karamysheva, L.A., et al., 1990, Cycloalkanoyl containing mesogens, Mol. Cryst. Liq. Cryst., 191, 247-252.
Crish, D. and Q. Yao, 1993, A New C-C Bond-forming Free Radical Rearrangement, Chem. Commun., (16), 1265-1267.

* cited by examiner

*Primary Examiner* — Geraldina Visconti
(74) *Attorney, Agent, or Firm* — Hogan Lovells US LLP

(57) ABSTRACT

The invention provides a liquid crystal compound that has an excellent compatibility with other liquid crystal compounds and also has at least one of characteristics such as a high stability to heat, light or the like, a suitable refractive index anisotropy ($\Delta n$), a low threshold voltage and a suitable dielectric anisotropy ($\Delta \varepsilon$). A compound represented by formula (1)

$$R^1-\left\langle\begin{array}{c}G\\\end{array}\right\rangle\!\!\left(\!Z^1\!-\!\!\left\langle A^1\right\rangle\!\right)_{\!m}\!\!\left(\!Z^2\!-\!\!\left\langle A^2\right\rangle\!\right)_{\!n}\!\!\left(\!Z^3\!-\!\!\left\langle A^3\right\rangle\!\right)_{\!p}\!\!-R^2 \quad (1)$$

For example, $R^1$ is alkyl having 1 to 10 carbons, $R^2$ is halogen or alkenyl having 2 to 10 carbons; the ring $A^1$, the ring $A^2$ and the ring $A^3$ are 1,4-cyclohexylene or 1,4-phenylene; $Z^1$, $Z^2$ and $Z^3$ are a single bond or alkylene having 1 to 4 carbons; G is —$CH_2$— or —O—; and m is 1, and n and p is 0 or 1.

15 Claims, No Drawings

COMPOUND HAVING A FIVE-MEMBERED RING, THE LIQUID CRYSTAL COMPOSITION AND THE LIQUID CRYSTAL DISPLAY DEVICE

This is a Continuation application of U.S. Non-Provisional application Ser. No. 13/157,908, filed Jun. 10, 2011, which claims priority to Japanese Patent Application No. 2010-139241, filed on Jun. 18, 2010, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

1. Field of the Invention

The invention relates to a new compound and a liquid crystal composition. More specifically, the invention relates to a liquid crystal compound having a five-membered ring, a liquid crystal composition including the compound and a liquid crystal display device containing the composition.

2. Related Art

A display device utilizing a liquid crystal compound has been widely used for the display of a clock, a calculator, a word processor or the like. The display device utilizes characteristics such as the refractive index anisotropy ($\Delta n$), the dielectric anisotropy ($\Delta \epsilon$) and so forth of the liquid crystal compound.

A liquid crystal phase includes a nematic liquid crystal phase, a smectic liquid crystal phase, a cholesteric liquid crystal phase, and the nematic phase is most widely applied. A display mode includes a DS (dynamic scattering) mode, a DAP (deformation of aligned phases) mode, a GH (guest-host) mode, a TN (twisted nematic) mode, a STN (super twisted nematic) mode, a TFT (a thin film transistor) mode, a VA (vertical alignment) mode, an IPS (in-plane switching) mode and a PSA (polymer sustained alignment) mode.

A liquid crystal compound used for these display modes is required to have a liquid crystal phase in a wide temperature range, centering at room temperature, a sufficient stability under conditions that the display device is used, and also sufficient characteristics for driving the display device. However, no single liquid crystal compounds that satisfy these conditions have been found until now.

The actual situation is that a liquid crystal composition is prepared by mixing from several to several tens of liquid crystal compounds in order to satisfy the required characteristics. It is required that the liquid crystal composition is stable to moisture, light, heat and air, which are normally present under conditions that the display device is used, and to an electric field or electromagnetic radiation, and also is stable chemically to a compound that will be mixed. It is required that the liquid crystal composition has suitable values of a variety of physical properties such as refractive index anisotropy ($\Delta n$) and dielectric anisotropy ($\Delta \epsilon$), depending on the display mode or the shape of the display device. Furthermore, it is important that each component in the liquid crystal composition has an excellent solubility in each other.

In recent years, modes such as IPS, VA and OCB among the display modes have been receiving attention as a display mode capable of overcoming a narrow viewing angle of a liquid crystal display device, which is the greatest subject to be solved. In particular, a liquid crystal display device having the VA mode or the IPS mode among liquid crystal display devices having these modes has been studied earnestly, since it has an excellent responsivity in addition to a wide viewing angle, and is capable of providing a high-contrast display. The liquid crystal composition used in the liquid crystal display devices having these display modes is characterized by the negative dielectric anisotropy ($\Delta \epsilon$). It is known that a liquid crystal composition having a large negative dielectric anisotropy ($\Delta \epsilon$) can decrease the driving voltage of a liquid crystal display device containing the liquid crystal composition. For example, see the none-patent document No. 1. Accordingly, liquid crystal compounds as the components of the liquid crystal composition are also required to have a larger negative dielectric anisotropy ($\Delta \epsilon$).

A compound having a high maximum temperature of a nematic phase ($T_{NI}$) is expected in order to drive a liquid crystal display device in a wide temperature range.

In general, a liquid crystal compound has two or more ring structures. Almost all of the ring structures are six-membered rings such as a cyclohexane ring and a benzene ring. A liquid crystal compound having a five-membered ring such as a furan ring or a thiadiazole ring is also known, however, only a few examples have been reported on a liquid crystal compound having a cyclopentane ring or a tetrahydrofuran ring.

A liquid crystal compound having a cyclopentane ring where the dielectric anisotropy is small has been reported. See, for example, the patent document No. 1, the patent document No. 2, the non-patent document No. 1, the non-patent document No. 2 and the non-patent document No. 3. A liquid crystal compound having a small dielectric anisotropy is used to adjust physical properties such as viscosity, temperature range of a nematic phase, refractive index anisotropy or the like of the liquid crystal composition, and thus a compound having more excellent characteristics such as a property that further decreases the viscosity of the liquid crystal composition, for instance, is required.

A liquid crystal compound having a tetrahydrofuran ring where the dielectric anisotropy is small has been reported. See, for example, the patent document No. 3 and the non-patent document No. 4. The compound having a tetrahydrofuran ring is also required to have more excellent characteristics.

A compound having a cyano group at the terminal position is known as a liquid crystal compound having a cyclopentane ring or a tetrahydrofuran ring where the dielectric anisotropy is positive, and it is required that the compound can be utilized for a liquid crystal display having a TFT mode and have an excellent voltage holding ratio.

A compound having excellent characteristics is required, since a liquid crystal compound having negative dielectric anisotropy can be used for a VA mode-device or the like. However, a liquid crystal compound having a cyclopentane ring or a tetrahydrofuran ring where the dielectric anisotropy is negative is scarcely known.

3. REFERENCES

Patent Document

Patent document No. 1: DE 3,739,588 A.

Patent document No. 2: JP 1994-073041 A.

Patent document No. 3: DD 274,041 A.

Non-Patent Document

Non-patent document No. 1: Liq. Cryst., 10, 875 (1991).
Non-patent document No. 2: Mol. Cryst. Liq. Cryst., 191, 237 (1990).
Non-patent document No. 3: Mol. Cryst. Liq. Cryst., 191, 247 (1990).
Non-patent document No. 4: Chem. Commun., (16), 1265 (1993).

SUMMARY OF THE INVENTION

The invention concerns a compound represented by formula (1), and also concerns a liquid crystal composition including the compound and a liquid crystal display device containing the composition:

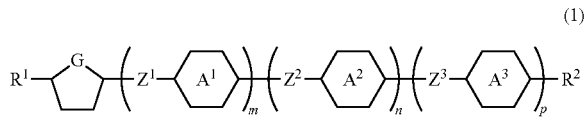

wherein
$R^1$ and $R^2$ are each independently halogen or alkyl having 1 to 10 carbons, and in the alkyl, arbitrary —$CH_2$— may be replaced by —O— and arbitrary —$(CH_2)_2$— may be replaced by —CH=CH—; the ring $A_1$, the ring $A^2$ and the ring $A^3$ are each independently 1,4-cyclohexylene or 1,4-phenylene, and in these rings, arbitrary hydrogen may be replaced by halogen, —$CF_3$ or —$OCF_3$;
$Z^1$, $Z^2$ and $Z^3$ are each independently a single bond or alkylene having 1 to 4 carbons, and in the alkylene, arbitrary —$CH_2$— may be replaced by —O— or —CO— and arbitrary —$(CH_2)_2$— may be replaced by —CH=CH—, and in these groups, arbitrary hydrogen may be replaced by halogen;
G is —$CH_2$— or —O—;
m, n and p are each independently 0 or 1, and the sum of m, n and p is 1, 2 or 3; and
$R^2$ is halogen or alkenyl having 2 to 10 carbons when the ring $A^1$, the ring $A^2$ and the ring $A^3$ are 1,4-cyclohexylene and/or 1,4-phenylene.

The first advantage of the invention is to provide a liquid crystal compound that has an excellent compatibility with other liquid crystal compounds and also has at least one of characteristics such as a high stability to heat, light or the like, a suitable refractive index anisotropy (Δn), a low threshold voltage and a suitable dielectric anisotropy (Δ∈).

The second advantage of the invention is to provide a liquid crystal composition that includes this compound, and has at least one of characteristics such as a small viscosity, a suitable refractive index anisotropy (Δn), a suitable dielectric anisotropy (Δ∈), a low threshold voltage, a high maximum temperature of a nematic phase (the phase transition temperature between a nematic phase and an isotropic phase) and a low minimum temperature of a nematic phase or is suitably balanced between at least two of the characteristics.

The third advantage of the invention is to provide a liquid crystal display device that contains this composition and has at least one of characteristics such as a short response time, small electric power consumption, a low driving voltage, a large contrast and a wide temperature range in which the device can be used, or is suitably balanced between at least two of the characteristics.

As a result of the research on the above subjects, it was found that a compound having a cyclopentane ring or a tetrahydrofuran ring had an excellent compatibility with other liquid crystal compounds. The result was utilized to solve the subject, and the invention has been completed.
The invention includes the following items 1 to 20.
Item 1. A compound represented by formula (1)

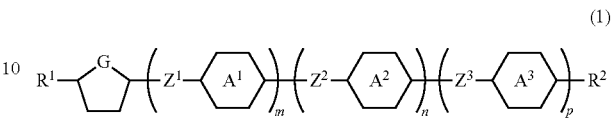

In formula (1),
$R^1$ and $R^2$ are each independently halogen or alkyl having 1 to 10 carbons, and in the alkyl, arbitrary —$CH_2$— may be replaced by —O— and arbitrary —$(CH_2)_2$— may be replaced by —CH=CH—;
the ring $A_1$, the ring $A^2$ and the ring $A^3$ are each independently 1,4-cyclohexylene or 1,4-phenylene, and in these rings, arbitrary hydrogen may be replaced by halogen, —$CF_3$ or —$OCF_3$;
$Z^1$, $Z^2$ and $Z^3$ are each independently a single bond or alkylene having 1 to 4 carbons, and in the alkylene, arbitrary —$CH_2$— may be replaced by —O— or —CO— and arbitrary —$(CH_2)_2$— may be replaced by —CH=CH—, and in these groups, arbitrary hydrogen may be replaced by halogen;
G is —$CH_2$— or —O—;
m, n and p are each independently 0 or 1, and the sum of m, n and p is 1, 2 or 3; and
$R^2$ is halogen or alkenyl having 2 to 10 carbons when the ring $A_1$, the ring $A^2$ and the ring $A^3$ are 1,4-cyclohexylene and/or 1,4-phenylene.
Item 2. The compound according to item 1, wherein in formula (1),
$R^1$ is alkyl having 1 to 10 carbons, alkoxy having 1 to 9 carbons or alkenyl having 2 to 10 carbons; $R^2$ is alkyl having 1 to 10 carbons, alkoxy having 1 to 9 carbons, alkenyl having 2 to 10 carbons, —$CF_3$, —$OCF_3$ or halogen;
the ring $A_1$, the ring $A^2$ and the ring $A^3$ are each independently 1,4-cyclohexylene, 1,4-cyclohexenylene, 1,4-phenylene, 2-fluoro-1,4-phenylene, 3-fluoro-1,4-phenylene, 2,3-difluoro-1,4-phenylene, 2,5-difluoro-1,4-phenylene or 3,5-difluoro-1,4-phenylene; and
$Z^1$, $Z^2$ and $Z^3$ are each independently a single bond, —$(CH_2)_2$—, —$(CH_2)_4$—, —COO—, —OCO—, —$CF_2O$—, —$OCF_2$—, —CH=CH—, —CF=CF—, —$CH_2O$— or —$OCH_2$—.
Item 3. The compound according to item 1 or 2, wherein in formula (1),
$R^1$ is alkyl having 1 to 7 carbons, alkoxy having 1 to 6 carbons or alkenyl having 2 to 7 carbons; $R^2$ is alkyl having 1 to 7 carbons, alkoxy having 1 to 6 carbons, alkenyl having 2 to 7 carbons, —$CF_3$, —$OCF_3$, fluorine or chlorine;
the ring $A_1$, the ring $A^2$ and the ring $A^3$ are each independently 1,4-cyclohexylene, 1,4-phenylene, 2-fluoro-1,4-phenylene, 3-fluoro-1,4-phenylene, 2,3-difluoro-1,4-phenylene or 3,5-difluoro-1,4-phenylene; and
$Z^1$, $Z^2$ and $Z^3$ are each independently a single bond, —$(CH_2)_2$—, —COO—, —OCO—, —$CF_2O$—, —$OCF_2$—, —$CH_2O$— or —$OCH_2$—.
Item 4. The compound according to any one of items 1 to 3, wherein in formula (1), G is —$CH_2$—.
Item 5. The compound according to any one of items 1 to 3, wherein in formula (1), G is —O—.
Item 6. The compound according to any one of items 1 to 5, wherein in formula (1), $R^2$ is alkenyl having 2 to 7 carbons;

the ring $A_1$, the ring $A^2$ and the ring $A^3$ are each independently 1,4-cyclohexylene or 1,4-phenylene.

Item 7. The compound according to any one of items 1 to 5, wherein in formula (1), $R^2$ is —$CF_3$, —$OCF_3$, fluorine or chlorine; the ring $A_1$, the ring $A^2$ and the ring $A^3$ are each independently 1,4-cyclohexylene, 1,4-phenylene, 3-fluoro-1,4-phenylene or 3,5-difluoro-1,4-phenylene.

Item 8. The compound according to any one of items 1 to 5, wherein in formula (1), $R^2$ is alkyl having 1 to 7 carbons, alkoxy having 1 to 6 carbons or alkenyl having 2 to 7 carbons; the ring $A^1$, the ring $A^2$ and the ring $A^3$ are each independently 1,4-cyclohexylene, 1,4-phenylene, 2-fluoro-1,4-phenylene, 3-fluoro-1,4-phenylene or 2,3-difluoro-1,4-phenylene, and at least one of the ring $A_1$, the ring $A^2$ and the ring $A^3$ is 2,3-difluoro-1,4-phenylene.

Item 9. A liquid crystal composition including a first component and a second component, wherein the first component is at least one compound selected from the compounds according to any one of items 1 to 8.

Item 10. The liquid crystal composition according to item 9, wherein the second component is at least one compound selected from the group of compounds represented by formulas (2), (3) and (4).

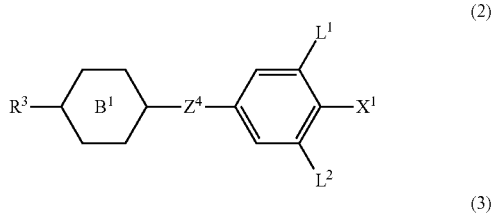

(2)

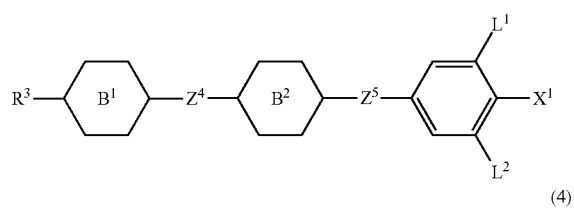

(3)

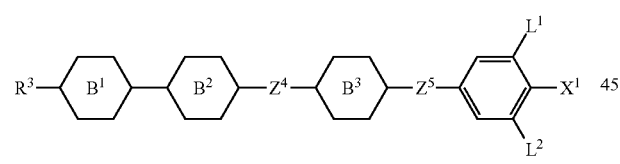

(4)

In formulas (2) to (4), $R^3$ is alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—;

$X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

the ring $B^1$, the ring $B^2$ and the ring $B^3$ are each independently 1,4-cyclohexylene, 1,3-dioxane-2,5-diyl, pyrimidine-2,5-diyl, 1-tetrahydropyran-2,5-diyl, or 1,4-phenylene in which arbitrary hydrogen may be replaced by fluorine;

$Z^4$ and $Z^5$ are each independently —$(CH_2)_2$—, —$(CH_2)_4$—, —COO—, —$CF_2O$—, —$OCF_2$—, —CH=CH—, —C≡C—, —$CH_2O$— or a single bond; and $L^1$ and $L^2$ are each independently hydrogen or fluorine.

Item 11. The liquid crystal composition according to item 9, wherein the second component is at least one compound selected from the group of compounds represented by formula (5).

(5)

$R^4$—C$^1$—(C$^2$)$_q$—$Z^6$—(C$^3$)$_r$—[phenyl with $L^3$, $L^4$]—$X^2$

In formula (5), $R^4$ is alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—;

$X^2$ is —C≡N or —C≡C—CN;

the ring $C^1$, the ring $C^2$ and the ring $C^3$ are each independently 1,4-cyclohexylene, 1,4-phenylene in which arbitrary hydrogen may be replaced by fluorine, 1,3-dioxane-2,5-diyl, 1-tetrahydropyran-2,5-diyl or pyrimidine-2,5-diyl;

$Z^6$ is —$(CH_2)_2$—, —COO—, —$CF_2O$—, —$OCF_2$—, —C≡C—, —$CH_2O$— or a single bond;

$L^3$ and $L^4$ are each independently hydrogen or fluorine; and q is 0, 1 or 2, and r is 0 or 1.

Item 12. The liquid crystal composition according to item 9, wherein the second component is at least one compound selected from the group of compounds represented by formulas (6), (7), (8), (9), (10) and (11).

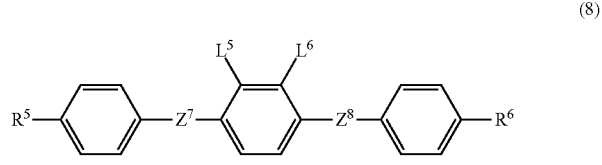

-continued

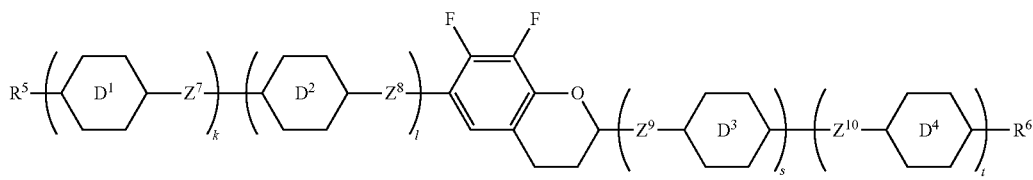
(10)

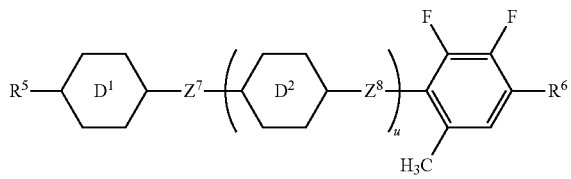
(11)

In formulas (6) to (11), $R^5$ and $R^6$ are each independently alkyl having 1 to 10 carbons or alkenyl having 2 to 10 carbons, in the alkyl and the alkenyl, arbitrary —$CH_2$— may be replaced by —O—, and in the alkenyl, arbitrary hydrogen may be replaced by fluorine;

the ring $D^1$, the ring $D^2$, the ring $D^3$ and the ring $D^4$ are each independently 1,4-cyclohexylene, 1,4-cyclohexenylene, 1,4-phenylene in which arbitrary hydrogen may be replaced by fluorine, tetrahydropyran-2,5-diyl or decahydro-2,6-naphthalene;

$Z^7$, $Z^8$, $Z^9$ and $Z^{10}$ are each independently -$(CH_2)_2$—, —COO—, —$CH_2O$—, —$OCF_2$—, —$OCF_2 (CH_2)_2$— or a single bond;

$L^5$ and $L^6$ are each independently fluorine or chlorine; and j, k, l, s, t and u are each independently 0 or 1, and the sum of k, l, s and t is 1 or 2.

Item 13. The liquid crystal composition according to item 9, wherein the second component is at least one compound selected from the group of compounds represented by formulas (12), (13) and (14).

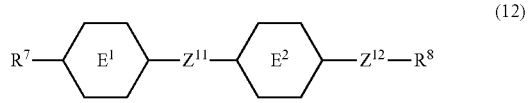
(12)

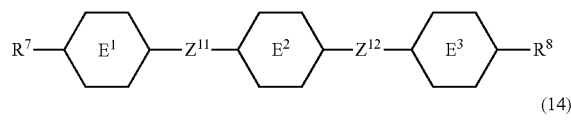
(13)

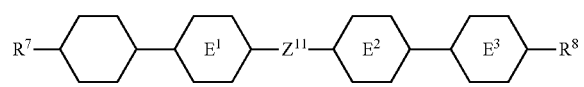
(14)

In formulas (12) to (14), $R^7$ and $R^8$ are each independently alkyl having 1 to 10 carbons or alkenyl having 2 to 10 carbons, and in the alkyl and the alkenyl, arbitrary —$CH_2$— may be replaced by —O—, and in the alkenyl, arbitrary hydrogen may be replaced by fluorine;

the ring $E^1$, the ring $E^2$ and the ring $E^3$ are each independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{11}$ and $Z^{12}$ are each independently —C≡C—, —COO—, —$(CH_2)_2$—, —CH=CH— or a single bond.

Item 14. The liquid crystal composition according to item 10, further including at least one compound selected from the group of compounds represented by formula (5) according to item 11.

Item 15. The liquid crystal composition according to item 10, further including at least one compound selected from the group of compounds represented by formulas (12), (13) and (14) according to item 13.

Item 16. The liquid crystal composition according to item 11, further including at least one compound selected from the group of compounds represented by formulas (12), (13) and (14) according to item 13.

Item 17. The liquid crystal composition according to item 12, further including at least one compound selected from the group of compounds represented by formulas (12), (13) and (14) according to item 13.

Item 18. The liquid crystal composition according to any one of items 9 to 17, further including at least one optically active compound and/or at least one polymerizable compound.

Item 19. The liquid crystal composition according to any one of items 9 to 18, wherein further including at least one antioxidant and/or at least one ultraviolet light absorber.

Item 20. A liquid crystal display device containing the liquid crystal composition according to any one of items 9 to 19.

Usage of the terms in this specification is as follows. A liquid crystal compound is a generic term for a compound having a liquid crystal phase such as a nematic phase or a smectic phase, and also for a compound having no liquid crystal phases but useful as a component for a liquid crystal composition. The terms, a liquid crystal compound, a liquid crystal composition and a liquid crystal display device may be abbreviated to a compound, a composition and a device, respectively. A liquid crystal display device is a generic term for a liquid crystal display panel and a liquid crystal display module. A maximum temperature of a nematic phase is the phase transition temperature between a nematic phase and an isotropic phase, and may simply be abbreviated to the clearing point or the maximum temperature. A minimum temperature of the nematic phase may simply be abbreviated to the minimum temperature. The compound represented by formula (1) may simply be abbreviated to the compound (1). This abbreviation may apply to the compound represented by formula (2) or the like. In formula (1) or the like, symbols such as A, B, $A^1$ and $B^1$ surrounded by a hexagonal shape correspond to the ring A, the ring B, the ring $A^1$ and the ring $B^1$, respectively. In the symbol such as the ring A, $R^1$, $Y^1$ or the like, two or more of the same symbol were described in the same or different formulas, and groups represented by arbitrary two symbols may be the same or different. The amount of a compound that is expressed as a percentage means a weight percentage (% by weight) based on the total weight of the composition.

"Arbitrary" means that "not only the position of an element such as hydrogen (or a group) but also its number can be selected without restriction." The expression "arbitrary A may be replaced by B, C or D" includes cases where arbitrary A is replaced by B, and arbitrary A is replaced by C, and arbitrary A is replaced by D, and also cases where a plurality of A are replaced by at least two of B, C and/or D. For example, the expression "alkyl in which arbitrary —$CH_2$— may be replaced by —O— or —CH=CH—" includes alkyl, alkenyl, alkoxy, alkoxyalkyl, alkoxyalkenyl and alkenyloxyalkyl. Incidentally, it is undesirable in the invention that two successive —$CH_2$— are replaced by —O— to give —O—O—. It is also undesirable that —$CH_2$— in the methyl moiety of alkyl is replaced by —O— to give —O—H.

The invention provides a liquid crystal compound that has an excellent compatibility with other liquid crystal compounds and also has at least one of characteristics such as a low threshold voltage, a high stability to heat, light or the like, a suitable refractive index anisotropy (Δn) and a suitable dielectric anisotropy (Δ∈). The invention provides a liquid crystal composition that has at least one of characteristics such as a small viscosity, a suitable refractive index anisotropy (Δn), a suitable negative dielectric anisotropy (Δ∈), a low threshold voltage and a low minimum temperature of a nematic phase. The invention also provides a liquid crystal display device that has at least one of characteristics such as a short response time, small electric power consumption, a low driving voltage, a large contrast and a wide temperature range in which the device can be used.

The invention will be more specifically explained below. The compound of the invention is represented by the following formula (1), namely the compound (1).

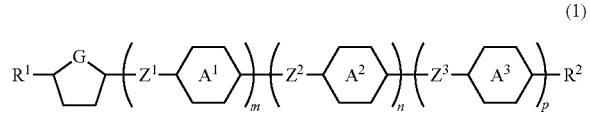

(1)

In formula (1), $R^1$ and $R^2$ are each independently alkyl having 1 to 10 carbons or halogen, and in the alkyl, arbitrary —$CH_2$— may be replaced by —O— and arbitrary —$(CH_2)_2$— may be replaced by —CH=CH—;

the ring $A_1$, the ring $A^2$ and the ring $A^3$ are each independently 1,4-cyclohexylene or 1,4-phenylene, and in these rings, arbitrary hydrogen may be replaced by halogen, —$CF_3$ or —$OCF_3$;

$Z^1$, $Z^2$ and $Z^3$ are each independently a single bond or alkylene having 1 to 4 carbons, and in the alkylene, arbitrary —$CH_2$— may be replaced by —O— or —CO—, and arbitrary —$(CH_2)_2$— may be replaced by —CH=CH—, and arbitrary hydrogen may be replaced by halogen;

G is —$CH_2$— or —O—;

m, n and p are each independently 0 or 1 and the sum of m, n and p is 1, 2 or 3; and $R^2$ is halogen or alkenyl having 2 to 10 carbons when the ring $A_1$, the ring $A^2$ and the ring $A^3$ are 1,4-cyclohexylene and/or 1,4-phenylene.

$R^1$ includes alkyl having 1 to 10 carbons, alkoxy having 1 to 9 carbons, alkoxyalkyl having 2 to 9 carbons, alkoxyalkoxy having 2 to 8 carbons, alkenyl having 2 to 10 carbons, alkenyloxy having 2 to 9 carbons, alkenyloxyalkyl having 3 to 9 carbons and alkoxyalkenyl having 3 to 9 carbons. A desirable alkyl chain in these groups is straight. When the alkyl chain is straight, the temperature range of liquid crystal phases is wide and the viscosity is small. It is desirable that the double bond in the alkenyl is in the odd positions and the configuration is trans. When the alkenyl has a plurality of double bonds, an unconjugated double bond is desirable.

The alkyl is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ and —$C_{10}H_{21}$;

the alkoxy is —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ and —$OC_9H_{19}$;

the alkoxyalkyl includes —$CH_2OCH_3$, —$CH_2OC_2H_5$, —$(CH_2)_2OCH_3$ and —$(CH_2)_2OC_2H_5$;

the alkoxyalkoxy includes —$OCH_2OCH_3$, —$OCH_2OC_2H_5$, —$O(CH_2)_2OCH_3$ and —$O(CH_2)_2OC_2H_5$;

the alkenyl includes —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$ and —$(CH_2)_2$CH=CH$(CH_2)_2$CH=$CH_2$;

the alkenyloxy includes —$OCH_2$CH=$CH_2$, —$OCH_2$CH=$CHCH_3$ and —$OCH_2$CH=$CHC_2H_5$;

the alkenyloxyalkyl includes —$CH_2OCH_2$CH=$CH_2$, —$CH_2OCH_2$CH=$CHCH_3$ and —$(CH_2)_2O(CH_2)_2$CH=$CH_3$; and the alkoxyalkenyl includes —CH=$CHCH_2OCH_3$, —CH=$CHCH_2OC_2H_5$ and —$CH_2$CH=$CHCH_2OCH_3$.

Desirable $R^1$ is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$OCH_3$, —$OC_2H_5$, —$OC_3H_7$, —$OC_4H_9$, —$OC_5H_{10}$, —$OC_6H_{13}$, —$OC_7H_{15}$, —$OC_8H_{17}$, —$OC_9H_{19}$, —CH=$CH_2$, —CH=$CHCH_3$, —CH=$CHC2H_5$, —$(CH_2)_2$CH=$CH_2$, —CH=$CHC3H_7$, —$(CH_2)_2$CH=$CHCH_3$, —$(CH_2)_3$CH=$CH_2$, —CH=CH$(CH_2)_2$CH=$CH_2$ and —$(CH_2)_2$CH=CH$(CH_2)_2$CH=$CH_2$.

More desirable $R^1$ is —$CH_3$, —$C_2H_5$, —$C_3H_7$, —$C_4H_9$, —$C_5H_{11}$, —$C_6H_{13}$, —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$ and —$(CH_2)_2$ CH=CH$(CH_2)_2$ CH=$CH_2$.

$R^2$ includes alkyl having 1 to 10 carbons, alkoxy having 1 to 9 carbons, alkoxyalkyl having 2 to 9 carbons, alkoxyalkoxy having 2 to 8 carbons, alkenyl having 2 to 10 carbons, alkenyloxy having 2 to 9 carbons, alkenyloxyalkyl having 3 to 9 carbons, alkoxyalkenyl having 3 to 9 carbons and halogen. A desirable alkyl chain in these groups is straight. When the alkyl chain is straight, the temperature range of liquid crystal phases is wide and the viscosity is small. It is desirable that the double bond in the alkenyl is in the odd positions and the configuration is trans. When the alkenyl has a plurality of double bonds, an unconjugated double bond is desirable.

The alkyl is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ and —$C_{10}H_{21}$;

the alkoxy is —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ and —$OC_9H_{19}$;

the alkoxyalkyl includes —$CH_2OCH_3$, —$CH_2OC_2H_5$, —$(CH_2)_2OCH_3$ and —$(CH_2)_2OC_2H_5$;

the alkoxyalkoxy —$OCH_2OCH_3$, —$OCH_2OC_2H_5$, —$O(CH_2)_2OCH_3$ and —$O(CH_2)_2OC_2H_5$;

the alkenyl includes —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —$(CH_2)_3$CH=$CH_2$, —CH=CH$(CH_2)_2$CH=$CH_2$ and —$(CH_2)_2$CH=CH$(CH_2)_2$CH=$CH_2$;

the alkenyloxy includes —OCH$_2$CH=CH$_2$, —OCH$_2$CH=CHCH$_3$ and —OCH$_2$CH=CHC$_2$H$_5$;

the alkenyloxyalkyl includes —CH$_2$OCH$_2$CH=CH$_2$, —CH$_2$OCH$_2$CH=CHCH$_3$ and —(CH$_2$)$_2$O(CH$_2$)$_2$CH=CH$_3$; and the alkoxyalkenyl includes —CH=CHCH$_2$OCH$_3$, —CH=CHCH$_2$OC$_2$H$_5$ and —CH$_2$CH=CHCH$_2$OCH$_3$; and The halogen includes fluorine, chlorine and bromine.

Desirable R$^2$ is —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —OCH$_3$, —OC$_2$H$_5$, —OC$_3$H$_7$, —OC$_4$H$_9$, —OC$_5$H$_{10}$, —OC$_6$H$_{13}$, —OC$_7$H$_{15}$, —OC$_8$H$_{17}$, —OC$_9$H$_{19}$, —CH=CH$_2$, —CH=CHCH$_3$, —CH=CHC$_2$H$_5$, —(CH$_2$)$_2$CH=CH$_2$, —CH=CHC$_3$H$_7$, —(CH$_2$)$_2$CH=CHCH$_3$, —(CH$_2$)$_3$CH=CH$_2$, —CH=CH(CH$_2$)$_2$CH=CH$_2$, —(CH$_2$)$_2$CH=CH(CH$_2$)$_2$CH=CH$_2$, fluorine and chlorine.

More desirable R$^2$ is —CH$_3$, —C$_2$H$_5$, —C$_3$H$_7$, —C$_4$H$_9$, —C$_5$H$_{11}$, —C$_6$H$_{13}$, —CH=CH$_2$, —CH=CHCH$_3$, —CH=CHC$_2$H$_5$, —(CH$_2$)$_2$CH=CH$_2$, —CH=CHC$_3$H$_7$, —(CH$_2$)$_2$CH=CHCH$_3$, —(CH$_2$)$_3$CH=CH$_2$, —CH=CH(CH$_2$)$_2$CH=CH$_2$, —(CH$_2$)$_2$CH=CH(CH$_2$)$_2$CH=CH$_2$, —OCH$_3$, —OC$_2$H$_5$, —OC$_3$H$_7$, —OC$_4$H$_9$ and fluorine.

In formula (1), the ring A$_1$, the ring A$^2$ and the ring A$^3$ are each independently 1,4-cyclohexylene or 1,4-phenylene, and in these rings, arbitrary hydrogen may be replaced by halogen, —CF$_3$ or —OCF$_3$. R$^2$ is halogen or alkenyl having 2 to 10 carbons when the ring A$_1$, the ring A$^2$ and the ring A$^3$ are 1,4-cyclohexylene and/or 1,4-phenylene. That is to say: all of the rings such as the ring A$_1$, the ring A$^2$ and the ring A$^3$ are 1,4-cyclohexylene and/or 1,4-phenylene when R$^2$ is halogen or alkenyl having 2 to 10 carbons.

When these rings are 1,4-cyclohexylene, the refractive index anisotropy (Δn) is small and the viscosity is small, and when this liquid crystal compound is added to a liquid crystal composition, the maximum temperature of a nematic phase is increased.

The refractive index anisotropy (Δn) is relatively increased and the orientational order parameter is also increased, when these rings are 1,4-phenylene in which hydrogen may be replaced by halogen, —CF$_3$ or —OCF$_3$.

Desirable ring A$_1$, ring A$^2$ and ring A$^3$ are 1,4-cyclohexylene, 1,4-phenylene, 2-fluoro-1,4-phenylene, 3-fluoro-1,4-phenylene, 2,3-difluoro-1,4-phenylene, 2,5-difluoro-1,4-phenylene or 3,5-difluoro-1,4-phenylene.

Z$^1$, Z$^2$ and Z$^3$ are each independently a single bond or alkylene having 1 to 4 carbons, and in the alkylene, arbitrary —CH$_2$— may be replaced by —O— or —CO— and arbitrary —(CH$_2$)$_2$— may be replaced by —CH=CH—, and in these groups, arbitrary hydrogen may be replaced by halogen.

Z$^1$, Z$^2$ and Z$^3$ includes a single bond, —(CH$_2$)$_2$—, —CH=CH—, —CF$_2$O—, —OCF$_2$—, —CH$_2$O—, —OCH$_2$—, —CF=CF—, —(CH$_2$)$_4$—, —COO—, —OCO—, —CH$_2$CO—, —COCH$_2$—, —O(CH$_2$)$_2$O—, —(CH$_2$)$_2$COO—, —(CH$_2$)$_2$OCO—, —COO(CH$_2$)$_2$—, —OCO(CH$_2$)$_2$—, —(CH$_2$)$_2$CF$_2$O—, —(CH$_2$)$_2$OCF$_2$—, —CF$_2$O—(CH$_2$)$_2$—, —OCF$_2$(CH$_2$)$_2$—, —CH=CH—CH$_2$O— and —OCH$_2$—CH=CH—. Trans is preferable to cis in the configuration with regard to the double bond of the bonding group such as —CH=CH—, —CF=CF—, —CH=CH—CH$_2$O— and —OCH$_2$—CH=CH—.

Desirable Z$^1$, Z$^2$ and Z$^3$ are a single bond, —(CH$_2$)$_2$—, —(CH$_2$)$_4$—, —COO—, —OCO—, —CF$_2$O—, —OCF$_2$—, —CH=CH—, —CF=CF—, —CH$_2$O— or —OCH$_2$—.

More desirable Z$^1$, Z$^2$ and Z$^3$ are a single bond, —(CH$_2$)$_2$—, —COO—, —OCO—, —CF$_2$O—, —OCF$_2$—, —CH$_2$O— or —OCH$_2$—.

G is —CH$_2$— or —O—.

m, n and p are each independently 0 or 1; and the sum of m, n and p is 1, 2 or 3. The compound where the sum is 1 has a small viscosity and an excellent compatibility at a low temperature. The compound where the sum is 2 or 3 has a high maximum temperature of a nematic phase.

In formula (1), the compound where R$^2$ is alkenyl having 2 to 7 carbons and the ring A$_1$, the ring A$^2$ and the ring A$^3$ are each independently 1,4-cyclohexylene or 1,4-phenylene has a small dielectric anisotropy and a small viscosity. Such a compound can be used for adjusting the refractive index anisotropy, the viscosity, the maximum temperature of a nematic phase, the compatibility at a low temperature and so forth in the liquid crystal composition.

In formula (1), the compound where R$^2$ is —CF$_3$, —OCF$_3$, fluorine or chlorine and the ring A$_1$, the ring A$^2$ and the ring A$^3$ are each independently 1,4-cyclohexylene, 1,4-phenylene, 3-fluoro-1,4-phenylene or 3,5-difluoro-1,4-phenylene has a large dielectric anisotropy. The compound where the ring bonded to R$^2$ is 3-fluoro-1,4-phenylene or 3,5-difluoro-1,4-phenylene has a larger refractive index anisotropy.

In formula (1), the compound were R$^2$ is alkyl having 1 to 7 carbons, alkoxy having 1 to 6 carbons or alkenyl having 2 to 7 carbons and the ring A$_1$, the ring A$^2$ and the ring A$^3$ are each independently 1,4-cyclohexylene, 1,4-phenylene, 2-fluoro-1,4-phenylene, 3-fluoro-1,4-phenylene or 2,3-difluoro-1,4-phenylene, and at least one of the ring A$_1$, the ring A$^2$ and the ring A$^3$ is 2,3-difluoro-1,4-phenylene has a large negative refractive index anisotropy.

The compound (1) of the invention can be prepared by the introduction of a predetermined group into R$^1$, R$^2$, the ring A$_1$, the ring A$^2$, the ring A$^3$, Z$^1$, Z$^2$, Z$^3$ and G in the formula, and the introduction of such groups can be carried out by known and general synthetic organic methods. Representative examples of the synthesis include the methods described in "Vol. 14: Synthesis and Reaction of Organic Compounds" (1978) in New Experimental Chemistry Course (Shin Jikken Kagaku Kouza, in Japanese; Maruzen Co., Ltd.), or "Vol. 19 to Vol. 26: Organic Synthesis I to VIII" (1991) in Experimental Chemistry Course (Jikken KagakuKouza, in Japanese; the fourth edition, Maruzen Co., Ltd.).

With regard to an example of the method for the formation of the bonding group Z$^1$, Z$^2$ or Z$^3$, the scheme will be shown first and then the scheme will be explained in item (I) to item (XI). In this scheme, MSG$^1$ or MSG$^2$ is a monovalent organic group having at least one ring. A plurality of MSG$^1$ (or MSG$^2$) used in the scheme may mean the same group or different groups. The compounds (1A) to (1K) correspond to the compound (1).

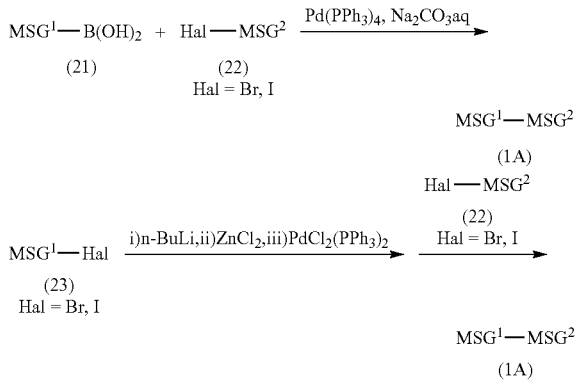

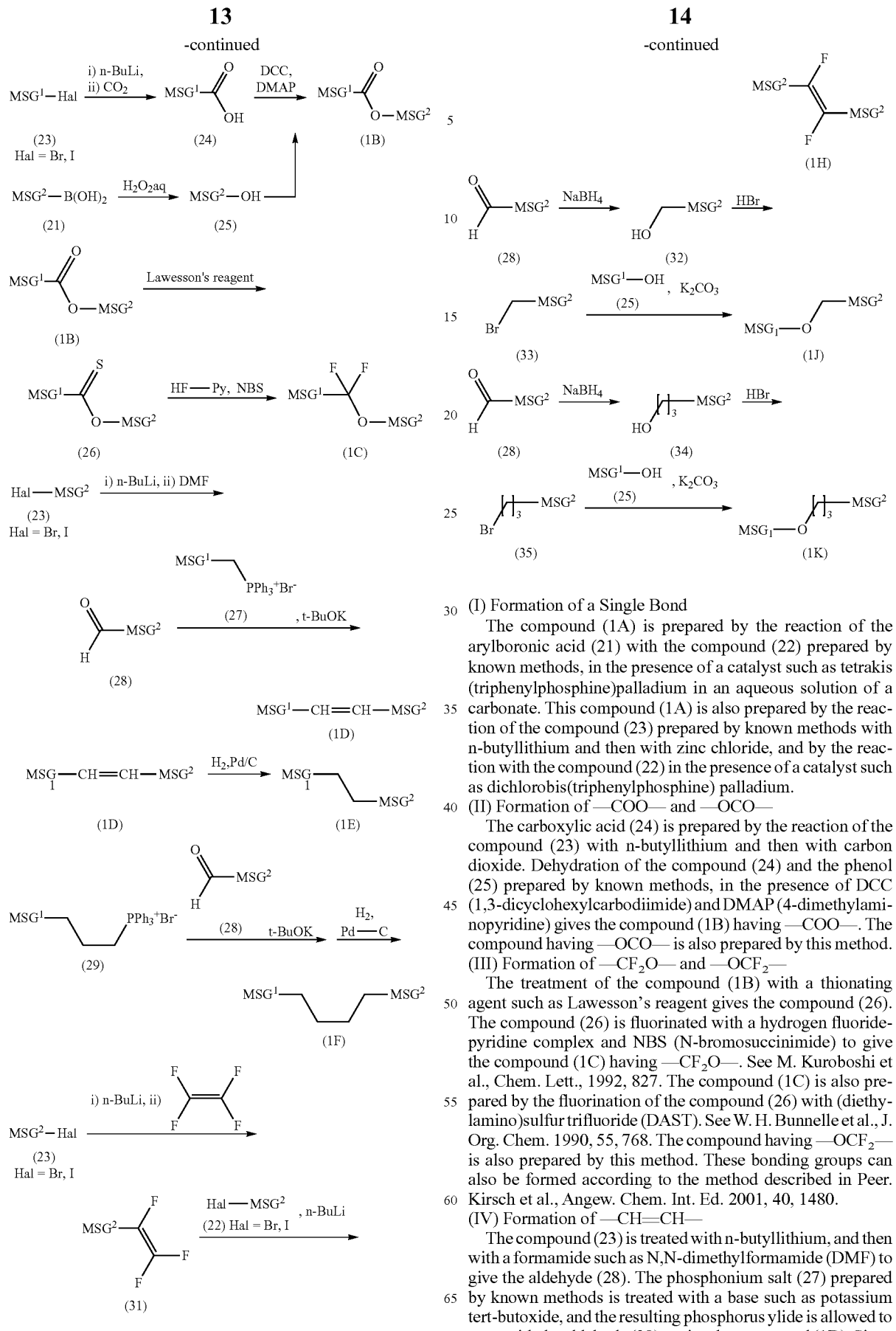

(I) Formation of a Single Bond

The compound (1A) is prepared by the reaction of the arylboronic acid (21) with the compound (22) prepared by known methods, in the presence of a catalyst such as tetrakis(triphenylphosphine)palladium in an aqueous solution of a carbonate. This compound (1A) is also prepared by the reaction of the compound (23) prepared by known methods with n-butyllithium and then with zinc chloride, and by the reaction with the compound (22) in the presence of a catalyst such as dichlorobis(triphenylphosphine) palladium.

(II) Formation of —COO— and —OCO—

The carboxylic acid (24) is prepared by the reaction of the compound (23) with n-butyllithium and then with carbon dioxide. Dehydration of the compound (24) and the phenol (25) prepared by known methods, in the presence of DCC (1,3-dicyclohexylcarbodiimide) and DMAP (4-dimethylaminopyridine) gives the compound (1B) having —COO—. The compound having —OCO— is also prepared by this method.

(III) Formation of —CF$_2$O— and —OCF$_2$—

The treatment of the compound (1B) with a thionating agent such as Lawesson's reagent gives the compound (26). The compound (26) is fluorinated with a hydrogen fluoride-pyridine complex and NBS (N-bromosuccinimide) to give the compound (1C) having —CF$_2$O—. See M. Kuroboshi et al., Chem. Lett., 1992, 827. The compound (1C) is also prepared by the fluorination of the compound (26) with (diethylamino)sulfur trifluoride (DAST). See W. H. Bunnelle et al., J. Org. Chem. 1990, 55, 768. The compound having —OCF$_2$— is also prepared by this method. These bonding groups can also be formed according to the method described in Peer. Kirsch et al., Angew. Chem. Int. Ed. 2001, 40, 1480.

(IV) Formation of —CH=CH—

The compound (23) is treated with n-butyllithium, and then with a formamide such as N,N-dimethylformamide (DMF) to give the aldehyde (28). The phosphonium salt (27) prepared by known methods is treated with a base such as potassium tert-butoxide, and the resulting phosphorus ylide is allowed to react with the aldehyde (28) to give the compound (1D). Since the cis-isomer is formed depending on the reaction conditions, the cis-isomer is isomerized to the trans-isomer by known methods as requested.

(V) Formation of —(CH$_2$)$_2$—

The compound (1E) is prepared by the hydrogenation of the compound (1D) in the presence of a catalyst such as palladium on carbon.

(VI) Formation of —(CH$_2$)$_4$—

A compound having —(CH$_2$)$_2$—CH=CH— is prepared according to the method described in item (IV), using the phosphonium salt (29) instead of the phosphonium salt (27). The catalytic hydrogenation of the resulting compound gives the compound (1F).

(VII) Formation of —CF=CF—

The compound (23) is treated with n-butyllithium, and then allowed to react with tetrafluoroethylene to give the compound (31). The compound (22) is treated with n-butyllithium, and then allowed to react with the compound (31) to give the compound (1H).

(VIII) Formation of —CH$_2$O— or —OCH$_2$—

The compound (28) is reduced with a reducing agent such as sodium borohydride to give the compound (32). The compound (32) is halogenated with hydrobromic acid or the like, giving the compound (33). The compound (33) is allowed to react with the compound (25) in the presence of potassium carbonate or the like, giving the compound (1J).

(IX) Formation of —(CH$_2$)$_3$O— or —O(CH$_2$)$_3$—

The compound (1K) is prepared according to the method described in item (VIII), using the compound (34) instead of the compound (32).

(X) Formation of —(CF$_2$)$_2$—

A compound having —(CF$_2$)$_2$— is prepared by fluorination of a diketone (—COCO—) with sulfur tetrafluoride in the presence of a hydrogen fluoride catalyst according to the method described in J. Am. Chem. Soc., 2001, 123, 5414.

Next, an example of the method for the preparation of the cyclopentanone represented by formula (1) will be shown. First, the scheme on the preparation of the reaction intermediate (36) having a cyclopentanone skeleton will be explained, and then one example of the method for the preparation of the compound having a tetrahydrofuran ring, which is represented by formula (1) will be described.

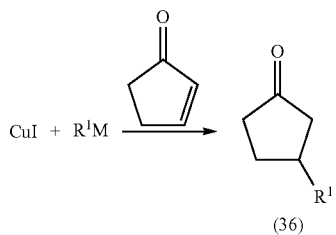

(36)

In the compound (36), the definition of R$^1$ is just the same as described in item 1.

The organometallic compound R$^1$M is allowed to react with copper iodide, giving an organocopper compound, and the compound (36) is prepared by the reaction of the resulting organocopper compound with 2-cyclopentene-1-one. An organolithium compound, a Grignard reagent or the like can be used as the organometallic compound. The reaction is carried out in a solvent such as diethyl ether or THF at −78° C. by use of a reaction vessel in which air is replaced by nitrogen gas. First, an organocopper compound is prepared by the reaction of an organometallic compound with copper iodide, where a complex may be prepared by the addition of tributylphosphine, dimethylsulfide or the like. Then, the organocopper compound is allowed to react with 2-cyclopentene-1-one at −78° C. to give the reaction intermediate (36) having a cyclopentanone skeleton.

The compound (1) can be prepared by use of the compound (36) itself according to the methods described in (I) to (XI) described above. Alternatively, the compound (1) can also be prepared after the compound (36) has been derivatized to give an alcohol, an aldehyde, a carboxylic acid or the like, as required, via functional transformation according to the methods in synthetic organic chemistry.

A compound having a tetrahydrofuran ring can be prepared from a starting material such as a γ-lactone. The γ-lactone is commercially available as a reagent or is prepared according to the method described in Tetrahedron Lett., 211, 55029 (1980) or the like. The compound (1) can be prepared by use of the γ-lactone itself according to the methods previously described in (I) to (XI). Alternatively, the compound (1) can also be prepared after the γ-lactone has been derivatized to give an alcohol, an aldehyde, a carboxylic acid or the like, as required, via functional transformation according to the methods in synthetic organic chemistry.

The compound of the invention has an excellent compatibility with other liquid crystal compositions, a small viscosity and a wide temperature range of a liquid crystal phase in comparison with known compounds having a similar structure. The compound has a low threshold voltage and a relatively small viscosity in comparison with a similar compound. Further, the compound of the invention is sufficiently stable physically and chemically under conditions that the liquid crystal display device is usually used, and is particularly excellent as a component of a nematic liquid crystal composition, and can suitably be used as a component of the liquid crystal composition for use in TN, STN, TFT, VA, IPS and PSA mode-devices.

The liquid crystal composition of the invention includes the compound (1) as the component A. The composition may include a component such as the components B, C, D and E, these of which will be shown below. The composition may further include a liquid crystal compound which is not described in this specification. Incidentally, liquid crystal compounds included in the composition may be only the component A. The content of the component A is suitably in the range of approximately 1% to approximately 99% by weight, preferably in the range of approximately 3% to approximately 90% by weight, and more preferably in the range of approximately 5% to approximately 60% by weight based on the total weight of the liquid crystal composition.

Desirable components that will be added to the component A are the component B that is at least one compound selected from the group of compounds represented by formulas (2), (3) and (4), and/or the component C that is at least one compound selected from the group of compounds represented by formulas (5), and/or the component D that is at least one compound selected from the group of compounds represented by formulas (6), (7), (8), (9), (10) and (11). Further, the threshold voltage, the temperature range of liquid crystal phases, the refractive index anisotropy, the dielectric anisotropy, the viscosity and so forth can be adjusted by the addition of the component E that is at least one compound selected from the group of compounds represented by formulas (12), (13) and (14).

In each component of the invention in the liquid crystal composition, there are no major differences in characteristics even if the component is an analogue composed of isotopes of each element.

In the component B, desirable examples of the compound (2) include the compounds (2-1) to (2-16), desirable examples of the compound (3) include the compounds (3-1) to (3-112), and desirable examples of the compound (4) include the compounds (4-1) to (4-54)
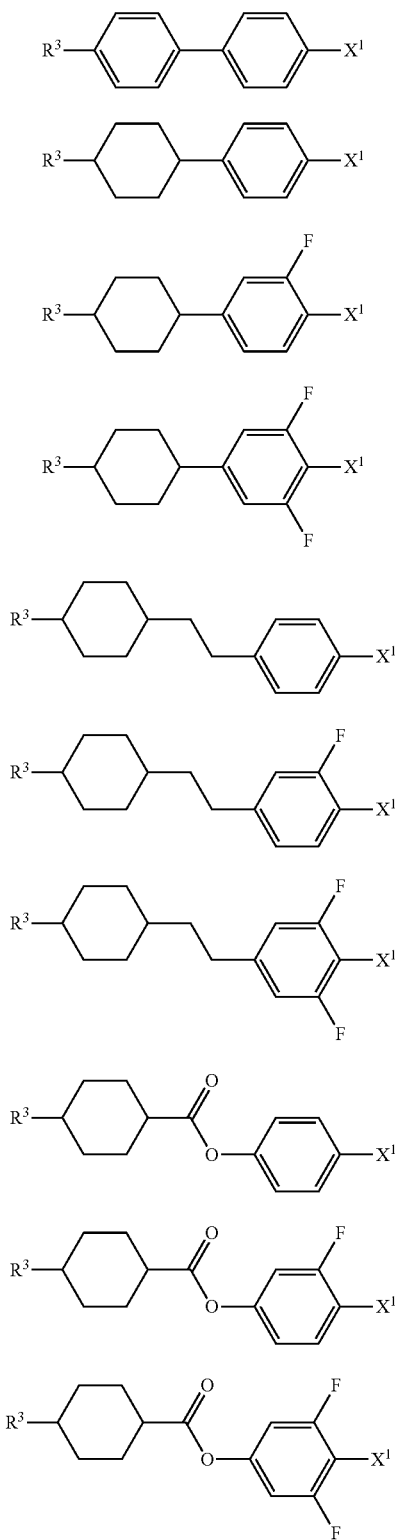
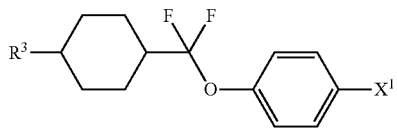
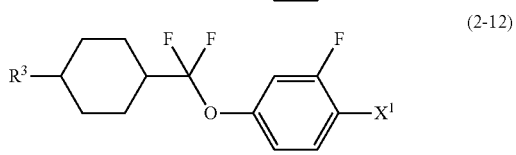
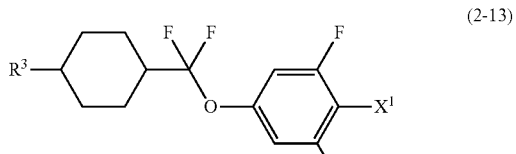
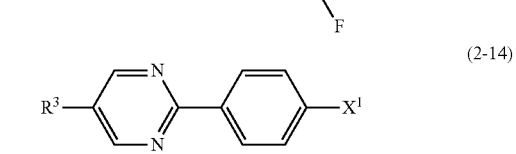
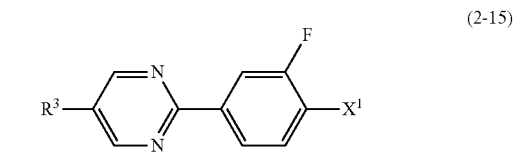
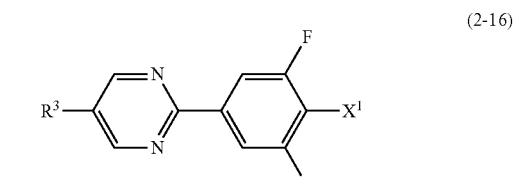
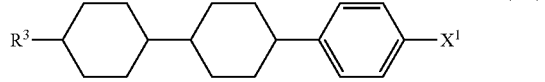
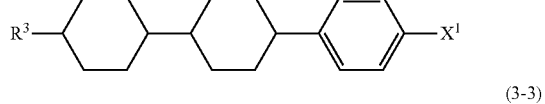
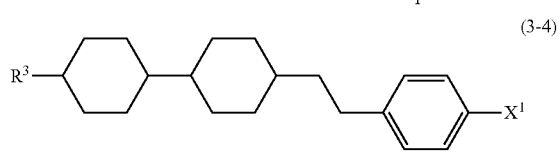
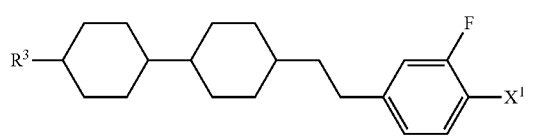

(3-6) 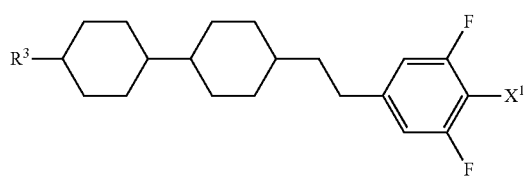
(3-7) 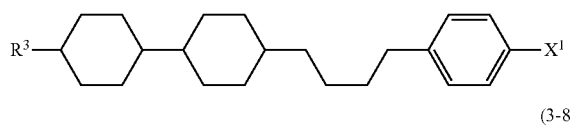
(3-8) 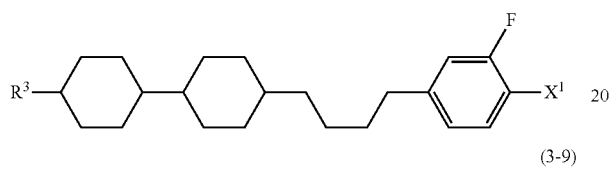
(3-9) 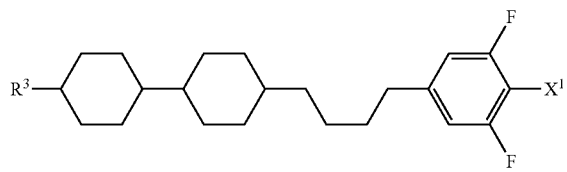
(3-10) 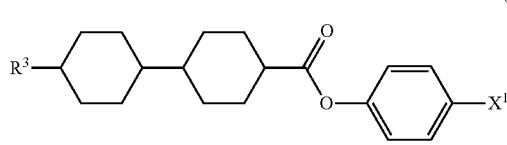
(3-11) 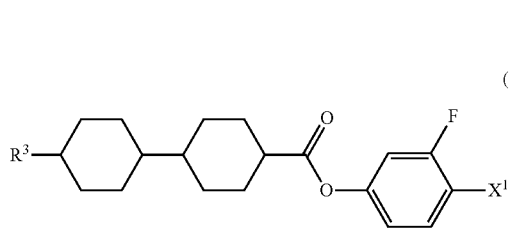
(3-12) 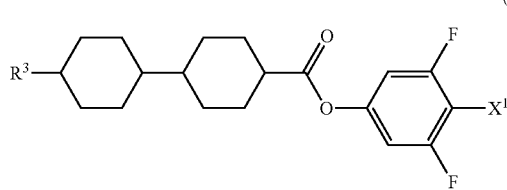
(3-13) 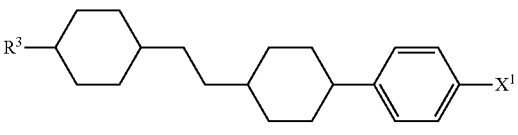
(3-14) 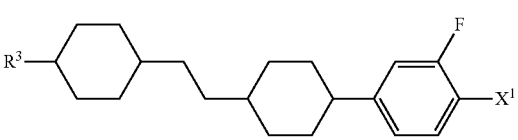
(3-15) 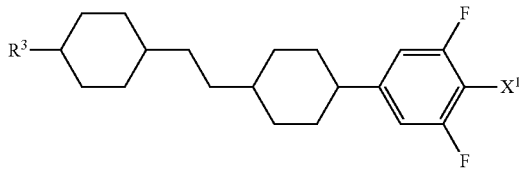
(3-16) 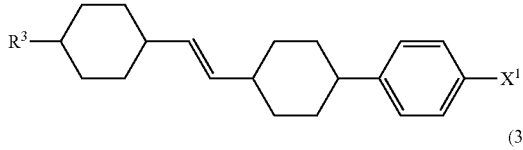
(3-17) 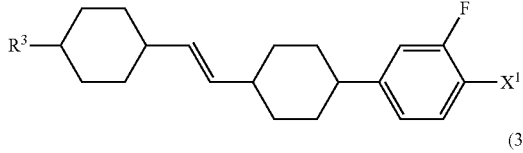
(3-18) 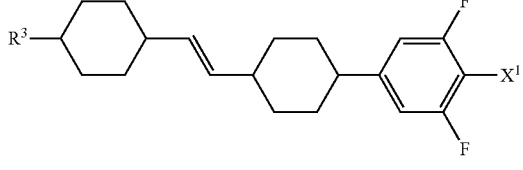
(3-19) 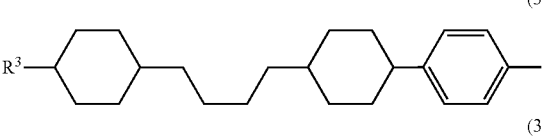
(3-20) 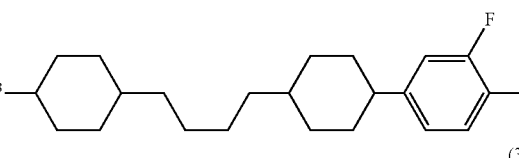
(3-21) 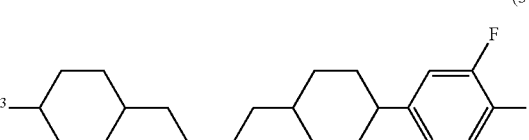
(3-22) 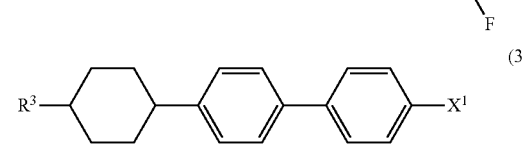
(3-23) 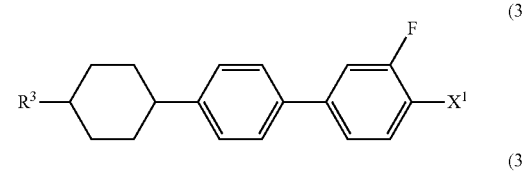
(3-24)

(3-25)
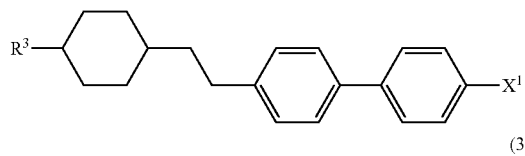
(3-26)
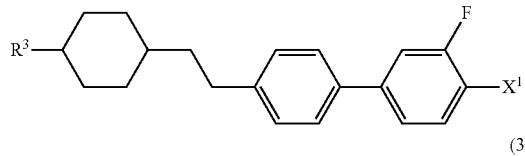
(3-27)
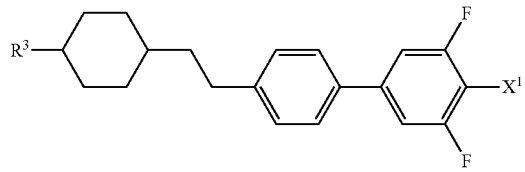
(3-28)
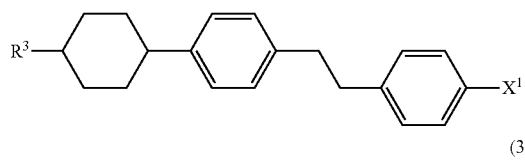
(3-29)
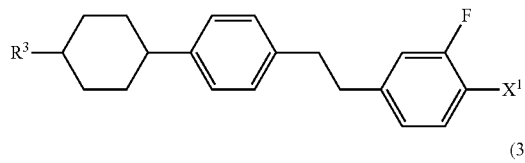
(3-30)
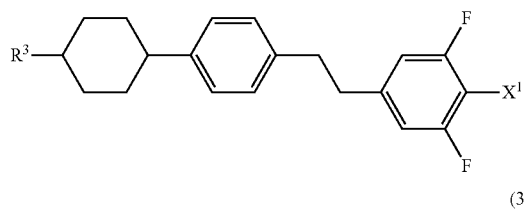
(3-31)
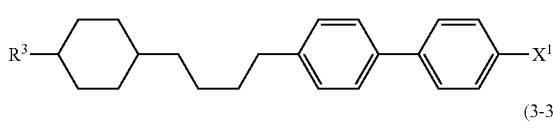
(3-32)
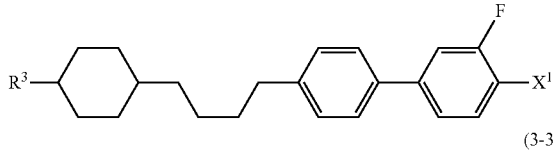
(3-33)
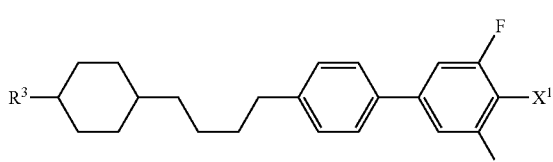
(3-34)
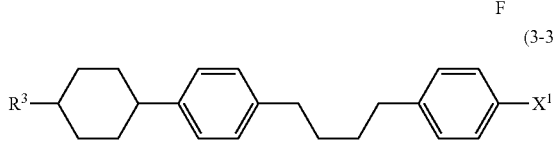
(3-35)
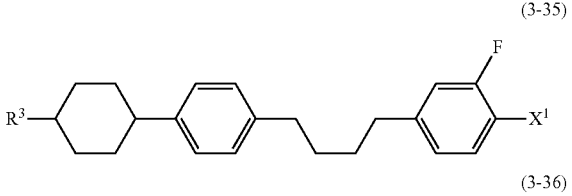
(3-36)
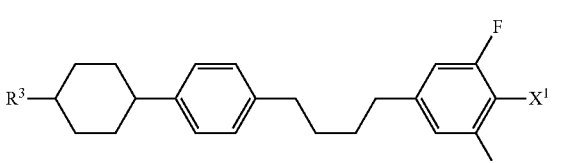
(3-37)
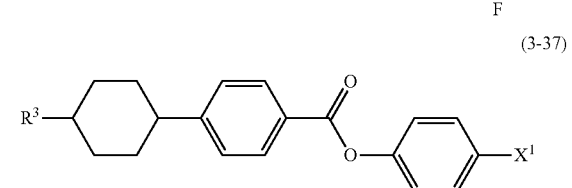
(3-38)
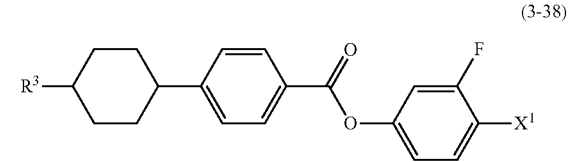
(3-39)
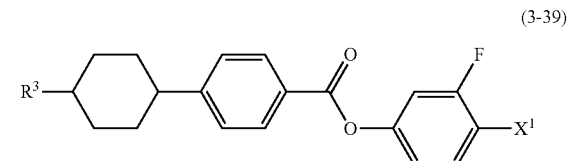
(3-40)
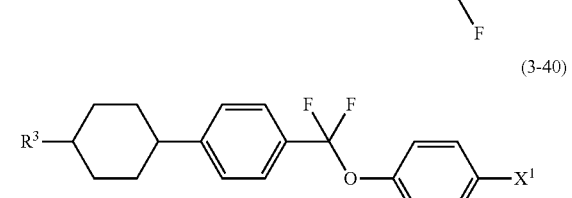
(3-41)
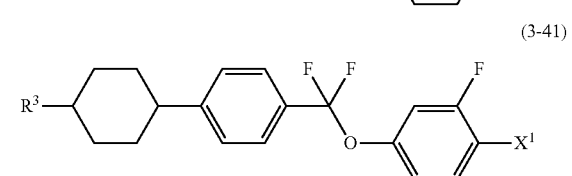
(3-42)
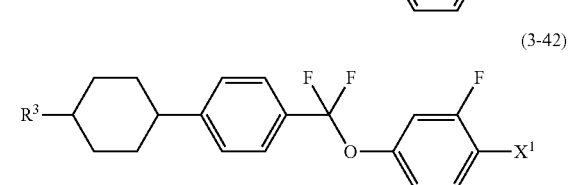
(3-43)
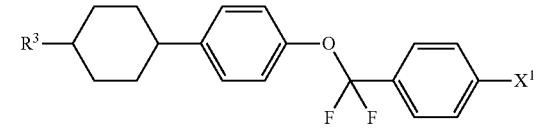

(3-44)
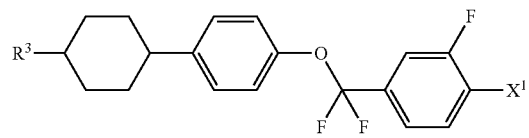
(3-45)
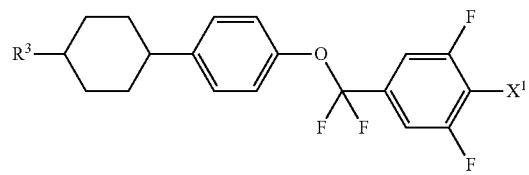
(3-46)
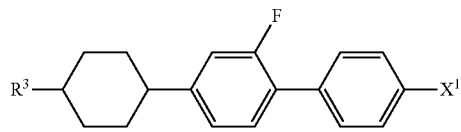
(3-47)
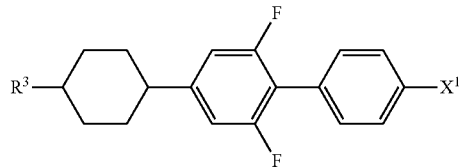
(3-48)
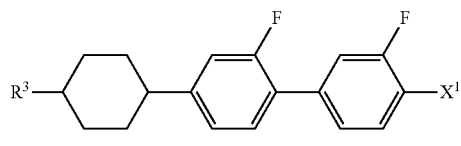
(3-49)
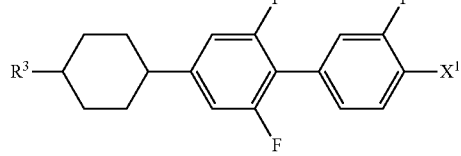
(3-50)
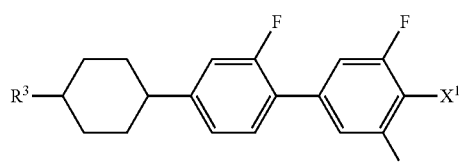
(3-51)
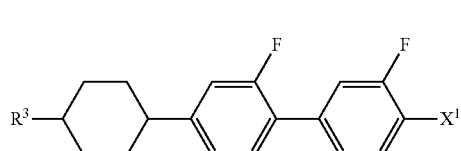
(3-52)
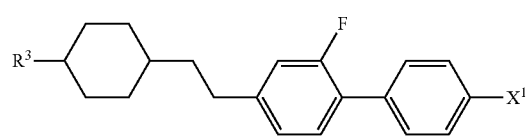
(3-53)
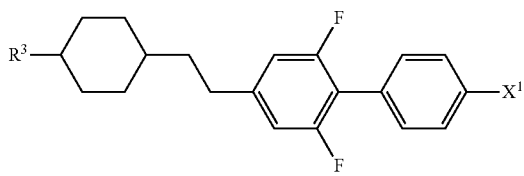
(3-54)
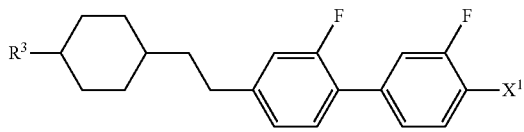
(3-55)
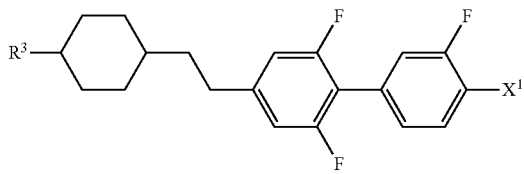
(3-56)
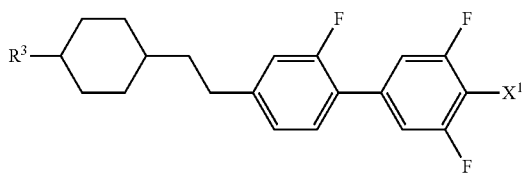
(3-57)
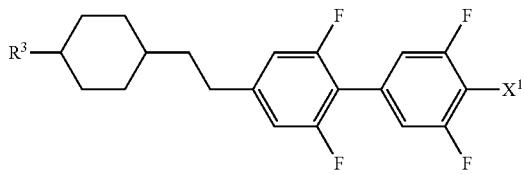
(3-58)
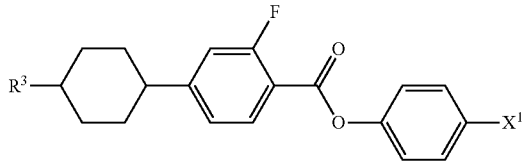
(3-59)
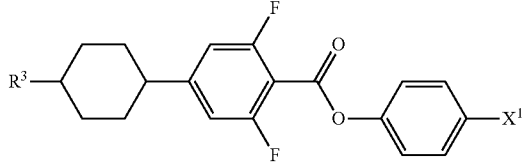
(3-60)
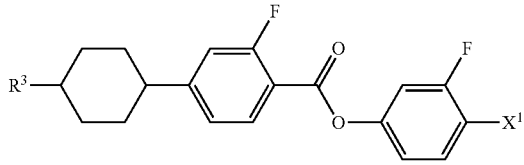

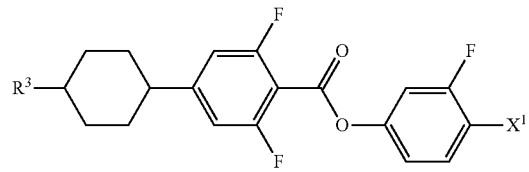
(3-61)
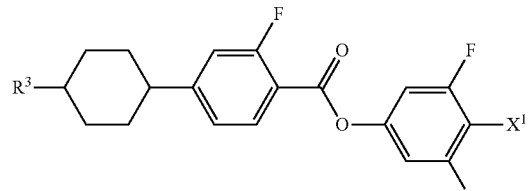
(3-62)
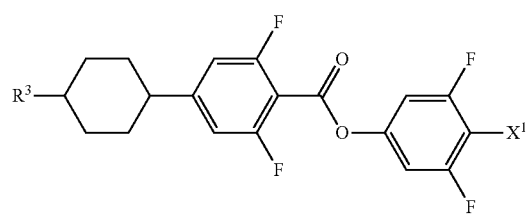
(3-63)
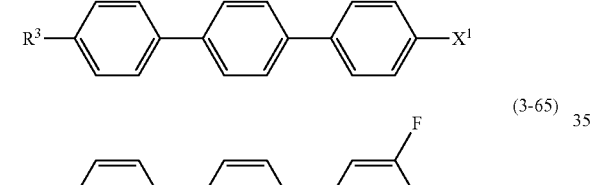
(3-64)
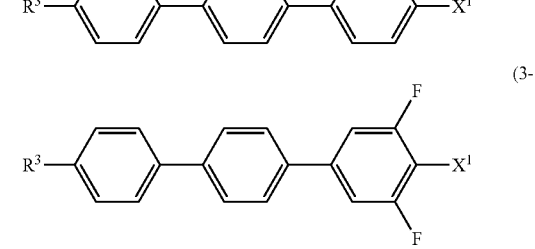
(3-65)
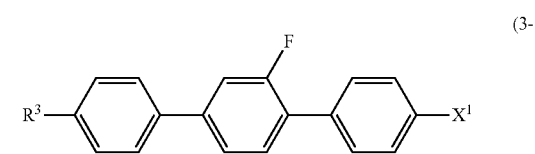
(3-66)
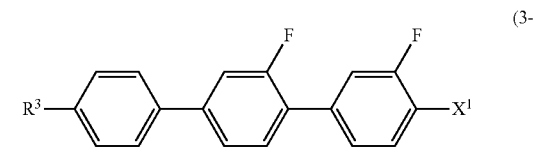
(3-67)
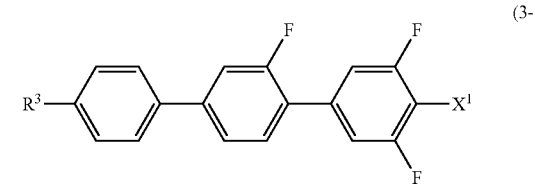
(3-68)
(3-69)
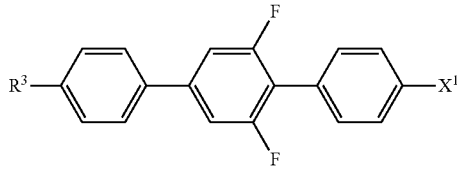
(3-70)
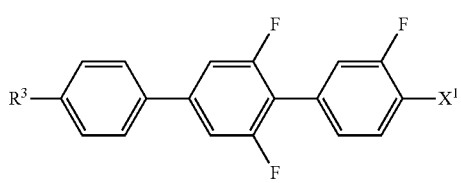
(3-71)
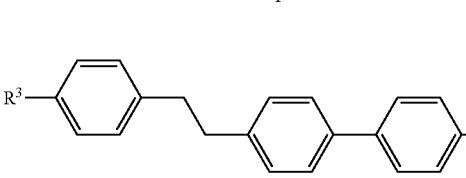
(3-72)
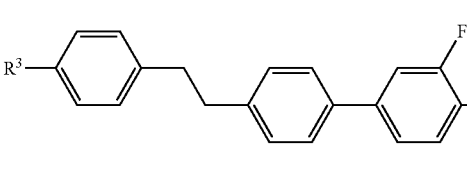
(3-73)
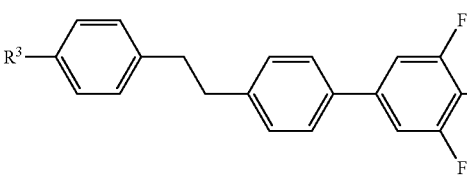
(3-74)
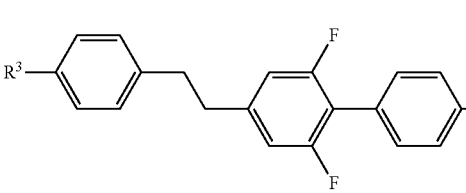
(3-75)
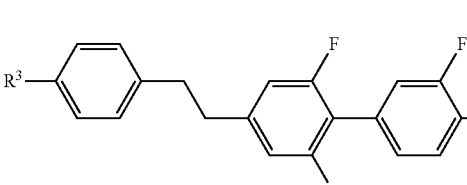
(3-76)
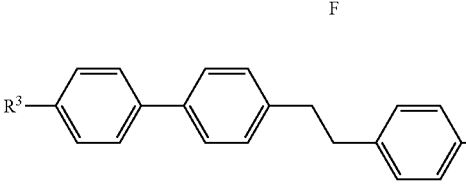
(3-77)
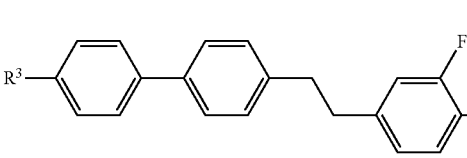
(3-78)

(3-79) 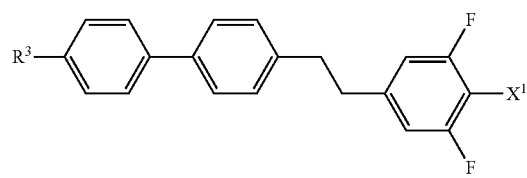
(3-80) 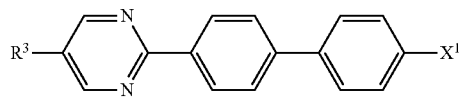
(3-81) 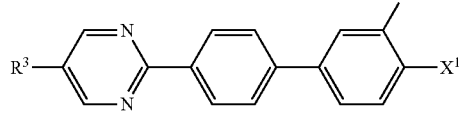
(3-82) 
(3-83) 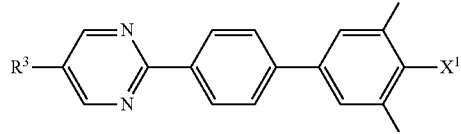
(3-84) 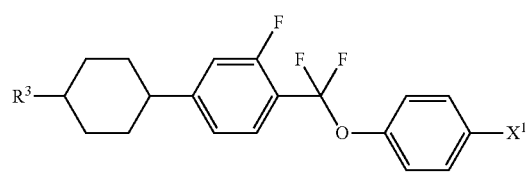
(3-85) 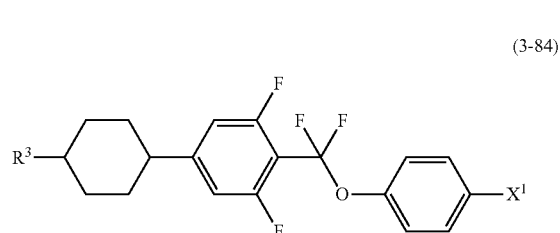
(3-86) 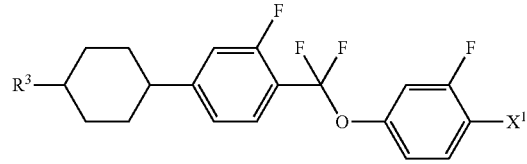
(3-87) 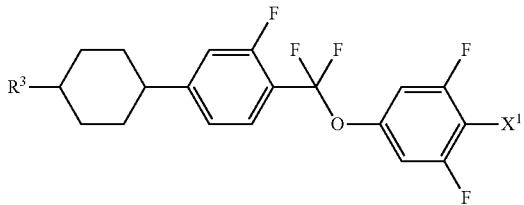
(3-88) 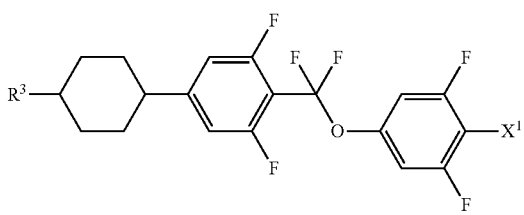
(3-89) 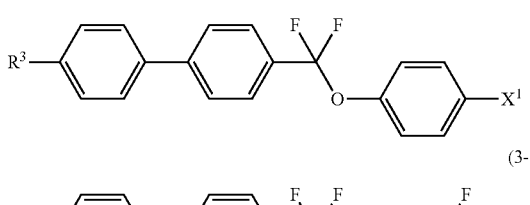
(3-90) 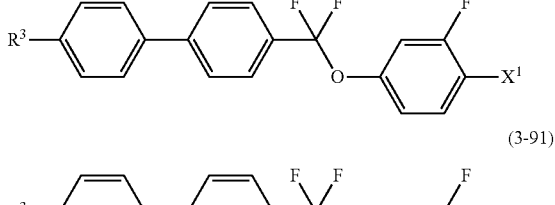
(3-91) 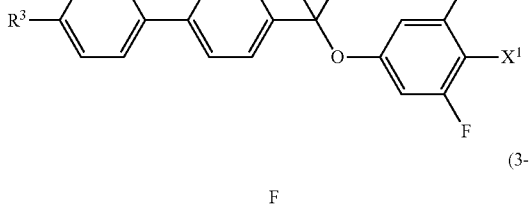
(3-92) 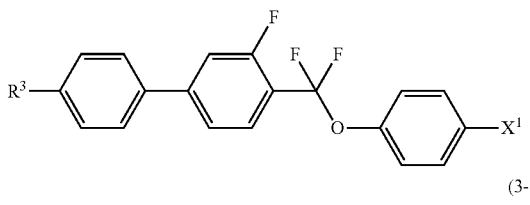
(3-93) 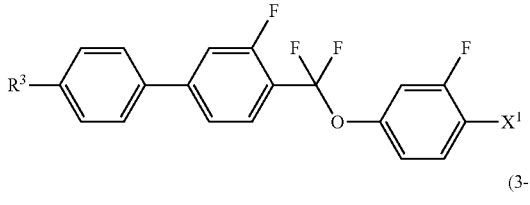
(3-94) 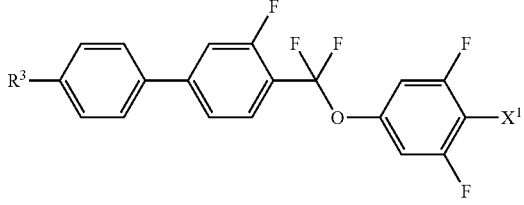

(3-95) 
(3-96) 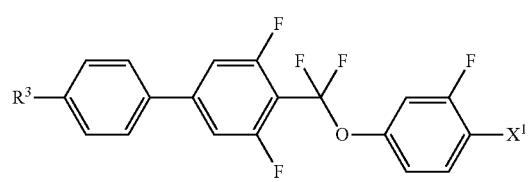
(3-97) 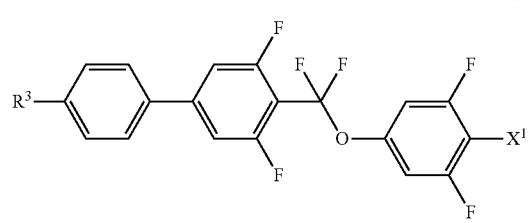
(3-98) 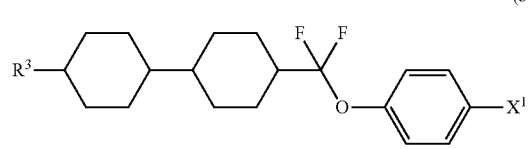
(3-99) 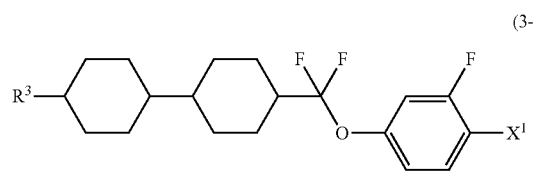
(3-100) 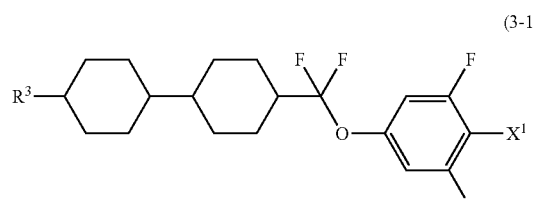
(3-101) 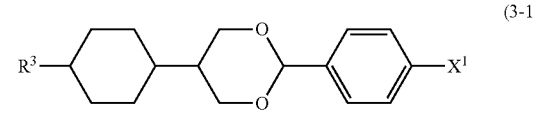
(3-102) 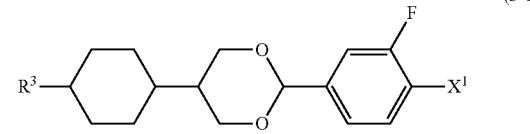
(3-103) 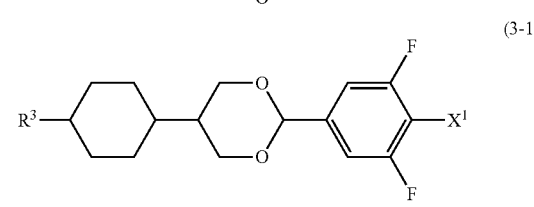
(3-104) 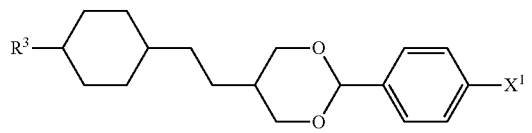
(3-105) 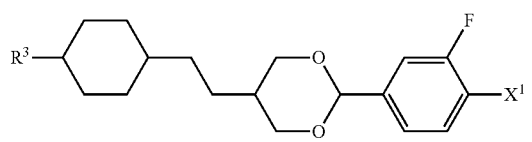
(3-106) 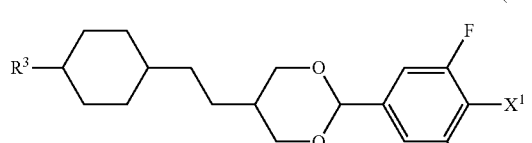
(3-107) 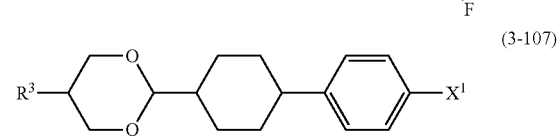
(3-108) 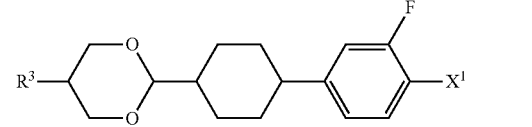
(3-109) 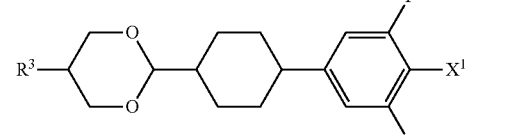
(3-110) 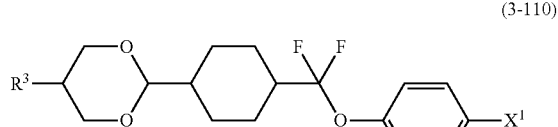
(3-111) 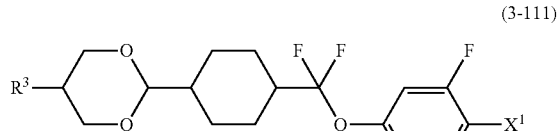
(3-112) 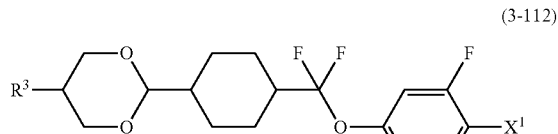
(4-1) 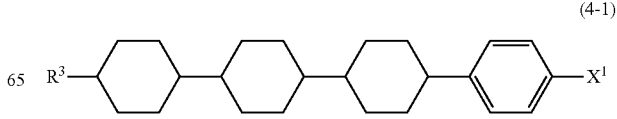

(4-2) 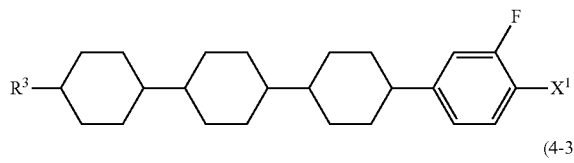
(4-3) 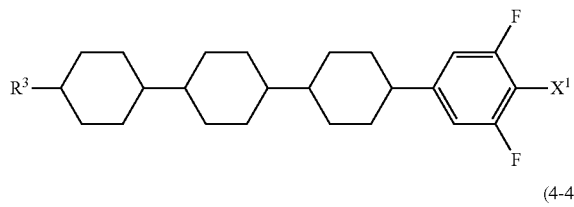
(4-4) 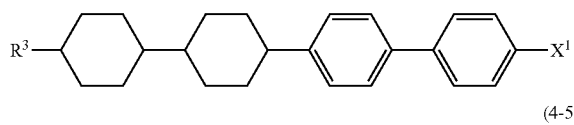
(4-5) 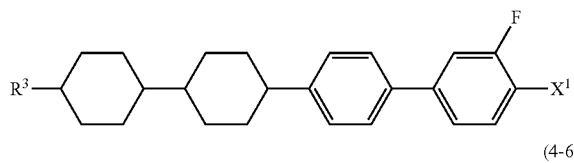
(4-6) 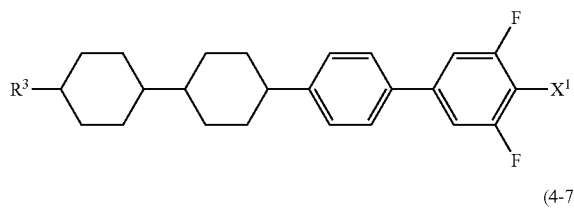
(4-7) 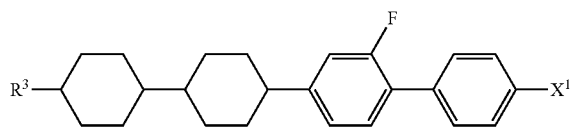
(4-8) 
(4-9) 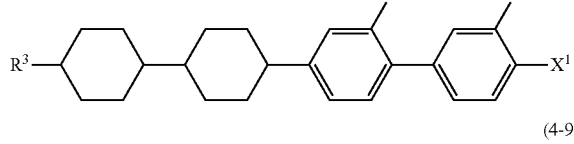
(4-10) 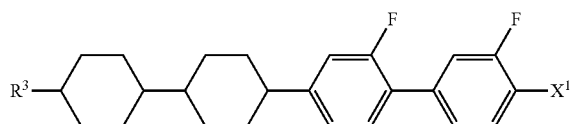
(4-11) 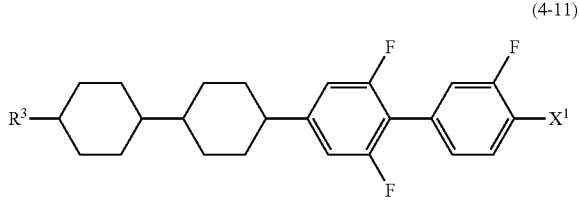
(4-12) 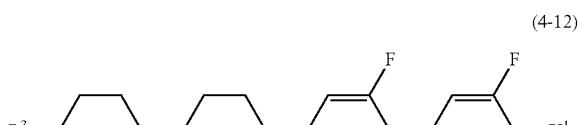
(4-13) 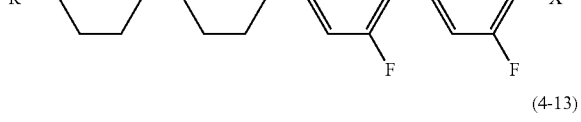
(4-14) 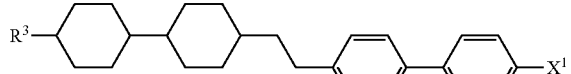
(4-15) 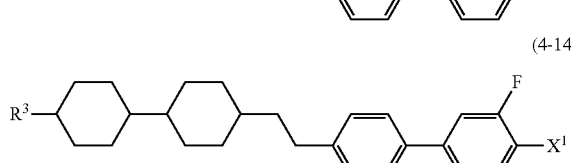
(4-16) 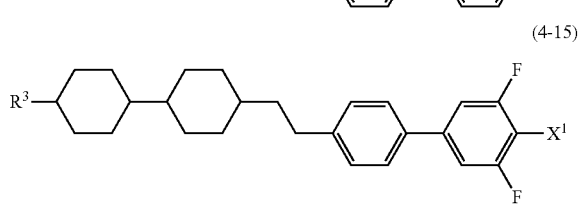
(4-17) 
(4-18) 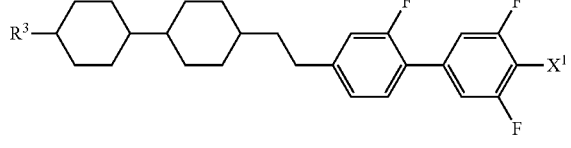
(4-19) 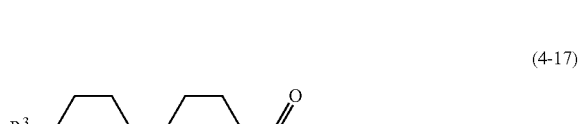

(4-20) 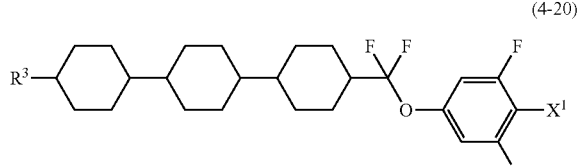
(4-21) 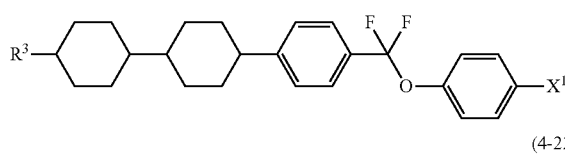
(4-22) 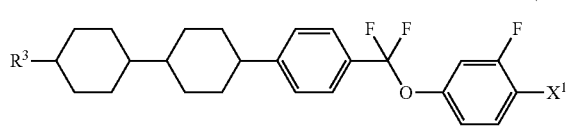
(4-23) 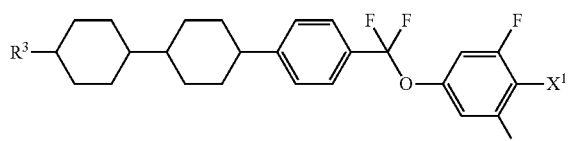
(4-24) 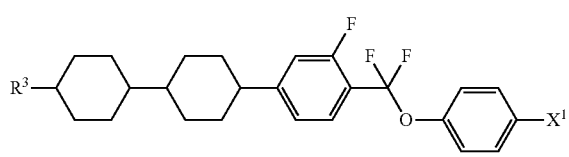
(4-25) 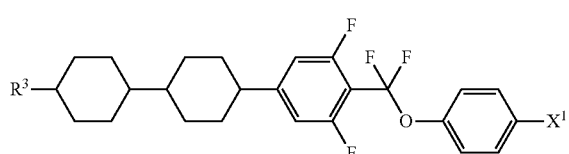
(4-26) 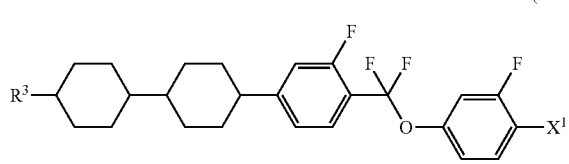
(4-27) 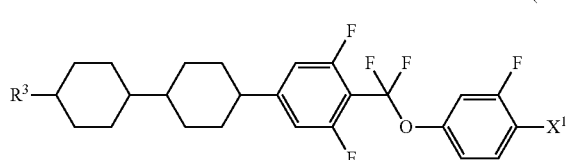
(4-28) 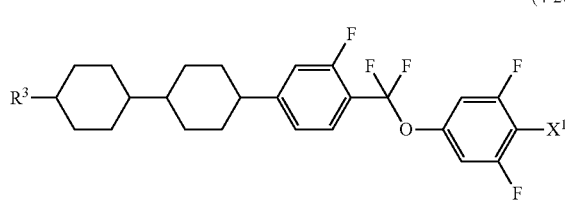
(4-29) 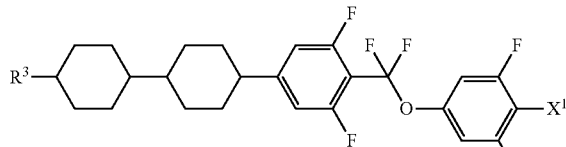
(4-30) 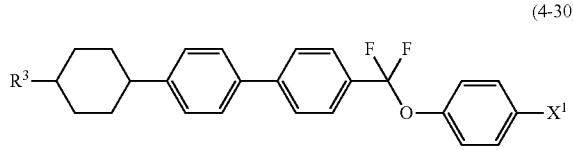
(4-31) 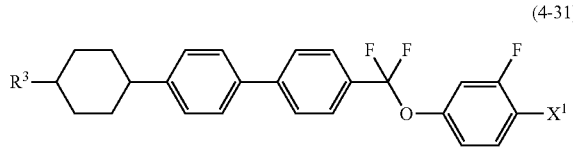
(4-32) 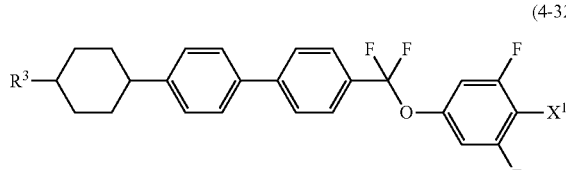
(4-33) 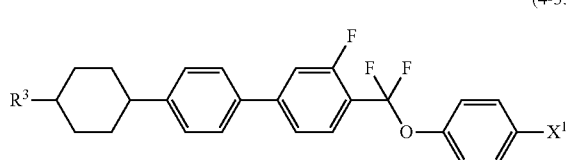
(4-34) 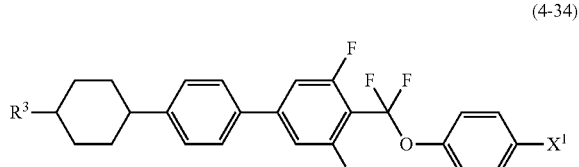
(4-35) 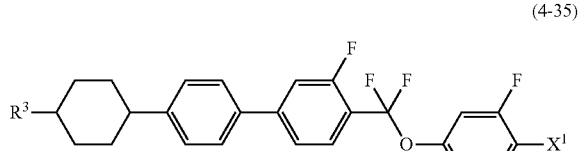
(4-36) 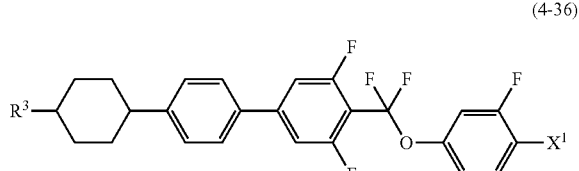
(4-37) 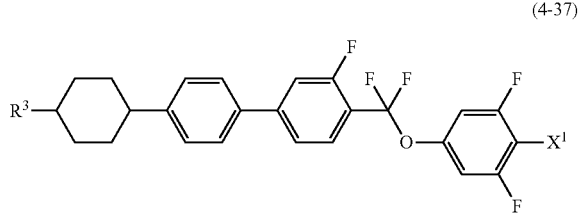

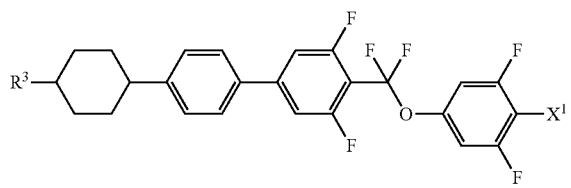
(4-38)
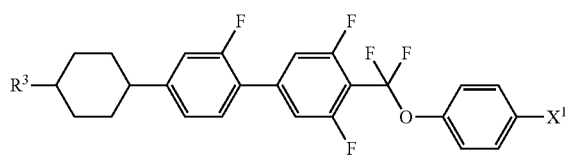
(4-39)
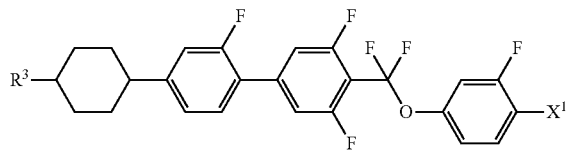
(4-40)
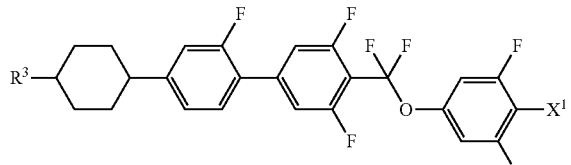
(4-41)
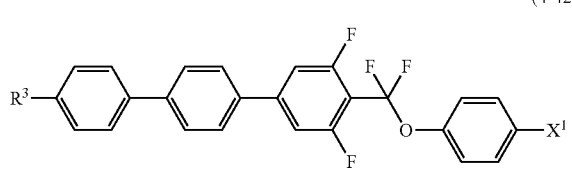
(4-42)
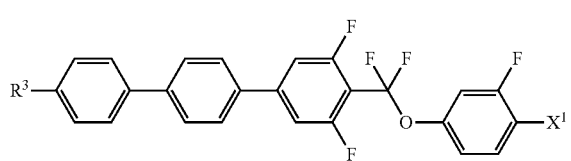
(4-43)
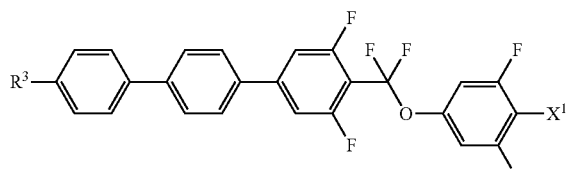
(4-44)
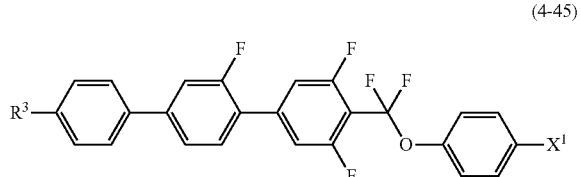
(4-45)
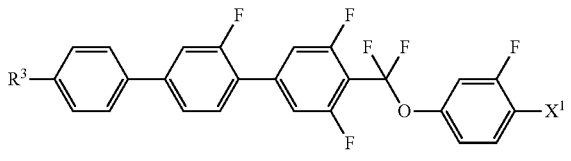
(4-46)
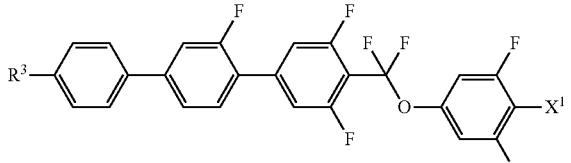
(4-47)
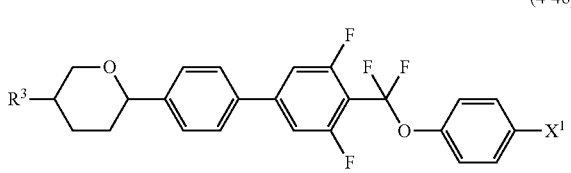
(4-48)
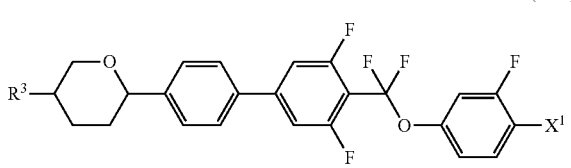
(4-49)
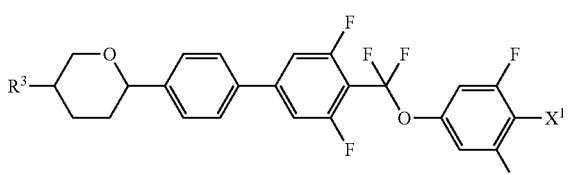
(4-50)
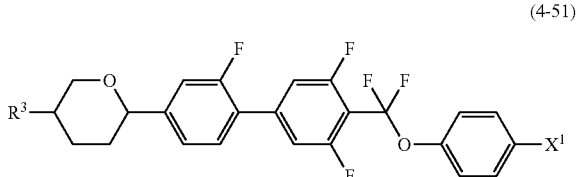
(4-51)
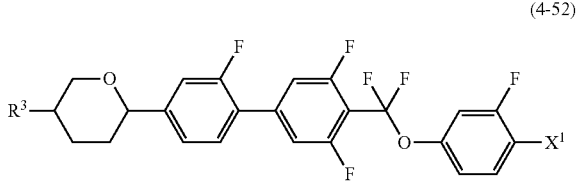
(4-52)
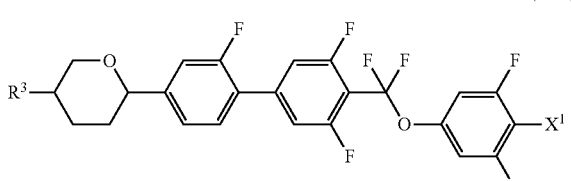
(4-53)

(4-54)

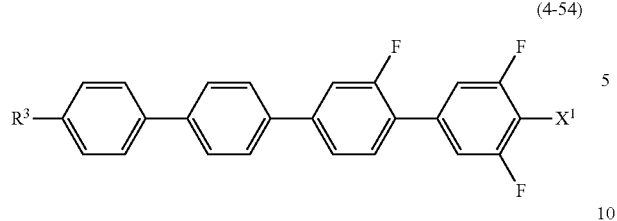

In the formula, the definitions of $R^3$ and $X^1$ are just the same as described previously.

These compounds (2) to (4), that is the component B, are used in the preparation of the liquid crystal composition for use in TFT and PSA mode-device, since they have positive dielectric anisotropy and a particularly excellent thermal or chemical stability. The content of the component B in the liquid crystal composition of the invention is suitably in the range of approximately 1% to approximately 99% by weight, preferably in the range of approximately 10% to approximately 97% by weight, and more preferably approximately 40% to approximately 95% by weight based on the total weight of the liquid crystal composition. The viscosity can be adjusted by a further addition of the compounds (12) to (14) (the component E).

Desirable examples of the compound (5) described above, that is the component C, include the compounds (5-1) to (5-64).

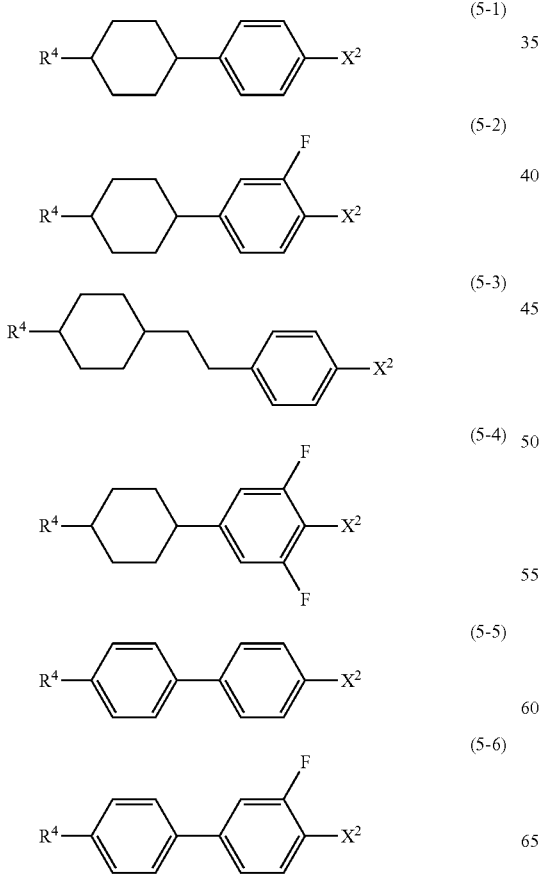

(5-1)
(5-2)
(5-3)
(5-4)
(5-5)
(5-6)

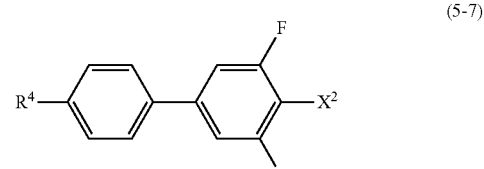

(5-7)

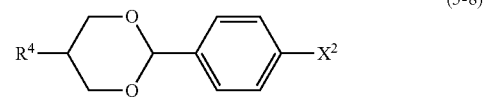

(5-8)

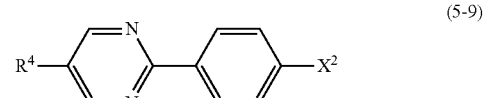

(5-9)

(5-10)

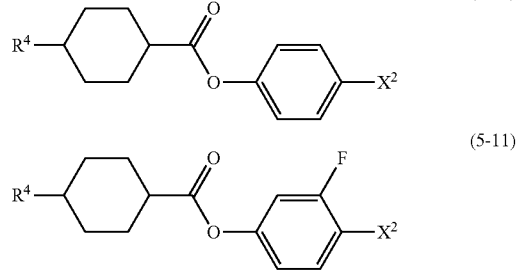

(5-11)
(5-12)

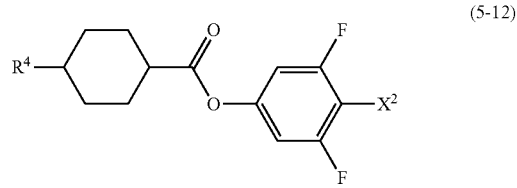

(5-13)
(5-14)
(5-15)

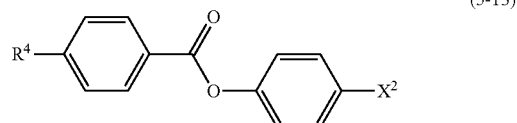

(5-16)

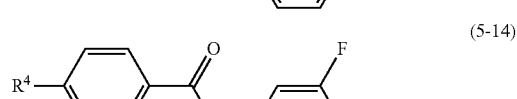

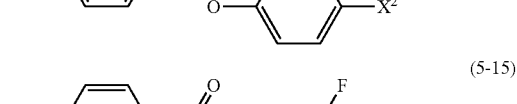

(5-17)

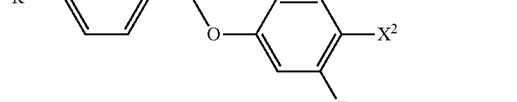

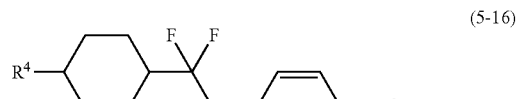

(5-18) 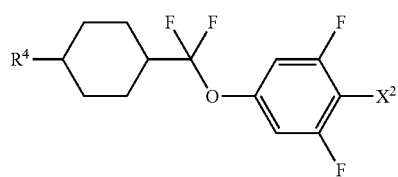
(5-19) 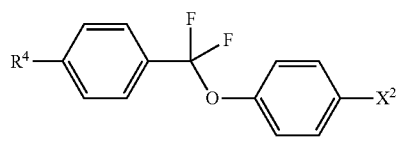
(5-20) 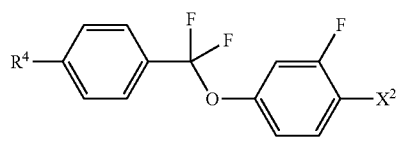
(5-21) 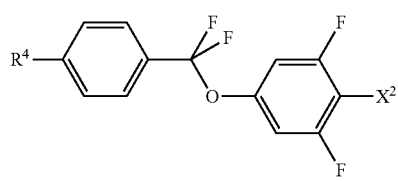
(5-22) 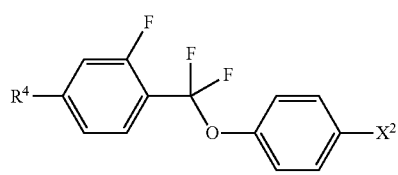
(5-23) 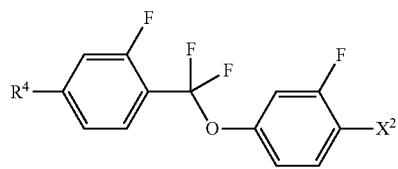
(5-24) 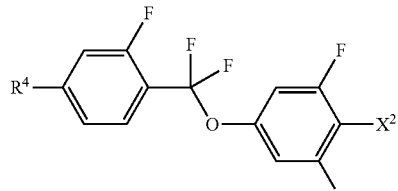
(5-25) 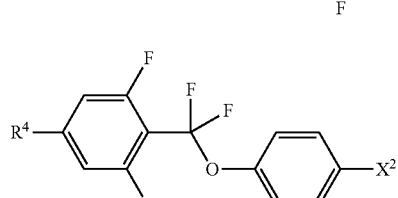
(5-26) 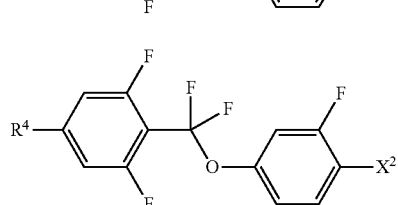
(5-27) 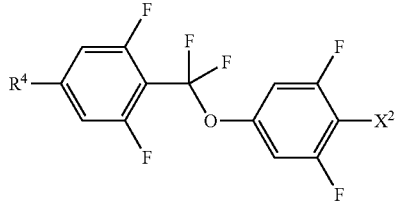
(5-28) 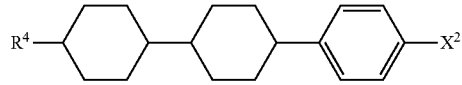
(5-29) 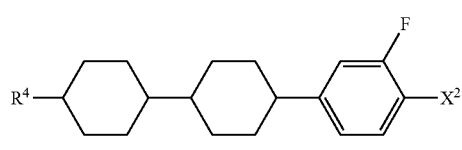
(5-30) 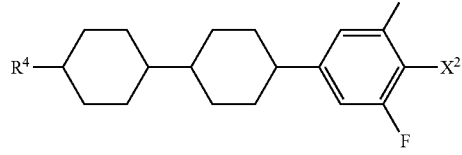
(5-31) 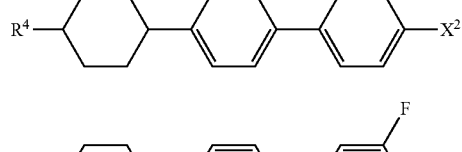
(5-32) 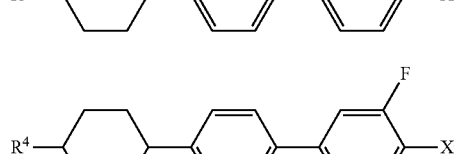
(5-33) 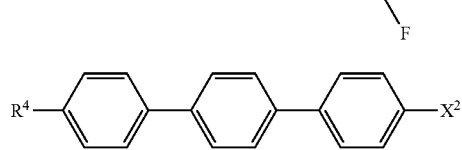
(5-34) 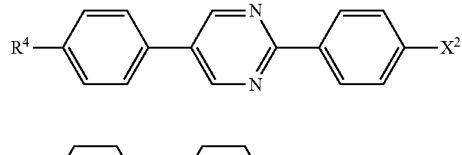
(5-35) 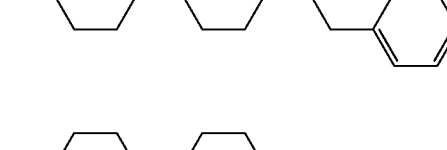
(5-36) 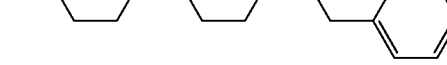
(5-37) 

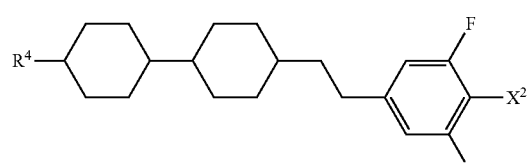
(5-38)
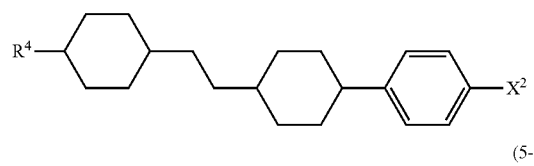
(5-39)
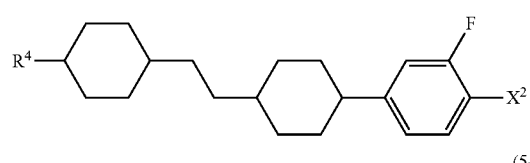
(5-40)
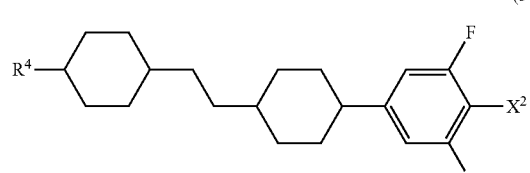
(5-41)
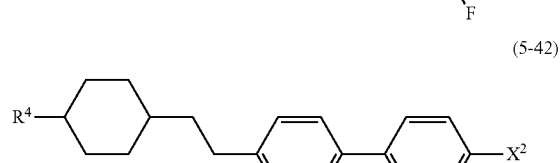
(5-42)
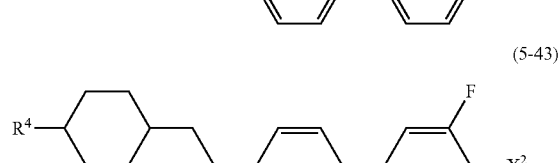
(5-43)
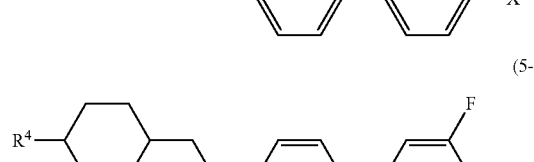
(5-44)
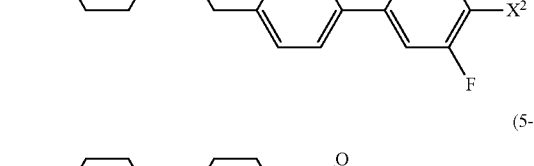
(5-45)
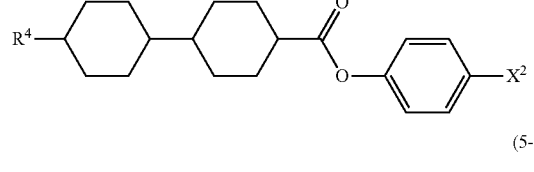
(5-46)
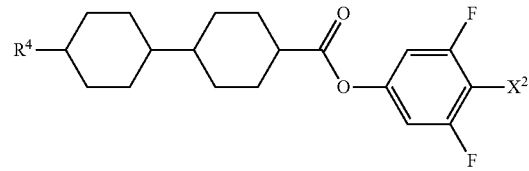
(5-47)
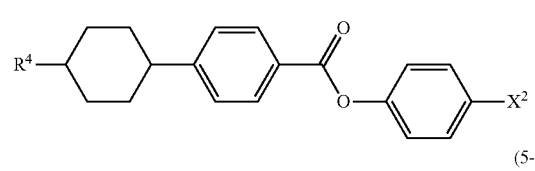
(5-48)
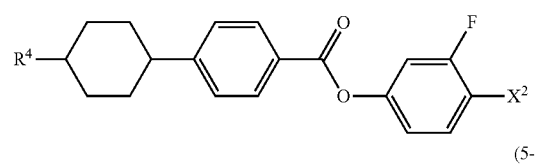
(5-49)
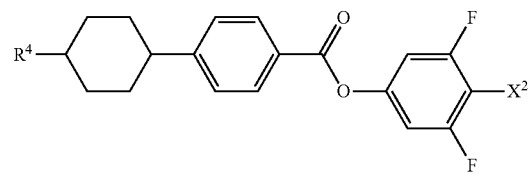
(5-50)
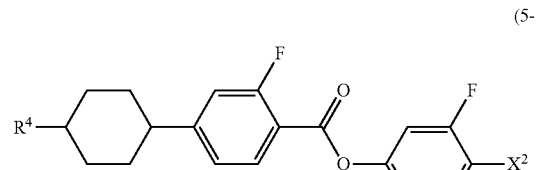
(5-51)
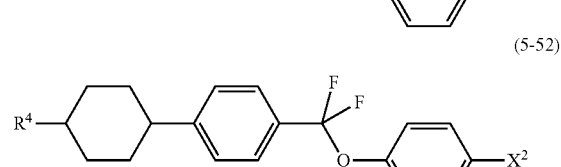
(5-52)
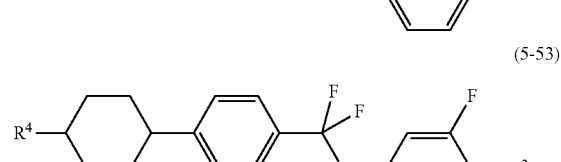
(5-53)
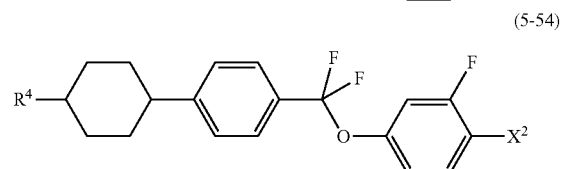
(5-54)
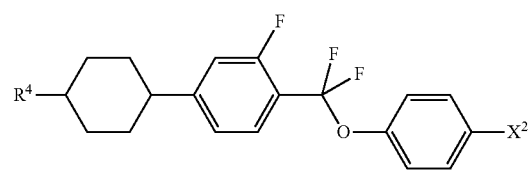
(5-55)

-continued

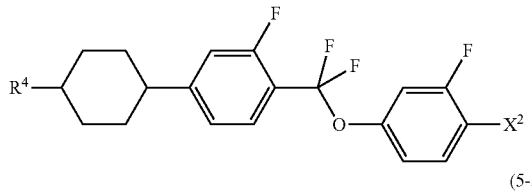
(5-56)

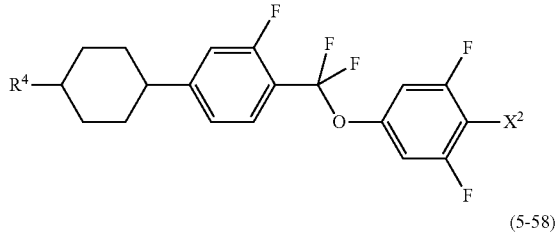
(5-57)

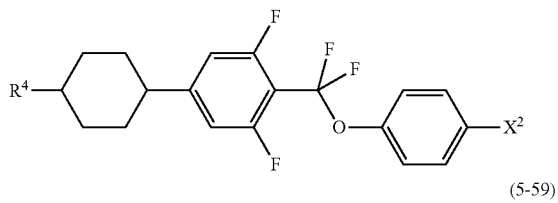
(5-58)

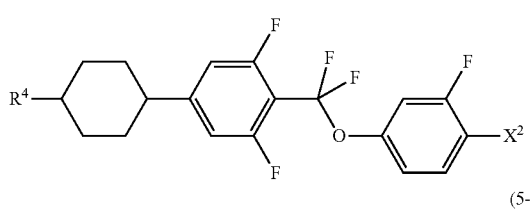
(5-59)

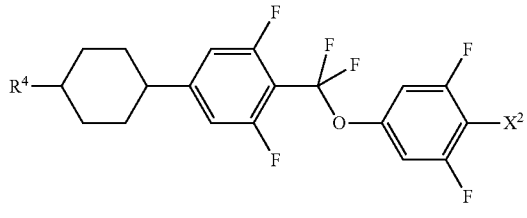
(5-60)

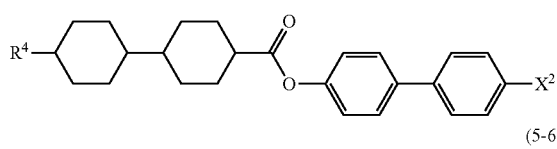
(5-61)

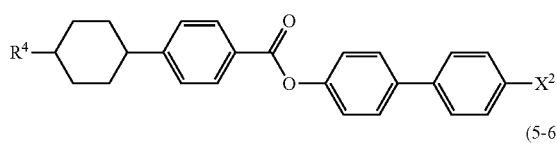
(5-62)

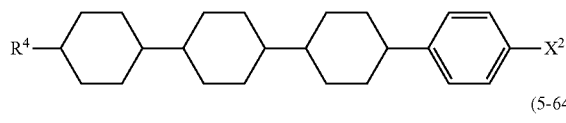
(5-63)

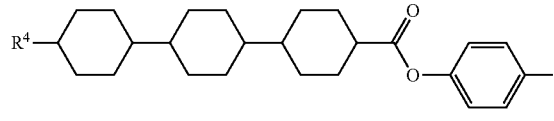
(5-64)

In the formula, the definitions of $R^4$ and $X^2$ are just the same as described previously.

The compound (5), that is the component C, is mainly used in the preparation of the liquid crystal composition for use in STN, TN and PSA mode-devices, since the dielectric anisotropy is positive and the value is quite large. The threshold voltage of the composition can be decreased by the addition of the component C. The viscosity can be adjusted, the refractive index anisotropy can be adjusted, and the temperature range of a liquid crystal phase can be increased. Furthermore, the component C can be utilized for an improvement of the steepness.

The content of the component C is suitably in the range of approximately 0.1% to approximately 99.9% by weight, preferably in the range of approximately 10% to approximately 97% by weight, and more preferably in the range of approximately 40% to approximately 95% by weight in the preparation of the liquid crystal composition for use in a STN or TN mode-device. The threshold voltage, the temperature range of a liquid crystal phase, the refractive index anisotropy, the dielectric anisotropy, the viscosity and so forth can be adjusted by the addition of a component which will be described below.

The compounds (6) to (11), that is the component D, are desirable in the preparation of the liquid crystal composition having negative dielectric anisotropy for use in a vertical alignment (VA) mode-device, a polymer sustained alignment (PSA) mode-device and so forth.

Desirable examples of the compounds (6) to (11) (the component D) include the compounds (6-1) to (6-6), the compounds (7-1) to (7-15), the compounds (8-1), the compounds (9-1) to (9-3), the compounds (10-1) to (10-11) and the compounds (11-1) to (11-10).

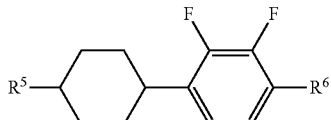
(6-1)

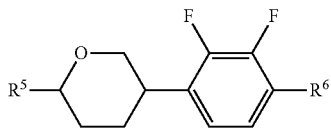
(6-2)

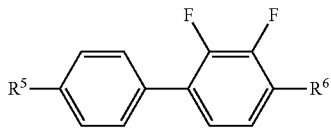
(6-3)

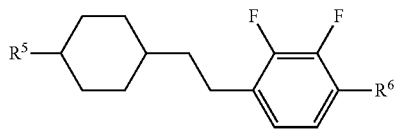
(6-4)

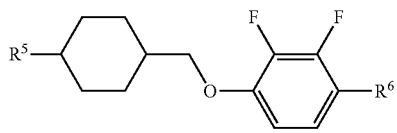
(6-5)

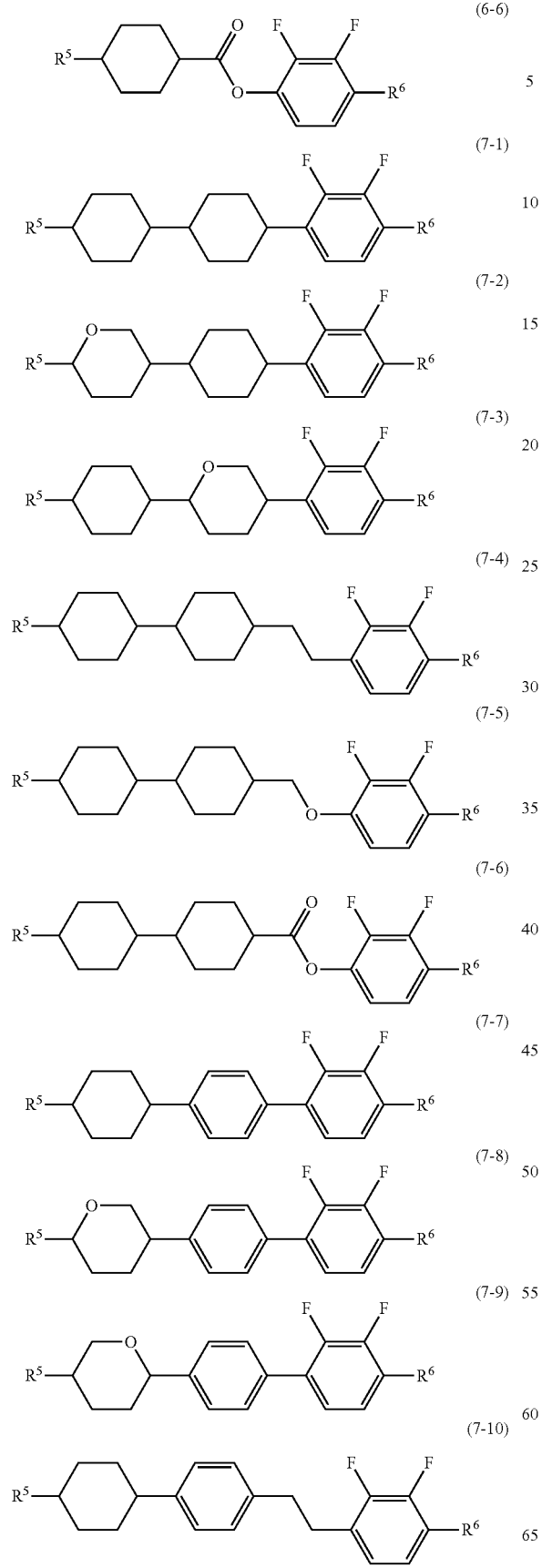

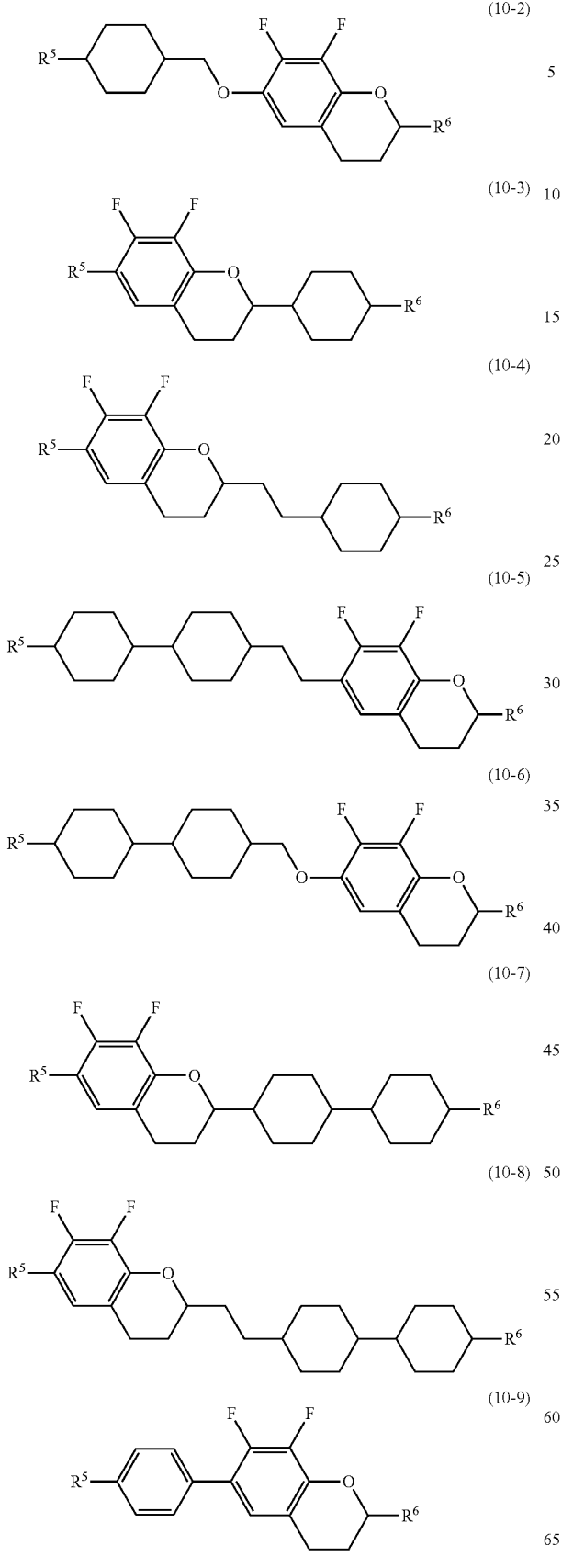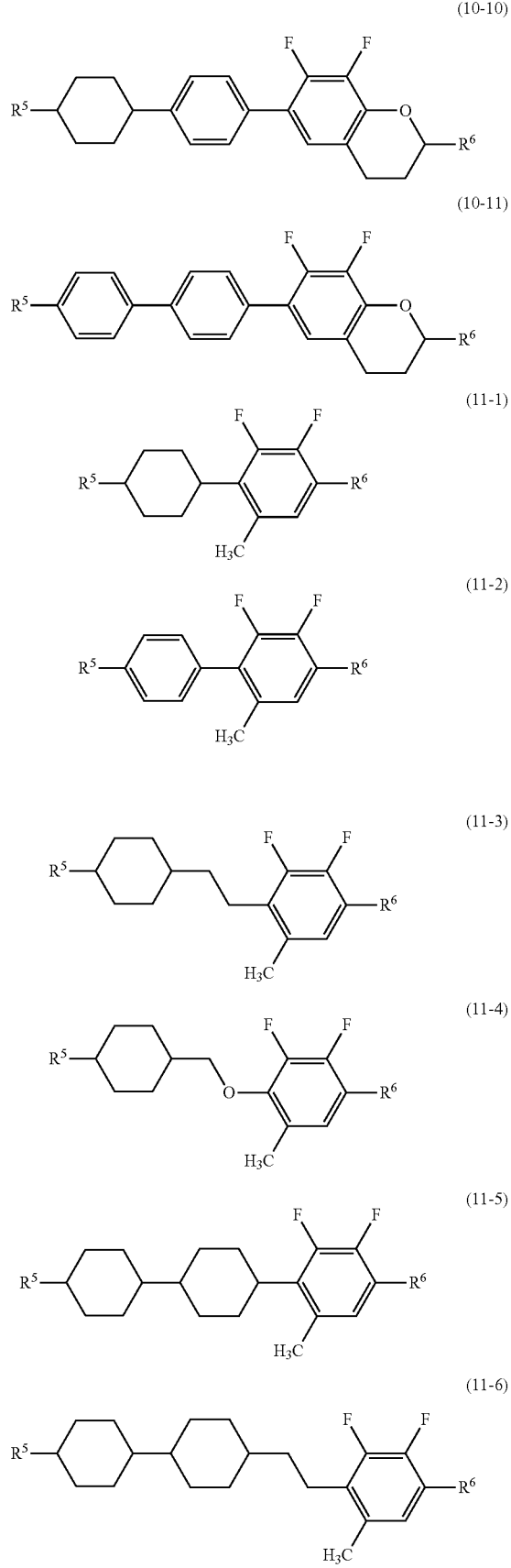

-continued

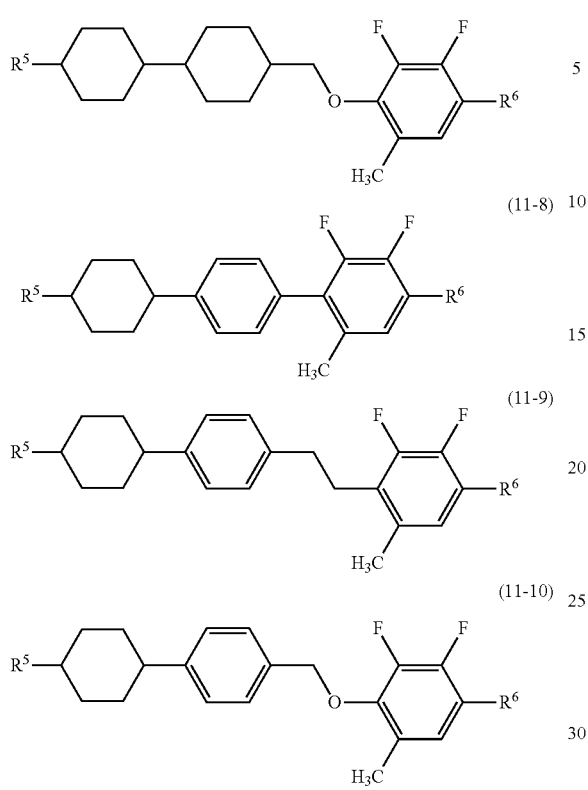

In the formula, the definitions of R[5] and R[6] are just the same as described previously.

The compounds of the component D are mainly used in the liquid crystal composition having negative dielectric anisotropy for use in a VA mode-device and a PSA mode-device. As the content of the component D is increased, the threshold voltage of the composition decreases, however, the viscosity increases. Accordingly, it is desirable that the content of the component D decreases as long as the required value of the threshold is satisfied. It is desirable that the content is 40% by weight or more in order to ensure sufficient voltage drive, since the absolute value of the dielectric anisotropy is about 5.

The compound (6) among the component D is effective mainly in adjusting the threshold voltage, adjusting the viscosity, or adjusting the refractive index anisotropy, since it is a two-ring compound. The compounds (7) and (8) are effective in increasing the clearing point, increasing the temperature range of a nematic phase, decreasing the threshold voltage or increasing the optical anissotropy for instance, since it is a three-ring compound. The compounds (9), (10) and (11) are effective in decreasing the threshold voltage for instance.

The content of the component D is preferably in the range of approximately 40% to approximately 99% by weight, and more preferably in the range of approximately 50% to approximately 95% by weight based on the total weight of the composition, in the preparation of the composition for use in a VA and PSA mode-device. The elastic constant can be adjsuted and the voltage-transmission curve can be adjsuted by the addition of the component D. It is desirable that the content of the component D is approximately 30% by weight or less based on the total weight of the composition when the component D is added to a composition having positive dielectric anisotropy.

Desirable examples of the compounds (12), (13) and (14) (the component E) include the compounds (12-1) to (12-11), the compounds (13-1) to (13-19) and the compounds (14-1) to (14-6).

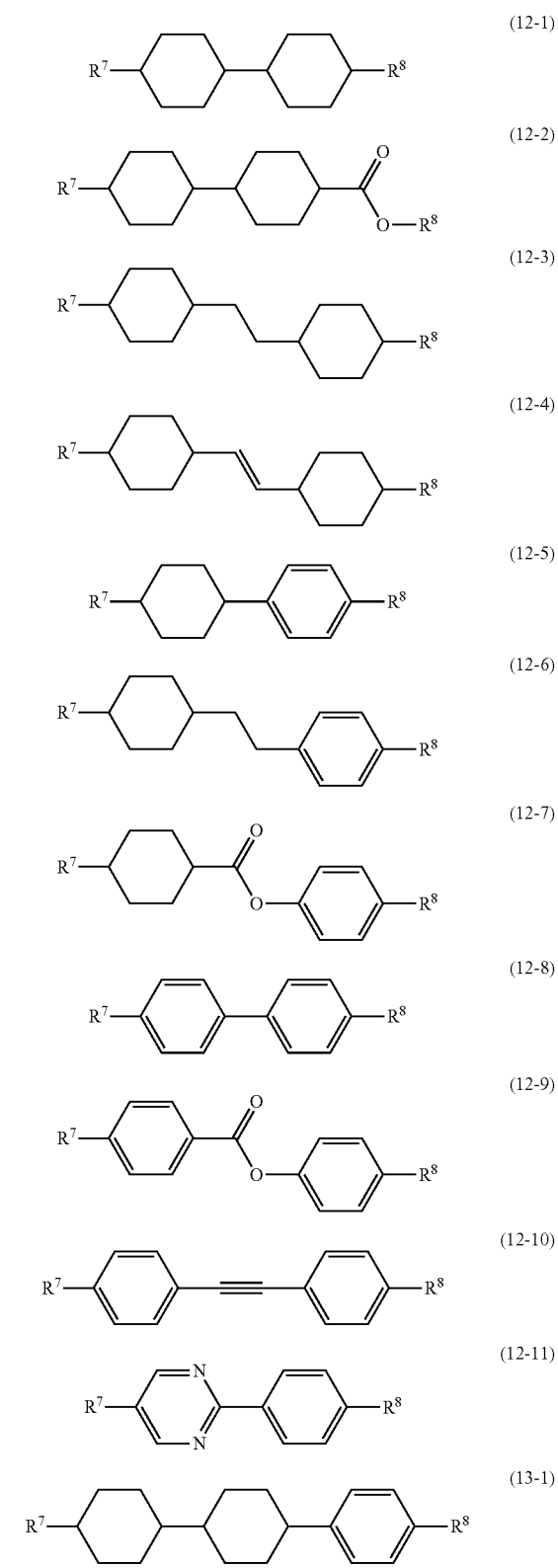

(13-2)
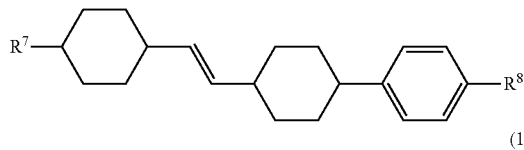
(13-3)
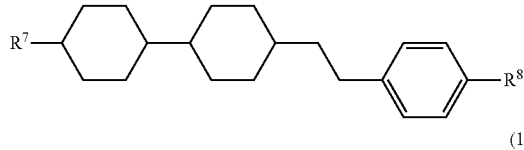
(13-4)
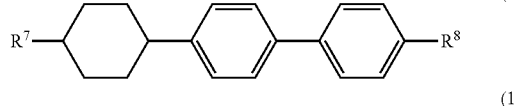
(13-5)
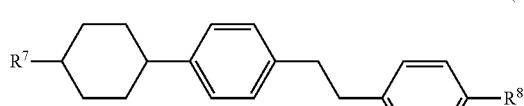
(13-6)
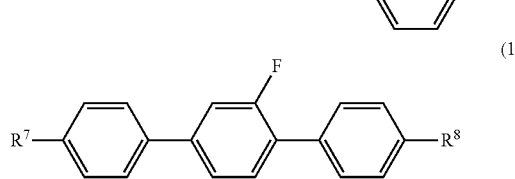
(13-7)
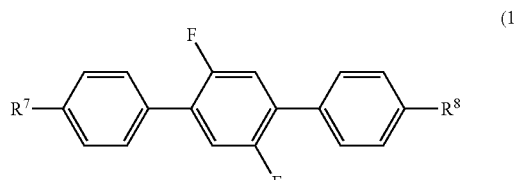
(13-8)
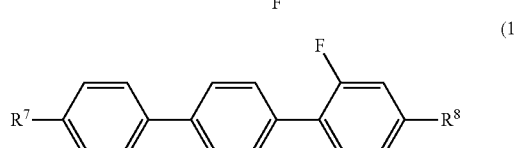
(13-9)
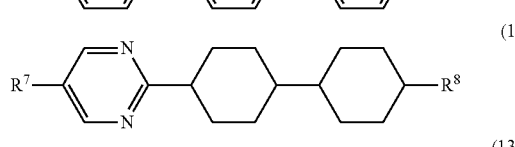
(13-10)
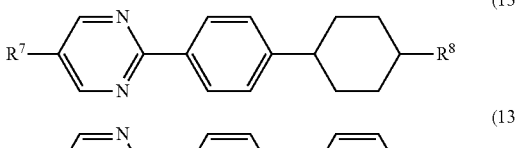
(13-11)
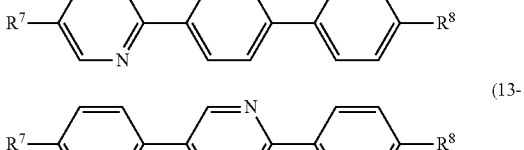
(13-12)
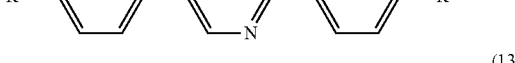
(13-13)
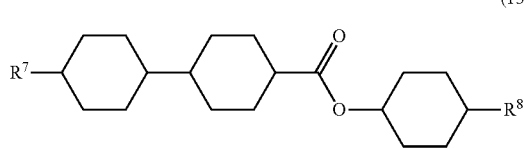
(13-14)
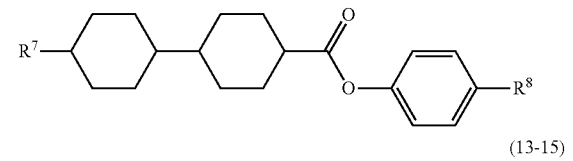
(13-15)
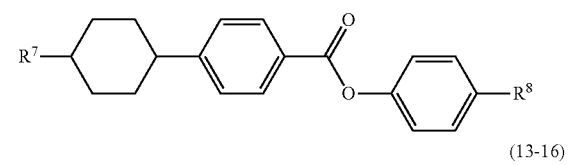
(13-16)
(13-17)
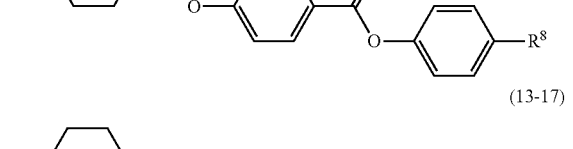
(13-18)
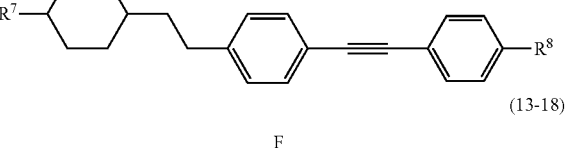
(13-19)
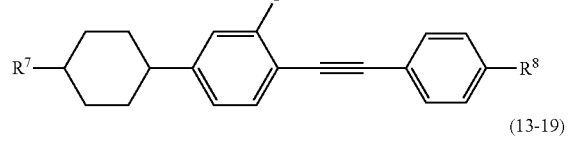
(14-1)
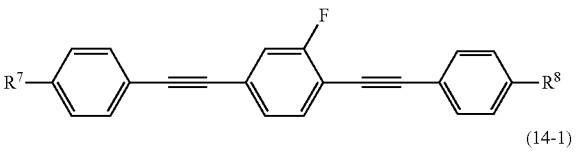
(14-2)
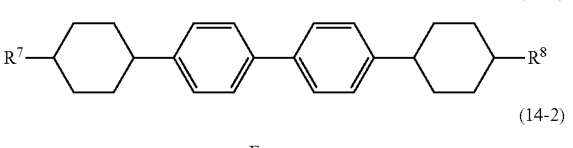
(14-3)
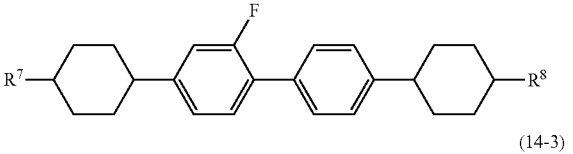
(14-4)
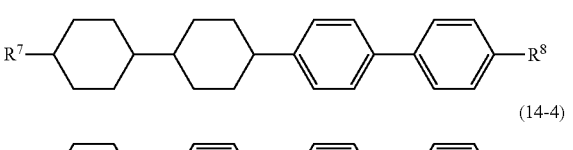
(14-5)
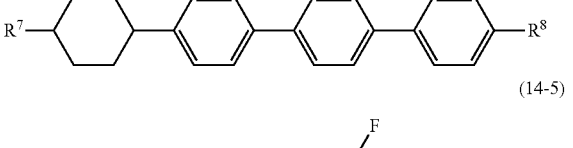

-continued (14-6)

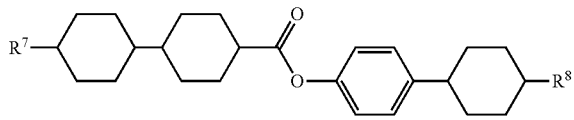

In the formula, the definitions of $R^7$ and $R^8$ are just the same as described previously.

The compounds (12) to (14) (the component E) are close to neutral, since the absolute value of the dielectric anisotropy is small. The compound (12) is effective mainly in adjusting the viscosity or adjusting the refractive index anisotropy, and the compounds (13) and (14) are effective in increasing the temperature range of a nematic phase that is caused by an increase in the clearing point for instance, or adjusting the refractive index anisotropy.

As the content of the component E is increased, the threshold voltage of the liquid crystal composition increases, however, the viscosity decreases. Accordingly, it is desirable that the content increases as long as the required value of the threshold voltage of the liquid crystalliquid crystal composition is sasified. The content of the component E is preferably approximately 30% by weight or more, and more preferably approximately 50% by weight or more based on the total weight of the composition, in the preparation of the liquid crystal composition for use in a TFT or PSA mode-device. The content of the component E is preferably approximately 30% by weight or more, and more preferably approximately 40% by weight or more based on the total weight of the composition, in the preparation of the liquid crystal composition for use in a TN, STN or PSA mode-device.

It is desirable that the liquid crystal composition of the invention includes at least one compound selected from the compound (1) in the range of approximately 0.1% to approximately 99% by weight for exhibiting excellent characteristics.

The liquid crystal composition of the invention is generally prepared according to known methods such as the mutual dissolution of necessary components at a high temperature. An additive that is well-known to a person skilled in the art may be added to the composition depending on its intended use. For example, a liquid crystal composition including an optically active compound, or including a polymerizable compound and a polymerization initiator, those of which will be described below, or a liquid crystal composition for use in a GH mode-device, to which a dye is added, can be prepared. The additive is generally well known to a person skilled in the art, and is described in the literature and so forth in detail. An additive such as an antioxidant, an ultraviolet light absorber or an antifoaming agent may be added to the liquid crystal composition.

The liquid crystal composition of the invention may further include at least one optically active compound. A known chiral dopant is added as an optically active compound. The chiral dopant is effective in inducing a helical structure in liquid crystals, adjusting a necessary twist angle and thus preventing a reverse twist. Examples of the chiral dopant include the following optically active compounds (Op-1) to (Op-13).

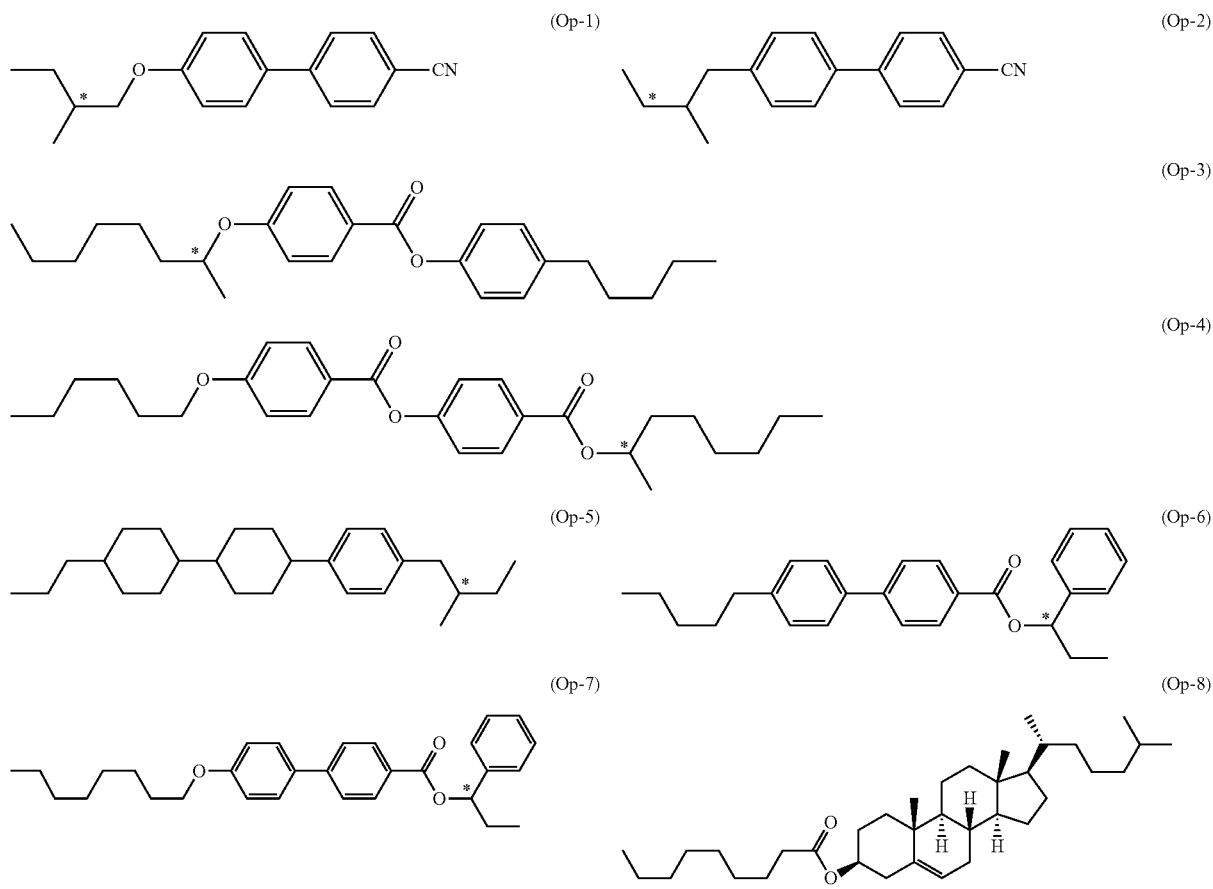

-continued

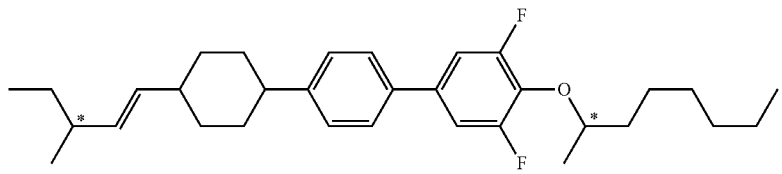
(Op-9)

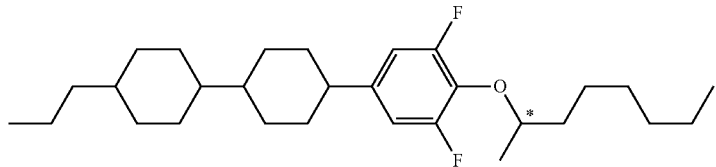
(Op-10)

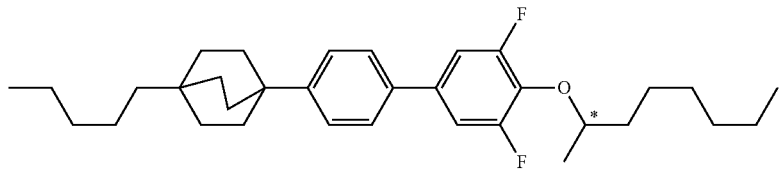
(Op-11)

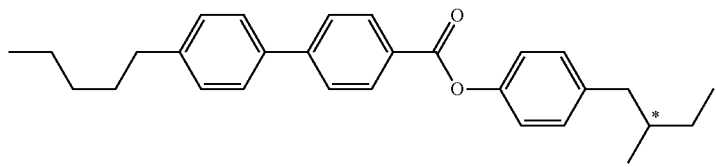
(Op-12)

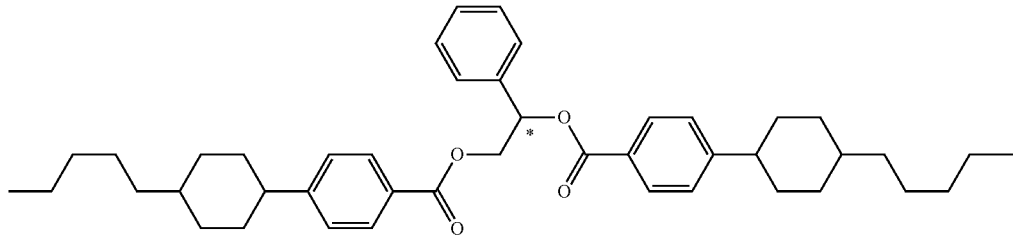
(Op-13)

A helical pitch is usually adjusted by the addition of this optically active compound to the liquid crystal composition of the invention. It is desirable to adjust the helical pitch to the range of approximately 40 micrometers to approximately 200 micrometers in a liquid crystal composition for use in TFT and TN mode-devices. It is desirable to adjust the helical pitch to the range of approximately 6 micrometers to approximately 20 micrometers in a liquid crystal composition for use in a STN mode-device. It is desirable to adjust the helical pitch to the range of approximately 1.5 micrometers to approximately 4 micrometers for use in a bistable twisted nematic (BTN) mode-device. Two or more optically active compounds may be added for the purpose of adjusting the temperature dependence of the helical pitch.

The liquid crystal composition of the invention can be used for a GH mode-device by the addition of a dichroic dye such as a merocyanine, stylyl, azo, azomethine, azoxy, quinophthalone, anthraquinone or tetrazine compound.

The liquid crystal composition of the invention can be used for a NCAP-device prepared by micro-encapsulating nematic liquid crystals, and for a polymer-distributed liquid crystal display device (PDLCD) prepared by forming a three-dimensional network polymer in liquid crystals, such as a polymer network liquid crystal display device (PNLCD), and also for an electrically controlled birefringence (ECB) mode-device or a DS mode-device.

The liquid crystal composition of the invention can be used as a liquid crystal composition for a polymer sustained alignment (PSA) mode-device by the addition of a polymerizable compound. Examples of the polymerizable compound include compounds having polymerizable groups such as acrylates, methacrylates, vinyl compounds, vinyloxy compounds, propenyl ethers, epoxy compounds (oxiranes, oxetanes) and vinyl ketones. The polymerizable compound is polymerized on irradiation with ultraviolet light or the like, preferably in the presence of a suitable initiator such as a photopolymerization initiator. Suitable conditions for the polymerization, and a suitable type and a suitable amount of the initiator are known to a person skilled in the art and are described in the literature. For example, Irgacure 651 (registered trademark), Irgacure 184 (registered trademark) or Darocure 1173 (registered trademark) (Ciba Geigy AG), each of which is a photo-initiator, is suitable for radical polymerization.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be explained below in more detail by way of examples. The invention is not limited to the examples. The term "%" means "% by weight," unless otherwise noted. First, the method for analysis will be explained, since the obtained compounds herein were identified by means of $^1$H-NMR spectroscopy and so forth.

$^1$H-NMR Analysis:

A model DRX-500 apparatus (made by Bruker BioSpin Corporation) was used for measurement. A sample prepared in Examples and so forth was dissolved in a deuterated solvent such as $CDCl_3$ in which the sample was soluble, and the measurement was carried out under the conditions of room temperature, 500 MHz and twenty-four times of accumulation. Tetramethylsilane (TMS) was used as the standard reference material for the zero point of the chemical shift.

GC Analysis:

A Gas Chromatograph Model GC-14B made by Shimadzu Corporation was used for measurement. A capillary column CBP1-M25-025 (length 25 m, bore 0.22 mm, film thickness 0.25 micrometer; dimethylpolysiloxane as a stationary liquid phase; non-polar) made by Shimadzu Corporation was used. Helium was used as a carrier gas, and its flow rate was adjusted to 1 ml per minute. The temperature of the sample injector was set at 280° C. and the temperature of the detector (FID) was set at 300° C.

A sample was dissolved in toluene to give a 1% by weight solution, and then 1 microliter of the resulting solution was injected into the sample injector.

Chromatopac Model C—R6A made by Shimadzu Corporation or its equivalent was used as a recorder. The resulting gas chromatogram showed the retention time of the peaks and the values of the peak areas corresponding to the component compounds.

Chloroform or hexane, for example, may also be used as a solvent for diluting the sample. The following capillary columns may also be used: DB-1 (length 30 m, bore 0.32 mm, film thickness 0.25 micrometer) made by Agilent Technologies Inc., HP-1 (length 30 m, bore 0.32 mm, film thickness 0.25 micrometer) made by Agilent Technologies Inc., Rtx-1 (length 30 m, bore 0.32 mm, film thickness 0.25 micrometer) made by Restek Corporation, BP-1 (length 30 m, bore 0.32 mm, film thickness 0.25 micrometer) made by SGE International Pty. Ltd, and so forth.

The ratio of the peak areas in the gas chromatogram corresponds to the ratio of component compounds. In general, the percentage by weight of each component compound in an analytical sample is not completely the same as the percentage of each peak area in the analytical sample. In the invention, however, the percentage by weight of the component compound in the analytical sample corresponds substantially to the percentage of the peak area in the analytical sample, because the correction coefficient is essentially 1 (one) when the columns described above are used.

Samples for Measurement

Two kinds of samples are used for measuring physical properties of a compound: one is the compound itself, and the other is a mixture of the compound and mother liquid crystals.

In the latter case using a sample in which a compound is mixed with mother liquid crystals, the measurement is carried out according to the following method. First, the sample is prepared by mixing 15% by weight of the compound and 85% by weight of the mother liquid crystals. Then, extrapolated values are calculated from the measured values of the resulting sample by means of an extrapolation method based on the following formula. The extrapolated values are regarded as physical properties of this compound.

[Extrapolated value]=(100×[Measured value of sample]−[% by weight of mother liquid crystals]×[Measured value of mother liquid crystals])/[% by weight of compound]

When a smectic phase or crystals deposited even at this ratio of the compound to the mother liquid crystals at 25° C., the ratio of the to the mother liquid crystals was changed in the order of (10% by weight: 90% by weight), (5% by weight: 95% by weight) and (1% by weight: 99% by weight). Physical properties of the sample were measured at the ratio in which the smectic phase or the crystals did not deposit at 25° C. Extrapolated values were determined according to the above equation, and were regarded as physical properties of the compound.

There are a variety of mother liquid crystals used for measurement and, for example, the formulation of the mother liquid crystals (A) is shown below.

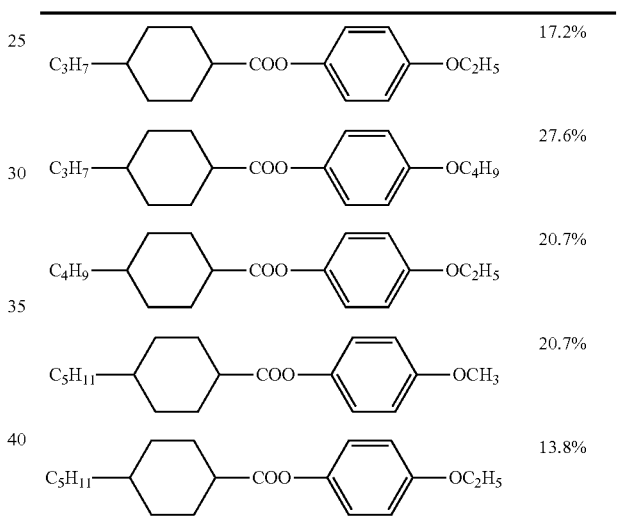

Incidentally, in the case where physical properties of a liquid crystal composition were measured, the liquid crystal composition itself was used as a sample.

Methods of Measurement

Physical properties of compounds were measured according to the following methods. Most of the measurement methods are those described in the Standard of Electronic Industries Association of Japan, EIAJ-ED-2521A, or the modified methods. No TFT was attached to a TN device or a VA device used for measurement.

When a compound itself or a liquid crystal compound composition itself was employed as a sample, a measured value itself was described here. When a sample was prepared by mixing the compound with mother liquid crystals, a value calculated from a measured value according to the extrapolation method was regarded as the value of physical properties.

Phase Structure and Transition Temperature (° C.):

Measurements were carried out according to the following methods (1) and (2).

(1) A compound was placed on a hot plate of a melting point apparatus (Hot Stage Model FP-52 made by Mettler Toledo International Inc.) equipped with a polarizing microscope, and the phase conditions and their changes were observed with the polarizing microscope while the compound was heated at the rate of 3° C. per minute, and the kinds of phase were specified.

(2) A sample was heated and then cooled at a rate of 3° C. per minute using a Perkin-Elmer differential scanning calorimeter, a DSC-7 System or a Diamond DSC System. The starting point of an endothermic peak or an exothermic peak caused by a phase change of the sample was obtained by means of the extrapolation, and thus the phase transition temperature was determined.

Hereinafter, the symbol C stood for crystals, which were expressed by $C_1$ or $C_2$ when the kinds of crystals were distinguishable. The symbols S and N stood for a smectic phase and a nematic phase, respectively. The symbol Iso stood for a liquid (isotropic). When a smectic B phase and a smectic A phase were distinguishable in the smectic phases, they were expressed as $S_B$ and $S_A$, respectively. Phase transition temperatures were expressed, for example, as "C 50.0 N 100.0 Iso", which means that the phase transition temperature from crystals to a nematic phase (CN) is 50.0° C., and the phase transition temperature from the nematic phase to a liquid (NI) is 100.0° C. The same applied to the other transition temperatures.

Maximum Temperature of a Nematic Phase ($T_{NI}$; ° C.):

A sample (a liquid crystal composition, or a mixture of a liquid crystal compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. A maximum temperature meant a temperature measured when part of the sample began to change from a nematic phase to an isotropic liquid. Hereinafter, the maximum temperature of a nematic phase may simply be abbreviated to "maximum temperature."

Minimum Temperature of a Nematic Phase (Tc; ° C.):

A sample having a nematic phase was put in glass vials and then kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., Tc was expressed as <−20° C. A lower limit of the temperature range of a nematic phase may simply be abbreviated to "the minimum temperature."

Compatibility at a Low Temperature:

Samples were prepared by mixing a compound with mother liquid crystals so that the amount of the compound became 20% by weight, 15% by weight, 10% by weight, 5% by weight, 3% by weight and 1% by weight, and placed in glass vials. After these glass vials had been kept in a freezer at −10° C. or −20° C. for a certain period of time, they were observed as to whether or not crystals or a smectic phase had been deposited.

Viscosity (bulk viscosity; η; measured at 20° C.; mPa·s)

An E-type viscometer was used for measurement. Incidentally, as viscosity is decreased, response time decreases.

Viscosity (rotational viscosity; γ1; measured at 25° C.; mPa·s)

Rotational viscosity was measured according to the method described in M. Imai, et al., Molecular Crystals and Liquid crystals, vol. 259, p. 37 (1995). A sample (a liquid crystal composition, or a mixture of a compound and mother liquid crystals) was put in a VA device in which the distance between the two glass substrates (cell gap) was 20 micrometers. A voltage in the range of 30 V to 50 V was applied stepwise with an increment of 1 volt to the device. After a period of 0.2 second with no voltage, a voltage was applied repeatedly under the conditions of only one rectangular wave (rectangular pulse; 0.2 second) and no voltage (2 seconds). The peak current and the peak time of the transient current generated by the applied voltage were measured. The value of rotational viscosity was obtained from the measured values and the calculating equation (8) on page 40 of the paper presented by M. Imai, et al. Incidentally, the value of the dielectric anisotropy ($\Delta\in$) necessary for the present calculation was obtained by the method described below, under the heading "Dielectric Anisotropy."

Refractive Index Anisotropy (Δn; measured at 25° C.)

Measurement was carried out using an Abbe refractometer with a polarizing plate attached to the ocular, on irradiation with light at a wavelength of 589 nm at 25° C. The surface of the main prism was rubbed in one direction, and then a sample (a liquid crystal composition, or a mixture of a compound and mother liquid crystals) was dropped onto the main prism. A refractive index (n∥) was measured when the direction of the polarized light was parallel to that of the rubbing. A refractive index (n⊥) was measured when the direction of polarized light was perpendicular to that of the rubbing. The value of the refractive index anisotropy was calculated from the equation: Δn=n∥−n⊥.

Dielectric Anisotropy ($\Delta\in$; Measured at 25° C.)

An ethanol (20 mL) solution of octadecyltriethoxysilane (0.16 ml) was applied to a well-washed glass substrate. The glass substrate was rotated with a spinner, and then heated at 150° C. for 1 hour. A VA device in which the distance (cell gap) was 20 micrometers was assembled from the two glass substrates.

A polyimide alignment film was prepared on glass substrates in a similar manner. After a rubbing-treatment to the alignment film formed on the glass substrates, a TN device in which the distance between the two glass substrates was 9 micrometers and the twist angle was 80 degrees was assembled.

A sample (a liquid crystal composition, or a mixture of a compound and mother liquid crystals) was put in the VA device obtained, a voltage of 0.5 V (1 kHz, sine waves) was applied to the sample, and then the dielectric constant ($\in\parallel$) in the major axis direction of the liquid crystal molecules was measured.

The sample (the liquid crystal composition, or the mixture of the compound and the mother liquid crystals) was put in the TN device obtained, a voltage of 0.5 V (1 kHz, sine waves) was applied to the sample, and then the dielectric constant ($\in\perp$) in the minor axis direction of the liquid crystal molecules was measured.

The value of the dielectric anisotropy was calculated from the equation of $\Delta\in=\in\parallel-\in\perp$.

Threshold Voltage (Vth; Measured at 25° C.; V):

Measurement was carried out with an LCD evaluation system Model LCD-5100 made by Otsuka Electronics Co., Ltd. The light source was a halogen lamp. A sample was poured into a VA device having a normally black mode, in which the distance between the two glass substrates (cell gap) was 4 micrometers and the rubbing direction was antiparallel, and then the device was sealed with an adhesive curable on irradiation with ultraviolet light. A voltage to be applied to the device (60 Hz, rectangular waves) was stepwise increased in 0.02 V increments from 0 Vup to 20 V. During the increase, the device was irradiated with light in the perpendicular direction, and the amount of light passing through the device was measured. A voltage-transmittance curve was prepared, in which the maximum amount of light corresponded to 100% transmittance and the minimum amount of light corresponded to 0% transmittance. The threshold voltage was a voltage at 10% transmittance.

Synthetic Example of the Compound

Example 1

Preparation of 1-(3-butylcyclopentyl)-4-ethoxy-2,3-difluorobenzene (The Compound No. 45)

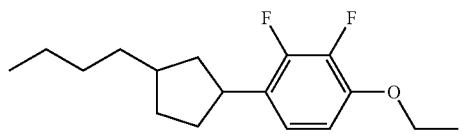 [SMILES: CCCCC1CCC(c2ccc(OCC)c(F)c2F)C1]

First Step:

Diethyl ether (800 ml) and tributylphosphine (83 ml) were added to copper iodide (41.4 g) in a reaction vessel under an atmosphere of nitrogen, and the mixture was cooled to −78° C., and then n-butyllithium (1.65 M, a hexane solution) (19 ml) was added dropwise at a temperature of −70° C. or lower. The stirring was continued at −78° C. for 20 minutes, and 2-cyclopentene-1-one (17.0 g) in a diethyl ether (150 ml) solution was added dropwise at a temperature of −70° C. or lower. After the mixture had been stirred at −78° C. for another 20 minutes, it was warmed to −40° C., and stirred for another 2.5 hours. Then, a saturated aqueous solution of ammonium chloride (600 ml) was added at −40° C., and the mixture was warmed to room temperature. The mixture was separated, and the water layer was extracted with diethyl ether three times, and then the combined organic layer was washed with brine. The solution was dried over anhydrous magnesium sulfate and the solvent was distilled off under reduced pressure. The residue was purified by silica gel chromatography (eluent: ethyl acetate/n-heptane=1/20 by volume) to give 3-butyl-cyclopentanone (15.4 g).

Second Step:

THF (40 ml) was added to 1-bromo-4-ethoxy-2,3-difluorobenzene (3.56 g) in a reaction vessel under an atmosphere of nitrogen, and the mixture was cooled to −78° C. n-Butyllithium (1.65 M, in a hexane solution) (9.1 ml) was added dropwise at a temperature of −70° C. or lower. The stirring was continued at −78° C. for another 1.5 hour and 3-butyl-cyclopentanone (2.1 g) obtained in the first step, in a THF (20 ml) solution was added dropwise at a temperature of −70° C. or lower. After the mixture had been stirred at −78° C. for another 1 hour, it was warmed to room temperature, and a saturated aqueous solution of ammonium chloride (50 ml) was added. The mixture was separated, and the water layer was extracted with diethyl ether three times, and then the combined organic layer was washed with brine. The solution was dried over anhydrous magnesium sulfate and the solvent was distilled off under reduced pressure. The residue was purified by silica gel chromatography (eluent: ethyl acetate/n-heptane=1/9 by volume) to give 3-butyl-1-(4-ethoxy-2,3-difluorophenyl)cyclopentanol (2.8 g).

Third Step:

Toluene (50 ml) and p-toluenesulfonic acid monohydrate (0.14 g) were added to 3-butyl-1-(4-ethoxy-2,3-difluorophenyl)cyclopentanol (2.8 g) obtained in the second step, in a reaction vessel equipped with a Dean-Stark apparatus under an atmosphere of nitrogen. The mixture was refluxed for 30 minutes, while forming water was removed with a Dean-Stark apparatus. The reaction solution was cooled to room temperature and was washed with water. The solution was dried over anhydrous magnesium sulfate and the solvent was distilled off under reduced pressure. The residue was purified by silica gel chromatography (eluent: ethyl acetate/n-heptane=1/9 by volume) to give a mixture (2.4 g) of 1-(3-butylcyclopent-1-enyl)-4-ethoxy-2,3-difluorobenzene and 1-(4-butylcyclopent-1-enyl)-4-ethoxy-2,3-difluorobenzene.

Fourth Step:

Solmix A-11 (10 ml) and Pd/C (E type) (0.025 g) were added to a mixture obtained in the third step, of 1-(3-butylcyclopent-1-enyl)-4-ethoxy-2,3-difluorobenzene and 1-(4-butylcyclopent-1-enyl)-4-ethoxy-2,3-difluorobenzene in a reaction vessel. The mixture was stirred at room temperature under a hydrogen atmosphere until hydrogen absorption had ceased. After the completion of the reaction, Pd/C was removed and the solvent was distilled off. The residue was purified by silica gel chromatography (eluent: ethyl acetate/n-heptane=1/4 by volume) and then purified by recrystallization (solvent; Solmix A-11/n-heptane=5/1 by volume) to give 1-(3-butylcyclopentyl)-4-ethoxy-2,3-difluorobenzene (1.2 g).

The chemical shift (δ; ppm) in $^1$H-NMR analysis was described below, and the resulting compound was identified as 1-(3-butylcyclopentyl)-4-ethoxy-2,3-difluorobenzene. The solvent for measurement was $CDCl_3$.

Chemical shift (δ; ppm): 6.87 (m, 1H), 6.65 (m, 1H), 4.09 (q, 2H), 3.19 (m, 1H), 2.14 (m, 1H), 2.07-1.85 (m, 3H), 1.61 (m, 1H), 1.43 (t, 3H), 1.41-1.24 (m, 7H), 1.19 (q, 1H) and 0.90 (t, 3H).

The phase transition temperature of the resulting compound No. 45 was as follows: Phase transition temperature: C 28.0 C' 35.8 Iso.

A sample was prepared by mixing 15% by weight of the compound and 85% by weight of the mother liquid crystals (A), and the physical properties were calculated from the values obtained by measurement according to the extrapolation method. The physical properties of this compound were that NI=−110.7° C.; Δ∈=−2.7; Δn=−0.011; η=33.4; mPa·s; and $V_{th}$=2.28.

Example 2

Preparation of 4'-(3-butylcyclopentyl)-4-ethoxy-2,3-difluorobiphenyl (The Compound No. 146)

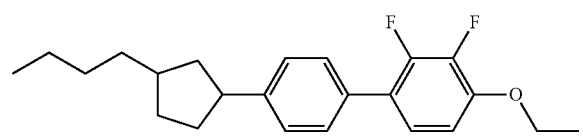 [SMILES: CCCCC1CCC(c2ccc(-c3ccc(OCC)c(F)c3F)cc2)C1]

4'-(3-Butylcyclopentyl)-4-ethoxy-2,3-difluorobiphenyl was prepared in the same manner as in Example 1, except that 4'-bromo-4-ethoxy-2,3-difluorobiphenyl was used instead of 1-bromo-4-ethoxy-2,3-difluorobenzene in the second step in Example 1.

The chemical shift (δ; ppm) in $^1$H-NMR analysis was described below, and the resulting compound was identified as 4'-(3-butylcyclopentyl)-4-ethoxy-2,3-difluorobiphenyl. The solvent for measurement was $CDCl_3$.

Chemical shift δ (ppm); 7.42 (d, 2H), 7.30 (d, 2H), 7.08 (m, 1H), 6.78 (m, 1H), 4.15 (q, 2H), 3.07 (m, 1H), 2.22 (m, 1H), 2.14-1.85 (m, 3H), 1.70 (m, 1H), 1.48 (t, 3H), 1.45-1.20 (m, 7H), 1.19 (q, 1H) and 0.90 (t, 3H).

The phase transition temperature of the resulting compound No. 146 was as follows: Phase transition temperature: C 38.5 (N 21.0) Iso.

A sample was prepared by mixing 15% by weight of the compound and 85% by weight of the mother liquid crystals (A), and the physical properties were calculated from the values obtained by measurement according to the extrapolation method. The physical properties of this compound were that NI=25.9° C.; Δ∈=−5.3; Δn=−0.135; η=60.4; mPa·s; and $V_{th}$=2.71.

Example 3

Preparation of 1-(3-propylcyclopentyl)-4-vinylcyclohexane (The Compound No. 1)

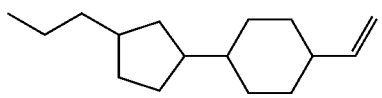 [SMILES: C=CC1CCC(C2CCC(CCC)C2)CC1]

First Step:

THF (100 ml) was added to methoxymethyltriphenylphophnium chloride (29.3 g) in a reaction vessel under an atmosphere of nitrogen, and the solution was cooled to −15° C. t-BuOK (10.5 g) in a THF (50 ml) solution was added, and the stirring was continued for another 1 hour. 4-(3-Propylcyclopentyl)-cyclohexanone (15.0 g) in a THF (50 ml) solution was added dropwise, and the stirring was continued for another 2 hours. The reaction mixture was warmed to room temperature and was extracted with toluene after the addition of water (200 ml) The resulting organic layer was washed with water and dried over anhydrous sulfate, and the toluene was concentrated to a volume of about 100 ml under reduced pressure. The concentrate was poured into n-hexane (500 ml) and solids deposited were filtered off. The solvent of the resulting solution was distilled off under reduced pressure, and the residue was purified by silica gel chromatography (eluent: ethyl acetate/n-heptane=1/9 by volume) to give 1-methoxymethylene-4-(3-propylcyclopentyl)cyclohexane (17.0 g).

Second Step:

Hydrochrolic acid (1 M) (30 ml) was added to 1-methoxymethylene-4-(3-propylcyclopentyl)cyclohexane (17.0 g) obtained in the first step, which was dissolved in (200 ml), and the mixture was stirred at room temperature for 2 hours. Water (100 ml) was added to the mixture, which was extracted with toluene. The combined organic layer was washed with water and dried over anhydrous magnesium sulfate, and the solvent was distilled off under reduced pressure. Ethanol (200 ml) and toluene (50 ml) was added to the residue, and a NaOH aqueous solution (20%) (30 ml) was added under ice-cooling, and the mixture was stirred at room temperature for another 3 hours. A saturated aqueous solution of ammonium chloride was added to neutralize and the mixture was extracted with toluene. The combined organic layer was washed with water, dried over anhydrous magnesium sulfate, and the toluene was distilled off under reduced pressure. The residue was purified by silica gel chromatography (eluent: ethyl acetate/n-heptane=1/20 by volume) to give 4-(3-propylcyclopentyl)cyclohexanecarboaldehyde (15.0 g).

Third Step:

THF (50 ml) was added to methyltriphenylphosphonium bromide (6.27 g) in a reaction vessel under an atmosphere of nitrogen, and the mixture was cooled to −15° C. t-BuOK (1.97 g) in a THF (20 ml) solution was added, and the stirring was continued for another 1 hour. 4-(3-Propylcyclopentyl)-cyclohexanone-4-(3-propylcyclopentyl)cyclohexanecarboaldehyde (3.0 g) in a THF (20 ml) solution was added dropwise and the mixture was stirred for another 2 hours. The reaction mixture was warmed to room temperature and was extracted with toluene after the addition of water (50 ml). The resulting organic layer was washed with water and dried over anhydrous sulfate, and the solution was concentrated under reduced pressure to a volume of about 50 ml. The concentrate was poured into n-hexane (200 ml) and solids deposited were filtered off. The solvent of the resulting solution was distilled off under reduced pressure, and the residue was purified by silica gel chromatography (eluent: n-heptane) and then purified by means of a preparative HPLC system, Model PLC-561 made by GL Sciences Inc. to give 1-(3-propylcyclopentyl)-4-vinylcyclohexane (2.0 g).

The chemical shift (δ; ppm) in $^1$H-NMR analysis was described below, and the resulting compound was identified as 1-(3-propylcyclopentyl)-4-vinylcyclohexane. The solvent for measurement was $CDCl_3$.

Chemical shift (δ; ppm): 5.70 (m, 1H), 4.88 (d, 1H), 4.81 (d, 1H), 1.85-1.60 (m, 9H), 1.50-0.80 (m, 15H) and 0.61 (q, 1H).

The phase transition temperature of the resulting compound No. 1 was as follows: Phase transition temperature: Sm −55.8 Iso.

A sample was prepared by mixing 15% by weight of the compound and 85% by weight of the mother liquid crystals (A), and the physical properties were calculated from the values obtained by measurement according to the extrapolation method. The physical properties of this compound were that NI=−950° C.; Δ∈=−6.4; Δn=−0.063; η=−31.8; mPa·s; and $V_{th}$=1.52.

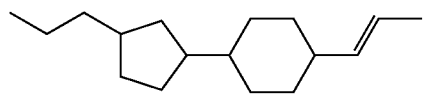

Example 4

Preparation of (E)-1-(Prop-1-enyl)-4-(3-propylcyclopentyl)cyclohexane (The Compound No. 6)

DME (1,2-dimethoxyethane; 80 ml) and 5-(ethylsulfonyl)-1-phenyl-1H-tetrazole (4.62 g) were added to 4-(3-propylcyclopentyl)cyclohexanecarboaldehyde (3.29 g) obtained in the second step in Example 3, in a reaction vessel under an atmosphere of nitrogen, and the mixture was cooled to −70° C., and then KHMDS (Potassium Hexamethyldisilazide; 20%, in a THF solution) (23.9 ml) was added dropwise. The reaction solution was warmed to room temperature, and was extracted with diethyl ether after the addition of water (50 ml) The resulting organic layer was washed with water and dried over anhydrous sulfate, and the solvent was distilled off under reduced pressure. The residue was purified by silica gel chromatography (eluent: ethyl acetate/n-heptane=1/9 by volume) and then purified by means of a preparative HPLC system, Model PLC-561 made by GL Sciences Inc. to give (E)-1-(prop-1-enyl)-4-(3-propylcyclopentyl)cyclohexane (2.0 g).

The chemical shift (δ; ppm) in $^1$H-NMR analysis was described below, and the resulting compound was identified as (E)-1-(prop-1-enyl)-4-(3-propylcyclopentyl)cyclohexane. The solvent for measurement was CDCl$_3$.

Chemical shift (δ; ppm): 5.37 (m, 2H), 1.90-0.85 (m, 28H) and 0.68 (q, 1H).

The phase transition temperature of the resulting compound No. 6 was as follows: Phase transition temperature: C −19.6 Iso.

A sample was prepared by mixing 15% by weight of the compound and 85% by weight of the mother liquid crystals (A), and the physical properties were calculated from the values obtained by measurement according to the extrapolation method. The physical properties of this compound were that NI=−69° C.; Δ∈=−5.1; Δn=−0.030; η=−23.1; mPa·s; and V$_{th}$=1.58.

Example 5

Preparation of 1-ethoxy-2,3-difluoro-4-(4-(3-propylcyclopentyl)cyclohexyl)benzene (The Compound No. 140)

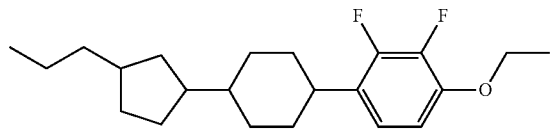 [SMILES: CCCC1CCC(C2CCC(c3ccc(OCC)c(F)c3F)CC2)C1]

First Step:

THF (100 ml) was added to 1-bromo-4-ethoxy-2,3-difluorobenzene (5.1 g) in a reaction vessel under an atmosphere of nitrogen, and the mixture was cooled to −78° C. n-Butyllithium (1.57 M, in a hexane solution) (13.8 ml) was added dropwise at a temperature of −70° C. or lower. The stirring was continued at −78° C. for another 2 hours, and 4-(3-propylcyclopentyl)-cyclohexanone (3.0 g) in a THF (10 ml) solution was added dropwise at a temperature of −70° C. or lower. After the mixture had been stirred at −78° C. for another 1 hour, it was warmed to room temperature, and a saturated aqueous solution of ammonium chloride (50 ml) was added. The mixture was separated, and the water layer was extracted with ethyl acetate three times, and then the combined organic layer was washed with brine. The solution was dried over anhydrous magnesium sulfate and the solvent was distilled off under reduced pressure. The residue was purified by silica gel chromatography (eluent: ethyl acetate/n-heptane=1/9 by volume) to give 1-(4-ethoxy-2,3-difluorophenyl)-4-(3-propylcyclopentyl)cyclohexanol (5.0 g).

Second Step:

Toluene (50 ml) and p-toluenesulfonic acid monohydrate (0.15 g) were added to 1-(4-ethoxy-2,3-difluorophenyl)-4-(3-propylcyclopentyl)cyclohexanol (5.0 g) obtained in the first step, in a reaction vessel equipped with a Dean-Stark apparatus under an atmosphere of nitrogen. The mixture was refluxed for 1.5 hour, while forming water was removed with a Dean-Stark apparatus. After the mixture had been cooled to room temperature, the reaction solution was washed with water and dried over anhydrous magnesium sulfate, and the solvent was distilled off under reduced pressure. The residue was purified by silica gel chromatography (eluent: ethyl acetate/n-heptane=1/10 by volume) to give 1-ethoxy-2,3-difluoro-4-(4-(3-propylcyclopentyl)cyclohex-1-enyl)benzene (3.9 g).

Third Step:

1-Ethoxy-2,3-difluoro-4-(4-(3-propylcyclopentyl)cyclohex-1-enyl)benzene (3.9 g) obtained in the second step, Solmix A-11 (100 ml), toluene (100 ml) and Pd/C (E type) (0.19 g) were placed in a reaction vessel, and the mixture was stirred at room temperature under a hydrogen atmosphere until hydrogen absorption had ceased. After the completion of the reaction, Pd/C was removed and the solvent was distilled off. The residue was purified by silica gel chromatography (eluent: ethyl acetate/n-heptane=1/9 by volume), and then purified by means of a preparative HPLC system, Model PLC-561 made by GL Sciences Inc. to give (1-ethoxy-2,3-difluoro-4-(4-(3-propylcyclopentyl)cyclohexyl)benzene (1.1 g).

The chemical shift (δ; ppm) in $^1$H-NMR analysis was described below, and the resulting compound was identified as 1-ethoxy-2,3-difluoro-4-(4-(3-propylcyclopentyl)cyclohexyl)benzene. The solvent for measurement was CDCl$_3$.

Chemical shift (δ; ppm): 6.83 (m, 1H), 6.66 (m, 1H), 4.08 (q, 2H), 2.73 (m, 1H), 1.95-1.70 (m, 8H), 1.45-1.05 (m, 15H), 0.89 (t, 3H) and 0.71 (q, 1H).

The phase transition temperature of the resulting compound No. 140 was as follows: Phase transition temperature: C 33.3 (SB 2.7 SA 13.4) N 37.1 Iso.

A sample was prepared by mixing 15% by weight of the compound and 85% by weight of the mother liquid crystals (A), and the physical properties were calculated from the values obtained by measurement according to the extrapolation method. The physical properties of this compound were that NI=37.3° C.; Δ∈=−4.9; Δn=−0.076; q=63.3; mPa·s; and V$_{th}$=2.57.

Example 6

Preparation of 1-ethoxy-2,3-difluoro-4-((4-(3-propylcyclopentyl)cyclohexyl)methoxy)benzene (The Compound No. 152)

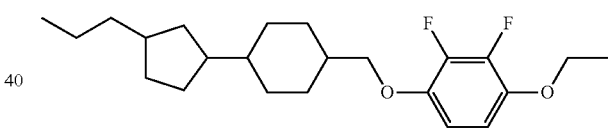

First Step:

Ethanol (30 ml) was added to 4-(3-propylcyclopentyl)cyclohexanecarboaldehyde (2.3 g) obtained in the second step in Example 3, in a reaction vessel under an atmosphere of nitrogen, and the mixture was cooled to 0° C., and sodium borohydride (0.22 g) was added slowly. After the mixture had been returned to room temperature and stirred for another 20 hours and water (30 ml) was added. The mixture was separated, and the water layer was extracted with diethyl ether three times, and then the combined organic layer was washed with brine. The solution was dried over anhydrous magnesium sulfate and the solvent was distilled off under reduced pressure. The residue was purified by silica gel chromatography (eluent: ethyl acetate/n-heptane=1/2 by volume) to give (4-(3-propylcyclopentyl)cyclohexyl)methanol (2.1 g).

Second Step:

Dichloromethane (30 ml) and p-toluenesulfonic acid chloride (1.98 g) were added to 4-(3-propylcyclopentyl)cyclohexyl)methanol (2.1 g) obtained at the first step, in a reaction vessel under an atmosphere of nitrogen, and the mixture was cooled to 0° C. Pyrimidine (1.5 ml) was added dropwise, and the mixture was warmed to room temperature. The mixture was separated after the addition of water (30 ml). The water layer was extracted with diethyl ether three times, and then the combined organic layer was washed with brine. The solution was dried over anhydrous magnesium sulfate and the solvent was distilled off under reduced pressure. The residue was purified by silica gel chromatography (eluent: ethyl acetate/n-heptane=1/2 by volume) to give 4-(3-propylcyclopentyl)cyclohexyl)methyl p-toluenesulfonic acid ester (3.3 g).

Third Step:

4-(3-Propylcyclopentyl)cyclohexyl)methyl p-toluenesulfonic acid ester (3.3 g) obtained in the second step, 4-ethoxy-2,3-difluorophenol (1.7 g), potassium carbonate (2.3 g) and DMF (20 ml) were placed in a reaction vessel, and the mixture was stirred at 70° C. for 6 hours. The mixture was cooled to room temperature, and the mixture was separated after the addition of water (20 ml). The water layer was extracted with diethyl ether three times, and then the combined organic layer was washed with brine. The solution was dried over anhydrous magnesium sulfate and the solvent was distilled off under reduced pressure. The residue was purified by silica gel chromatography (eluent: ethyl acetate/n-heptane=1/4 by volume) and then purified by recrystallization (solvent; Solmix A-11) to give 1-ethoxy-2,3-difluoro-4-((4-(3-propylcyclopentyl)cyclohexyl)meth oxy)benzene (0.8 g).

The chemical shift (δ; ppm) in $^1$H-NMR analysis was described below, and the resulting compound was identified as 1-ethoxy-2,3-difluoro-4-((4-(3-propylcyclopentyl)cyclohexyl)meth oxy)benzene. The solvent for measurement was CDCl$_3$.

Chemical shift (δ; ppm): 6.81 (m, 2H), 4.05 (q, 2H), 3.76 (d, 2H), 1.95-1.70 (m, 8H), 1.55 (m, 2H), 1.45-0.85 (m, 17H) and 0.69 (q, 1H).

The phase transition temperature of the resulting compound No. 152 was as follows: Phase transition temperature: C 33.8 N 36.6 Iso.

A sample was prepared by mixing 15% by weight of the compound and 85% by weight of the mother liquid crystals (A), and the physical properties were calculated from the values obtained by measurement according to the extrapolation method. The physical properties of this compound were that NI=34.6° C.; Δ∈=−7.54; Δn=−0.074; q=64.3; mPa·s; and V$_{th}$=3.45.

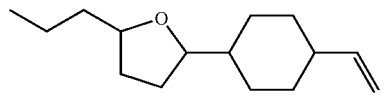 [SMILES: C=CC1CCC(C2CCC(CCC)O2)CC1]

Example 7

Preparation of 2-propyl-5-(4-vinylcyclohexyl)tetrahydrofuran (The Compound No. 261)

First Step:

Methoxymethyltriphenylphophnium chloride (55.23 g) and THF (300 ml) were placed in a reaction vessel, and the solution was cooled to −20° C. Potassium t-butoxide (16.0 g) was added, and the stirring was continued for another 1 hour. Then, 4-(5-propyltetrahydro-2-furanyl)cyclohexanone (15 g) in a THF (100 ml) solution was added dropwise, and the stirring was continued for another 1 hour. The reaction mixture was warmed to room temperature, and the mixture was separated after the addition of water (200 ml). The organic layer was dried over anhydrous magnesium sulfate and the solvent was distilled off under reduced pressure. The residue was purified by silica gel chromatography (toluene:ethyl acetate=18:1), and the resultant product was dissolved in acetone (200 ml) and hydrochrolic acid (6 M) (200 ml) was added, and then the stirring was continued at room temperature for another 1 hour. The mixture was extracted with toluene (100 ml) after the addition of water (200 ml). The solution was dried over anhydrous magnesium sulfate and the solvent was distilled off under reduced pressure to give 4-(5-propyltetrahydro-2-furanyl)cyclohexanecarboaldehyde (12.2 g).

Second Step:

Methyltriphenylphosphonium bromide (9.55 g) and THF (60 ml) were placed in a reaction vessel, and the solution was cooled to −20° C. Potassium t-butoxide (3.0 g) was added and the stirring was continued for another 1 hour. Then, 4-(5-propyltetrahydro-2-furanyl)cyclohexanecarboaldehyde (3 g) obtained in the preceding step, in a THF (10 ml) solution was added dropwise, and the stirring was continued for another 1 hour. The reaction mixture was warmed to room temperature, and the mixture was separated after the addition of water (100 ml). The organic layer was dried over anhydrous magnesium sulfate and the solvent was distilled off under reduced pressure. The residue was purified by silica gel chromatography (toluene), and then by means of a preparative HPLC system, Model PLC-561 made by GL Sciences Inc. to give 2-propyl-5-(4-vinylcyclohexyl)tetrahydrofuran (0.02 g).

The chemical shift (δ; ppm) in $^1$H-NMR analysis was described below, and the resulting compound was identified as 2-(4-(4-ethoxy-2,3-difluorophenyl)cyclohexyl)-5-propyltetrahydro furan. The solvent for measurement was CDCl$_3$.

Chemical shift (δ; ppm): 5.77 (m, 1H), 4.95 (d, 1H), 4.88 (d, 1H), 3.79 (q, 1H), 3.51 (q, 1H), 1.99 (d, 1H), 1.95-1.81 (m, 3H), 1.79 (d, 2H), 1.69 (d, 1H), 1.62-1.51 (m, 2H), 1.47-1.28 (m, 5H), 1.15-0.99 (m, 4H) and 0.94 (t, 3H).

The resulting compound No. 261 was isotropic down to −60° C.

Example 8

Preparation of 2-(4-(4-ethoxy-2,3-difluorophenyl) cyclohexyl)-5-propyltetrahydrofuran (The Compound No. 377)

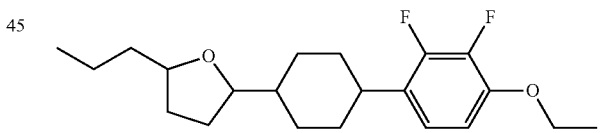

First Step:

Magnesium (0.49 g) and THF (10 ml) were placed in a reaction vessel, and 1-ethoxy-2,3-difluorobromobenzene (4.73 g) in a THF (20 ml) solution was added dropwise to the solution and the mixture was stirred for another 20 minutes. The mixture was cooled to −30° C., and 4-(5-propyltetrahydro-2-furanyl)cyclohexanone (3.5 g) in a THF solution was added dropwise, and the reaction mixture was warmed to room temperature, and then the stirring was continued overnight. After the completion of the reaction, 1N—HCl was added to the reaction mixture, which was extracted with toluene. The extract was washed successively with water and brine, and then dried over anhydrous magnesium sulfate. The solution was concentrated under reduced pressure and the concentrate was dissolved in toluene (250 ml), and p-TsOH (0.05 g) was added to it. The mixture was heated under reflux for 4 hours while water being distilled was removed. After the completion of the reaction, the reaction mixture was extracted with toluene, and the extract was washed successively with water and brine. The solution was dried over anhydrous magnesium sulfate and the solvent was distilled off under reduced pressure. The residue was purified by silica gel chromatography (toluene) to give 4-(4-ethoxy-2,3-difluorophenyl)cyclo-3-hexenyl)-5-propyltetrahydrofuran (4.02 g) as a colorless oil.

Second Step:

4-(4-Ethoxy-2,3-difluorophenyl)cyclo-3-hexenyl)-5-propyltetrahydrofuran (3 g) obtained in the first step was dissolved in isopropyl alcohol (50 ml), and the mixture was stirred at room temperature for 2 days under an atmosphere of hydrogen after the addition of Raney-Ni (1 g). After the completion of the reaction, Raney-Ni was filtered off and the filtrate was concentrated under educed pressure. The residue was purified by silica gel chromatography (toluene), and then by means of a preparative HPLC system, Model PLC-561 made by GL Sciences Inc. to give 2-(4-(4-ethoxy-2,3-difluorophenyl)cyclohexyl)-5-propyltetrahydrofuran (0.06 g) as a colorless oil.

The chemical shift (δ; ppm) in $^1$H-NMR analysis was described below, and the resulting compound was identified as 2-(4-(4-ethoxy-2,3-difluorophenyl)cyclohexyl)-5-propyltetrahydro furan. The solvent for measurement was CDCl$_3$.

Chemical shift (δ; ppm): 6.86 (t, 1H), 6.69 (t, 1H), 4.11 (q, 2H), 3.83 (quint, 1H), 3.59 (q, 1H), 2.78 (t, 1H), 2.10 (d, 1H), 1.99-1.87 (m, 4H), 1.80 (d, 1H), 1.60-1.55 (m, 2H), 1.54-1.27 (m, 7H), 1.45 (t, 3H), 1.21 (q, 2H) and 0.95 (t, 3H).

The resulting compound No. 377 was isotropic down to −60° C.

Example 9

The following compound No. 1 to No. 480 can be produced in a similar manner as in Examples 1 to 8.

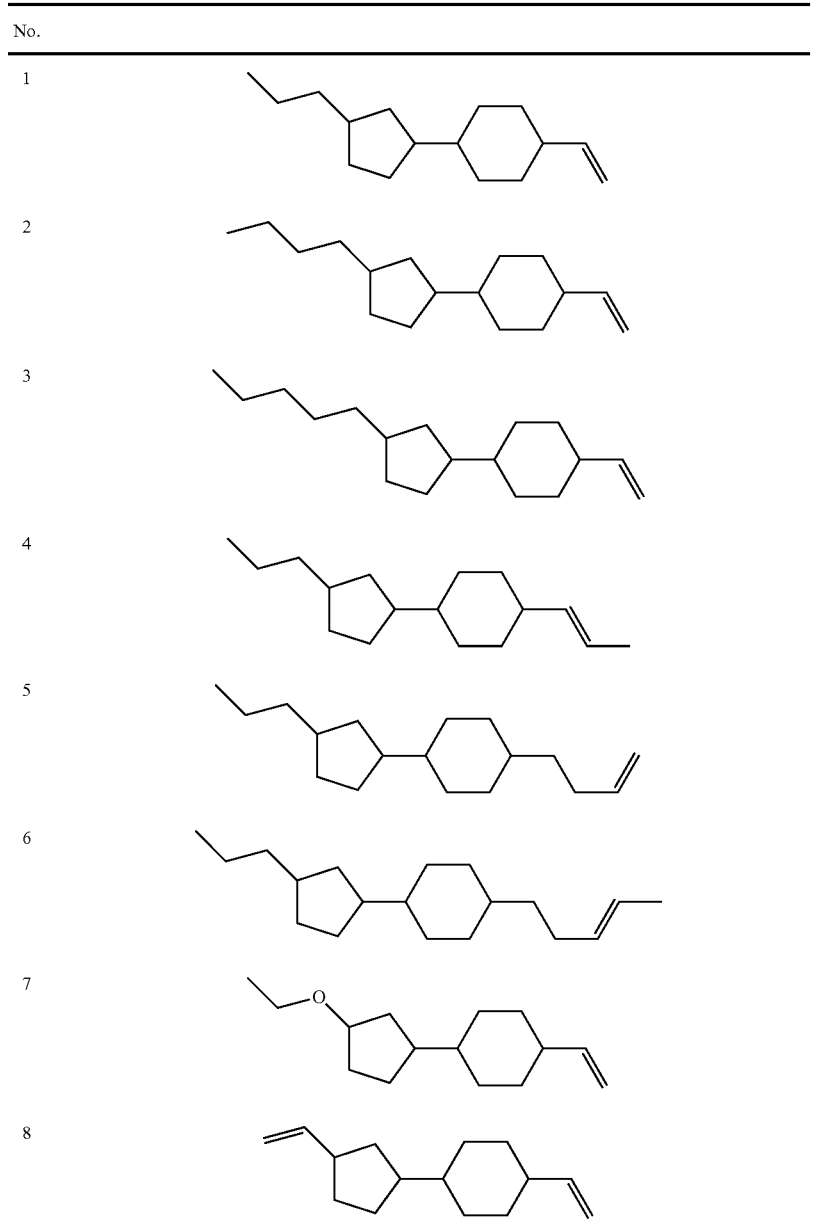

-continued
| No. | |
|---|---|
| 9 | 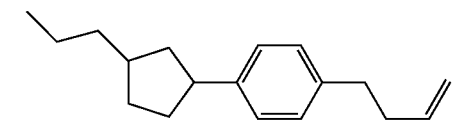 |
| 10 | 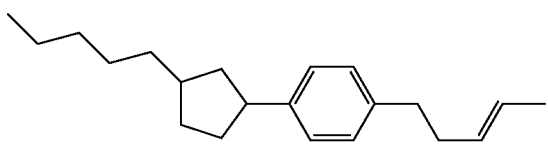 [SMILES: C/C=C/CCc1ccc(C2CCC(CCCCC)C2)cc1] |
| 11 | 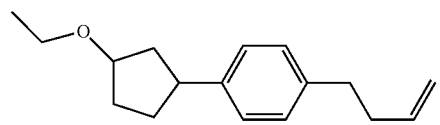 |
| 12 | 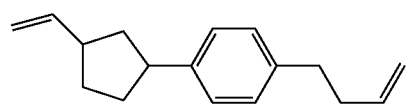 [SMILES: C=CCCc1ccc(C2CCC(C=C)C2)cc1] |
| 13 | 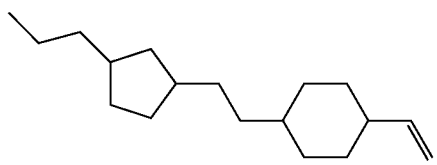 |
| 14 | 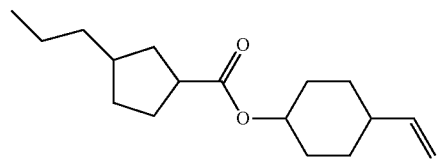 |
| 15 | 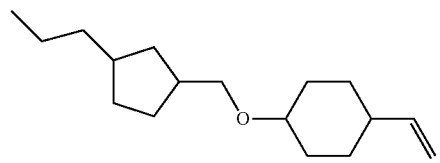 [SMILES: C=CC1CCC(CCC2CCC(CCC)C2)CC1] |
| 16 | 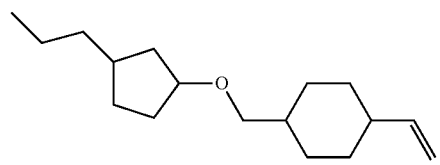 [SMILES: C=CC1CCC(COC2CCC(CCC)C2)CC1] |
| 17 | 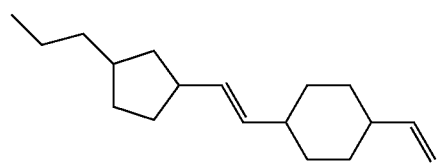 [SMILES: C=CC1CCC(/C=C/C2CCC(CCC)C2)CC1] |
| 18 | 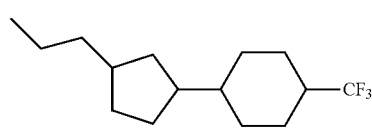 [SMILES: CCCC1CCC(C2CCC(C(F)(F)F)CC2)C1] |

-continued
| No. | |
|---|---|
| 19 | 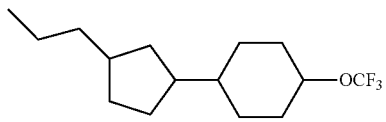 [SMILES: CCCC1CCC(C2CCC(OC(F)(F)F)CC2)C1] |
| 20 | 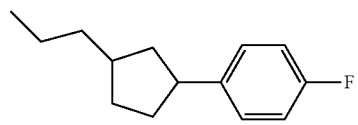 |
| 21 | 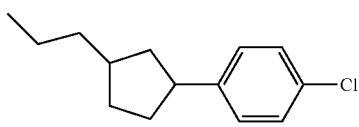 |
| 22 | 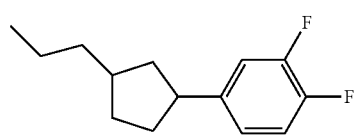 |
| 23 | 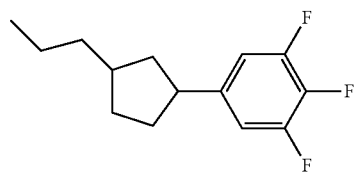 [SMILES: CCCC1CCC(c2cc(F)c(F)c(F)c2)C1] |
| 24 | 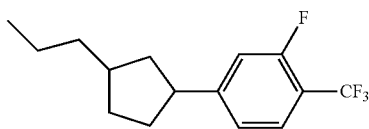 |
| 25 | 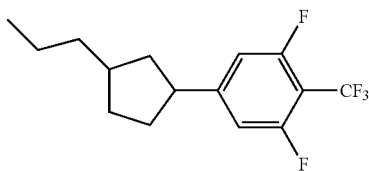 |
| 26 | 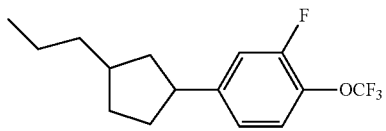 |
| 27 | 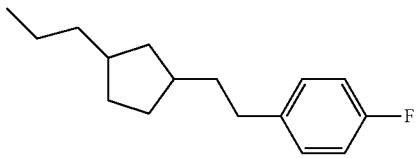 [SMILES: CCCC1CCC(CCc2ccc(F)cc2)C1] |
| 28 | 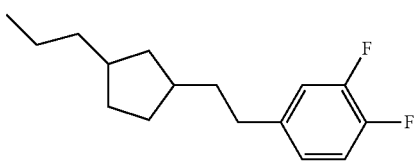 |

-continued
| No. | |
|---|---|
| 29 | 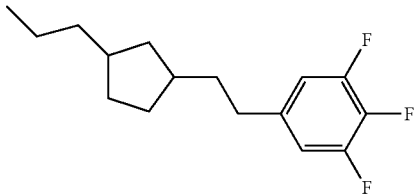 |
| 30 | 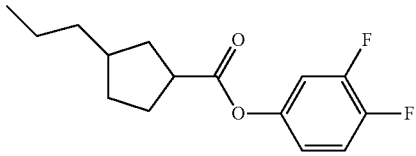 [SMILES: CCCC1CCC(C(=O)Oc2ccc(F)c(F)c2)C1] |
| 31 | 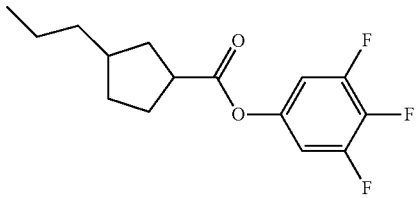 |
| 32 | 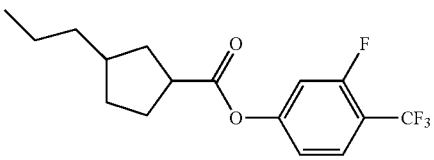 [SMILES: CCCC1CCC(C(=O)Oc2ccc(C(F)(F)F)c(F)c2)C1] |
| 33 | 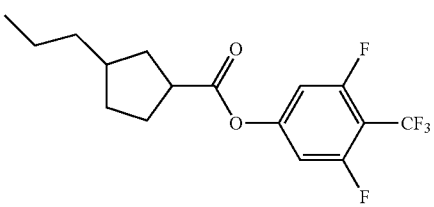 [SMILES: CCCC1CCC(C(=O)Oc2cc(F)c(C(F)(F)F)c(F)c2)C1] |
| 34 | 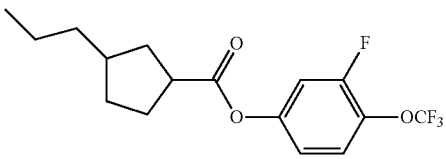 [SMILES: CCCC1CCC(C(=O)Oc2ccc(OC(F)(F)F)c(F)c2)C1] |
| 35 | 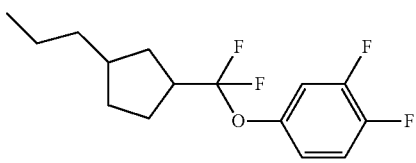 [SMILES: CCCC1CCC(C(F)(F)Oc2ccc(F)c(F)c2)C1] |
| 36 | 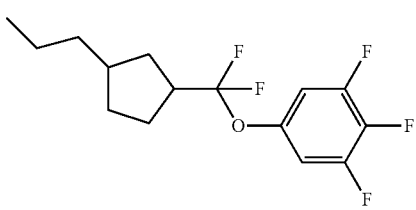 [SMILES: CCCC1CCC(C(F)(F)Oc2cc(F)c(F)c(F)c2)C1] |

-continued
| No. | |
|---|---|
| 37 | 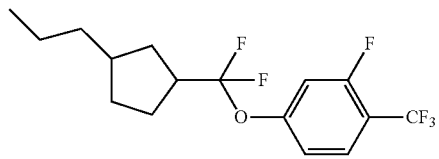 |
| 38 | 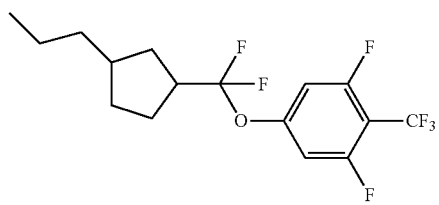 [SMILES: CCCC1CCC(C(F)(F)Oc2cc(F)c(C(F)(F)F)c(F)c2)C1] |
| 39 | 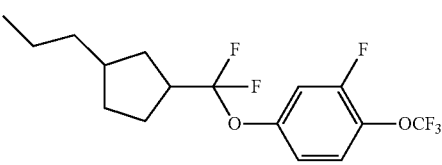 |
| 40 | 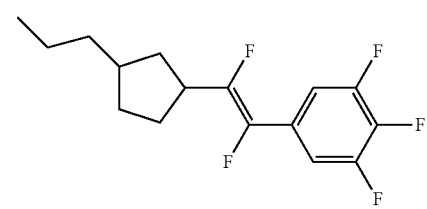 [SMILES: CCCC1CCC(/C(F)=C(\F)c2cc(F)c(F)c(F)c2)C1] |
| 41 | 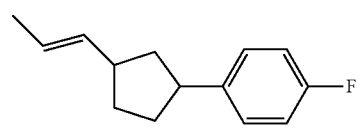 |
| 42 | 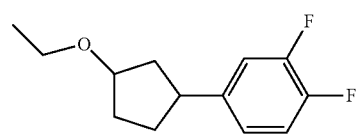 |
| 43 | 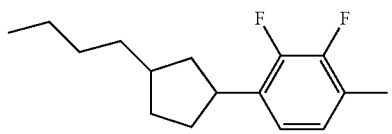 |
| 44 | 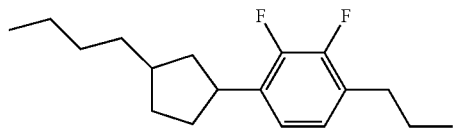 |
| 45 | 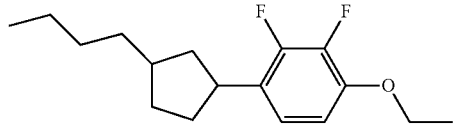 [SMILES: CCCCC1CCC(c2ccc(CCC)c(F)c2F)C1] |
| 46 | 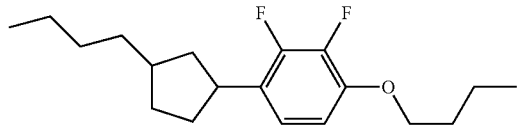 [SMILES: CCCCOc1ccc(C2CCC(CCCC)C2)c(F)c1F] |

| No. | |
|---|---|
| 47 | 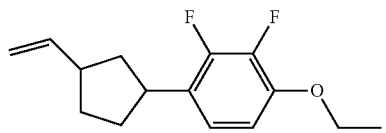 [SMILES: C=CC1CCC(c2ccc(OCC)c(F)c2F)C1] |
| 48 | 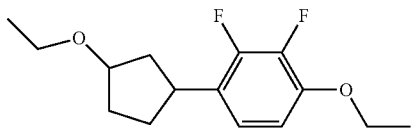 |
| 49 | 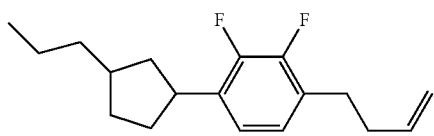 [SMILES: C=CCCc1ccc(C2CCC(CCC)C2)c(F)c1F] |
| 50 | 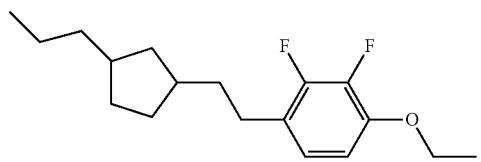 [SMILES: CCCC1CCC(CCc2ccc(OCC)c(F)c2F)C1] |
| 51 | 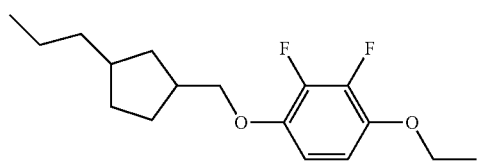 [SMILES: CCCC1CCC(COc2ccc(OCC)c(F)c2F)C1] |
| 52 | 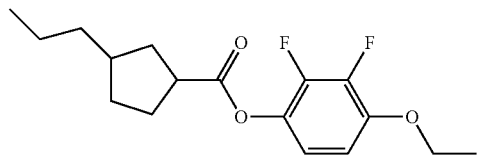 [SMILES: CCCC1CCC(C(=O)Oc2ccc(OCC)c(F)c2F)C1] |
| 53 | 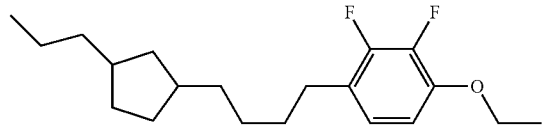 [SMILES: CCCC1CCC(CCCCc2ccc(OCC)c(F)c2F)C1] |
| 54 | 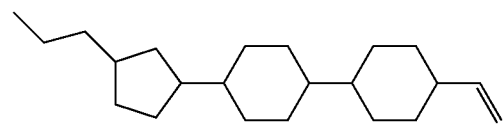 |
| 55 | 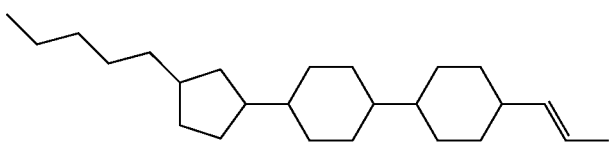 |
| 56 | 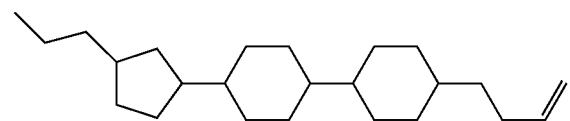 [SMILES: C=CCCC1CCC(C2CCC(C3CCC(CCC)C3)CC2)CC1] |

-continued
| No. | |
|---|---|
| 57 | 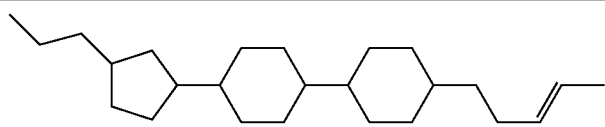 [SMILES: C/C=C/CCC1CCC(C2CCC(C3CCC(CCC)C3)CC2)CC1] |
| 58 | 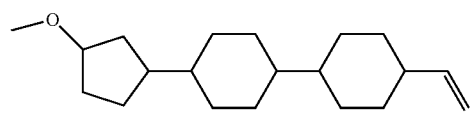 [SMILES: C=CC1CCC(C2CCC(C3CCC(OC)C3)CC2)CC1] |
| 59 | 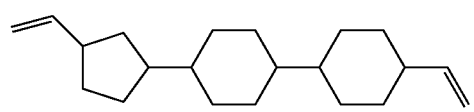 |
| 60 | 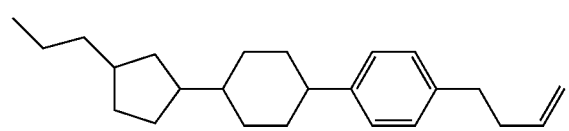 |
| 61 | 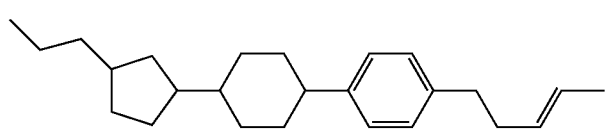 |
| 62 | 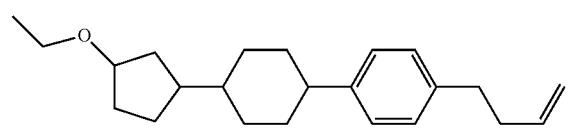 [SMILES: C=CCCc1ccc(C2CCC(C3CCC(CCC)C3)CC2)cc1] |
| 63 | 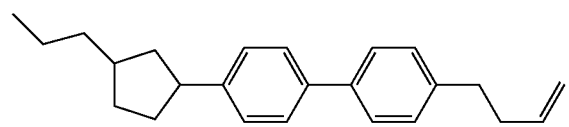 |
| 64 | 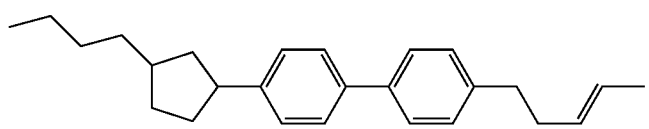 [SMILES: C/C=C/CCc1ccc(-c2ccc(C3CCC(CCCC)C3)cc2)cc1] |
| 65 | 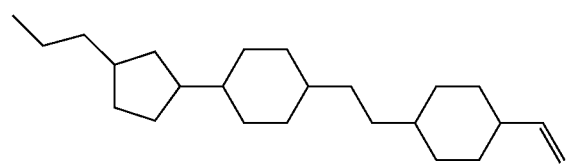 |
| 66 | 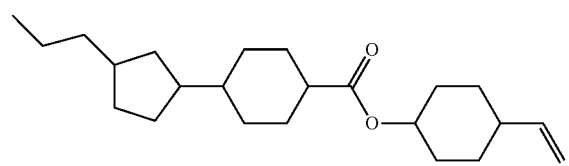 |
| 67 | 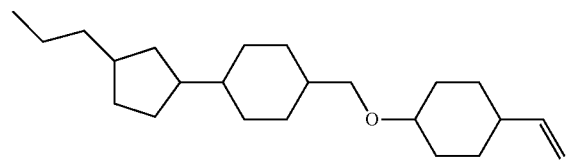 [SMILES: C=CC1CCC(OCC2CCC(C3CCC(CCC)C3)CC2)CC1] |

-continued
| No. | |
|---|---|
| 68 | 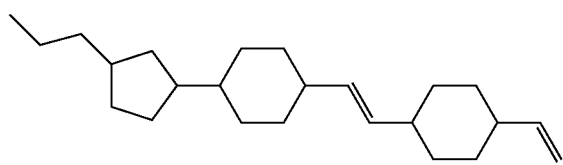 [SMILES: C=CC1CCC(/C=C/C2CCC(C3CCC(CCC)C3)CC2)CC1] |
| 69 | 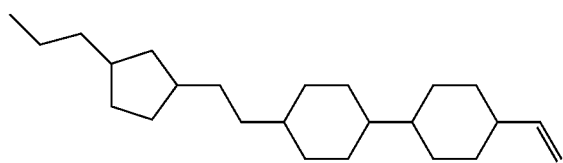 [SMILES: C=CC1CCC(C2CCC(CCC3CCC(CCC)C3)CC2)CC1] |
| 70 | 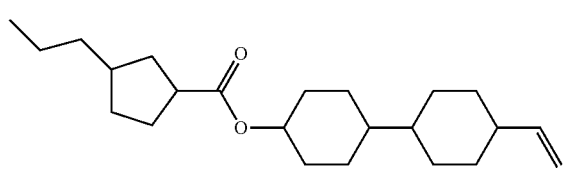 |
| 71 | 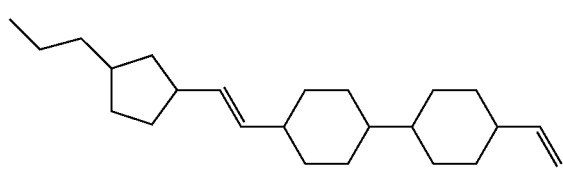 [SMILES: C=CC1CCC(C2CCC(/C=C/C3CCC(CCC)C3)CC2)CC1] |
| 72 | 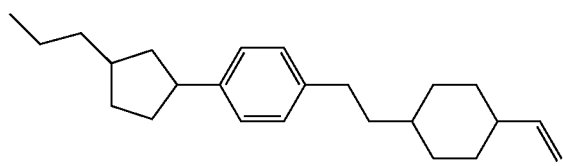 |
| 73 | 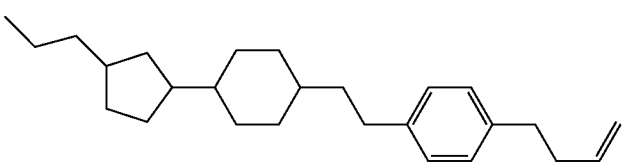 [SMILES: C=CCCc1ccc(CCC2CCC(C3CCC(CCC)C3)CC2)cc1] |
| 74 | 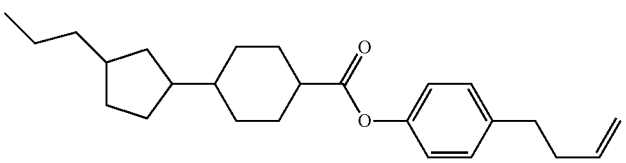 |
| 75 | 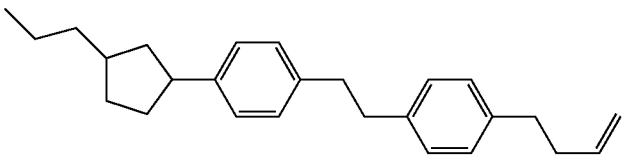 |
| 76 | 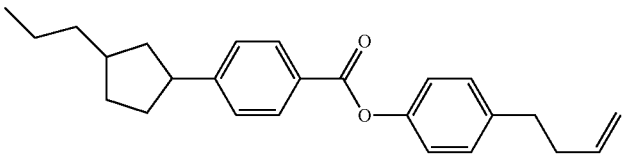 |

-continued
| No. | |
|---|---|
| 77 | 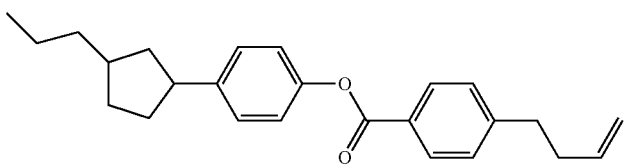 |
| 78 | 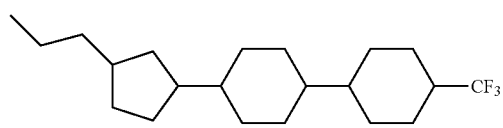 [SMILES: CCCC1CCC(C2CCC(C3CCC(C(F)(F)F)CC3)CC2)C1] |
| 79 | 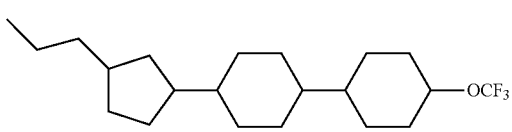 |
| 80 | 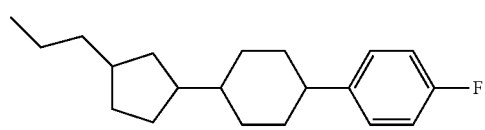 |
| 81 | 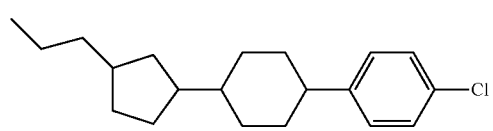 |
| 82 | 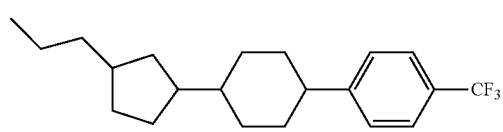 [SMILES: CCCC1CCC(C2CCC(c3ccc(C(F)(F)F)cc3)CC2)C1] |
| 83 | 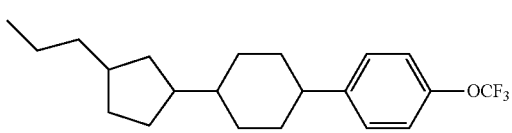 |
| 84 | 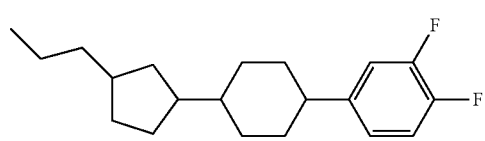 |
| 85 | 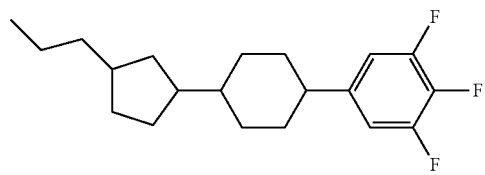 |
| 86 | 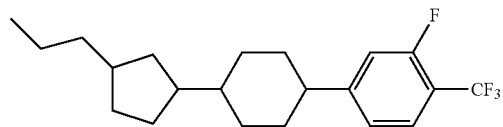 [SMILES: CCCC1CCC(C2CCC(c3ccc(C(F)(F)F)c(F)c3)CC2)C1] |

| No. | |
|---|---|
| 87 | 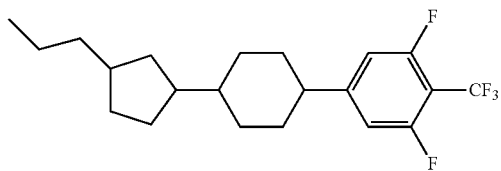 |
| 88 | 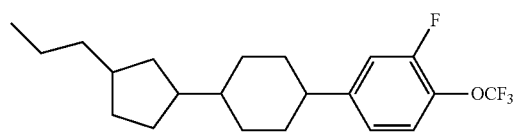 |
| 89 | 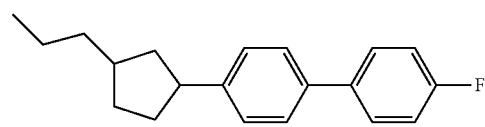 [SMILES: CCCC1CCC(c2ccc(-c3ccc(F)cc3)cc2)C1] |
| 90 | 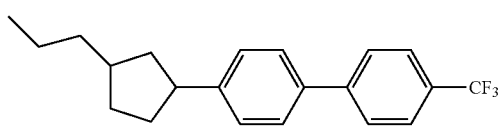 [SMILES: CCCC1CCC(c2ccc(-c3ccc(C(F)(F)F)cc3)cc2)C1] |
| 91 | 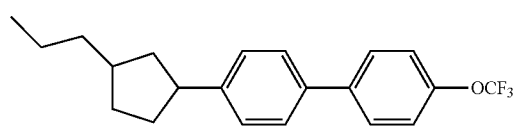 [SMILES: CCCC1CCC(c2ccc(-c3ccc(OC(F)(F)F)cc3)cc2)C1] |
| 92 | 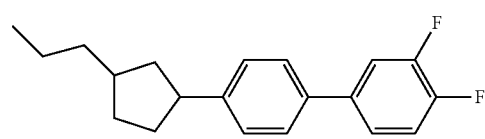 |
| 93 | 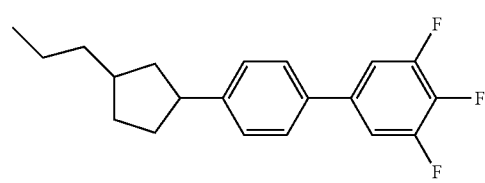 [SMILES: CCCC1CCC(c2ccc(-c3cc(F)c(F)c(F)c3)cc2)C1] |
| 94 | 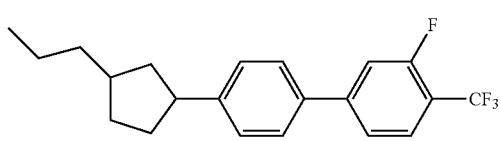 [SMILES: CCCC1CCC(c2ccc(-c3ccc(C(F)(F)F)c(F)c3)cc2)C1] |
| 95 | 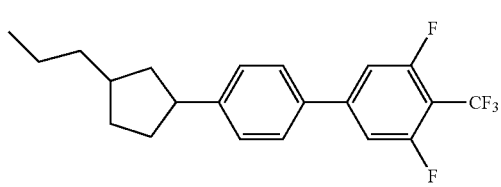 |
| 96 | 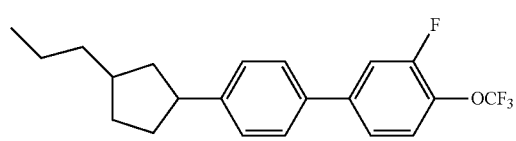 [SMILES: CCCC1CCC(c2ccc(-c3ccc(OC(F)(F)F)c(F)c3)cc2)C1] |

-continued
| No. | |
|---|---|
| 97 | 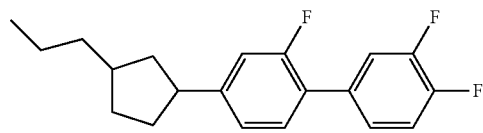 [SMILES: CCCC1CCC(c2ccc(-c3ccc(F)c(F)c3)c(F)c2)C1] |
| 98 | 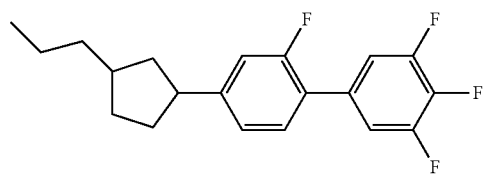 |
| 99 | 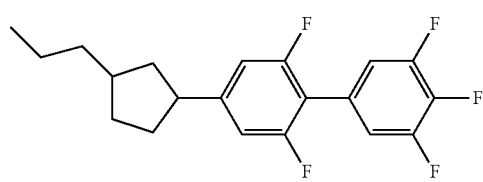 [SMILES: CCCC1CCC(c2ccc(-c3cc(F)c(F)c(F)c3)c(F)c2)C1] |
| 100 | 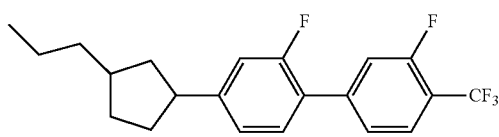 |
| 101 | 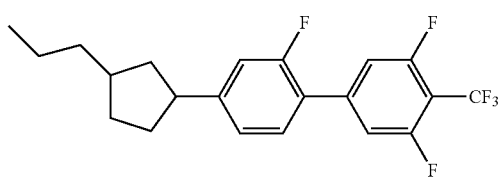 |
| 102 | 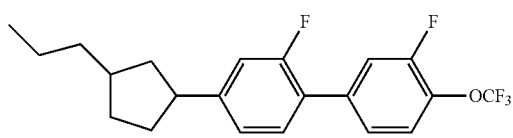 |
| 103 | 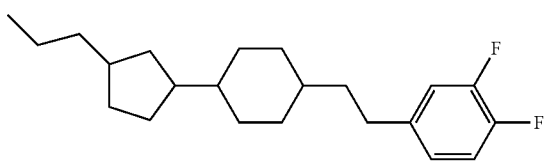 [SMILES: CCCC1CCC(C2CCC(CCc3ccc(F)c(F)c3)CC2)C1] |
| 104 | 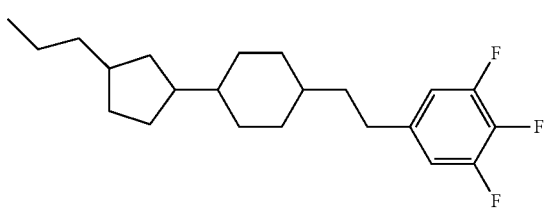 [SMILES: CCCC1CCC(C2CCC(CCc3cc(F)c(F)c(F)c3)CC2)C1] |
| 105 | 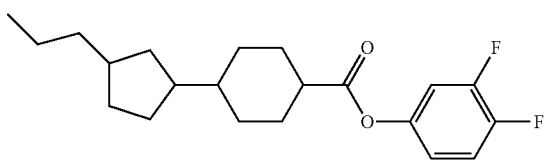 [SMILES: CCCC1CCC(C2CCC(C(=O)Oc3ccc(F)c(F)c3)CC2)C1] |

| No. | |
|---|---|
| 106 | 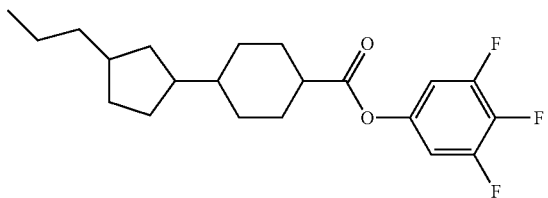 [SMILES: CCCC1CCC(C2CCC(C(=O)Oc3cc(F)c(F)c(F)c3)CC2)C1] |
| 107 | 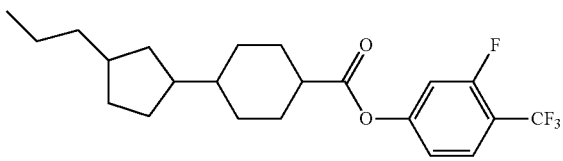 [SMILES: CCCC1CCC(C2CCC(C(=O)Oc3ccc(C(F)(F)F)c(F)c3)CC2)C1] |
| 108 | 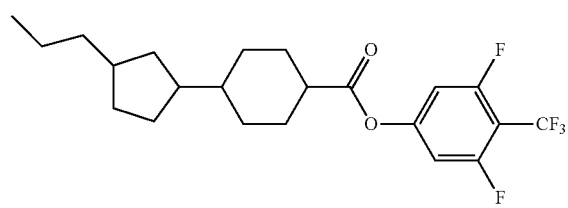 |
| 109 | 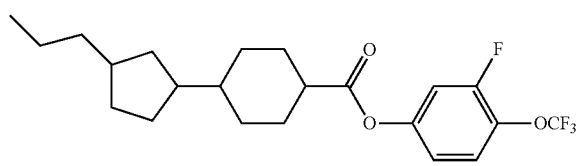 [SMILES: CCCC1CCC(C2CCC(C(=O)Oc3ccc(OC(F)(F)F)c(F)c3)CC2)C1] |
| 110 | 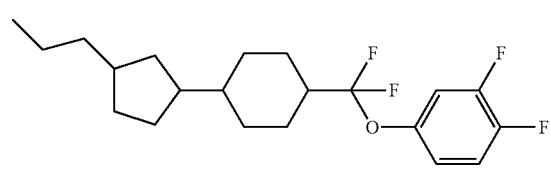 [SMILES: CCCC1CCC(C2CCC(C(F)(F)Oc3ccc(F)c(F)c3)CC2)C1] |
| 111 | 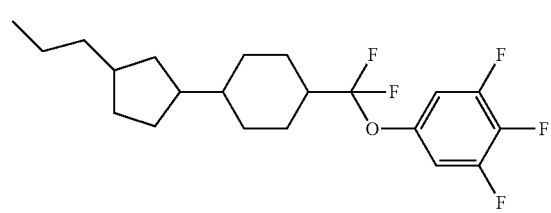 |
| 112 | 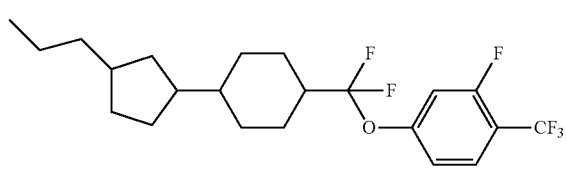 [SMILES: CCCC1CCC(C2CCC(C(F)(F)Oc3ccc(C(F)(F)F)c(F)c3)CC2)C1] |
| 113 | 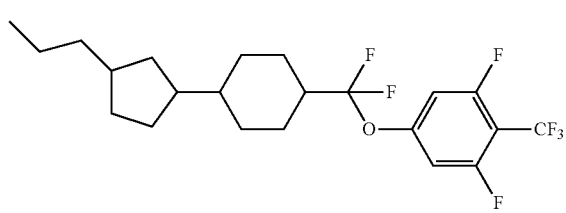 [SMILES: CCCC1CCC(C2CCC(C(F)(F)Oc3cc(F)c(C(F)(F)F)c(F)c3)CC2)C1] |

| No. | |
|---|---|
| 114 | 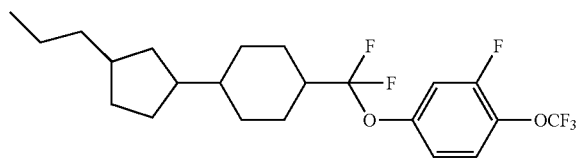 |
| 115 | 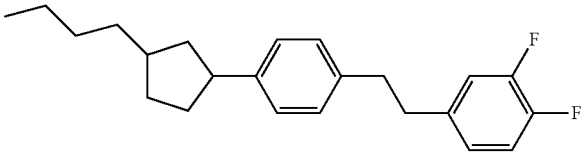 [SMILES: CCCCC1CCC(c2ccc(CCc3ccc(F)c(F)c3)cc2)C1] |
| 116 | 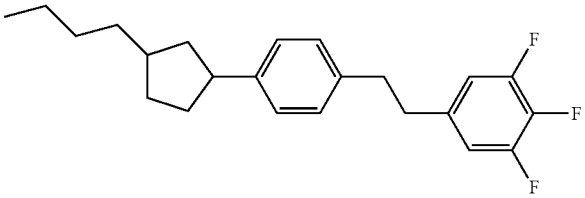 [SMILES: CCCCC1CCC(c2ccc(CCc3cc(F)c(F)c(F)c3)cc2)C1] |
| 117 | 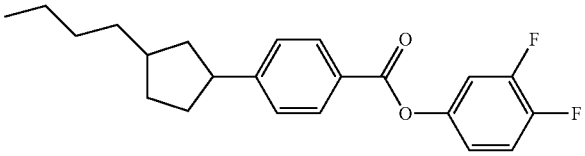 [SMILES: CCCCC1CCC(c2ccc(C(=O)Oc3ccc(F)c(F)c3)cc2)C1] |
| 118 | 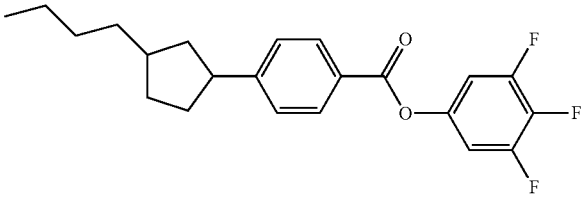 [SMILES: CCCCC1CCC(c2ccc(C(=O)Oc3cc(F)c(F)c(F)c3)cc2)C1] |
| 119 | 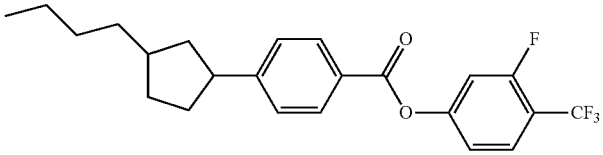 [SMILES: CCCCC1CCC(c2ccc(C(=O)Oc3ccc(C(F)(F)F)c(F)c3)cc2)C1] |
| 120 | 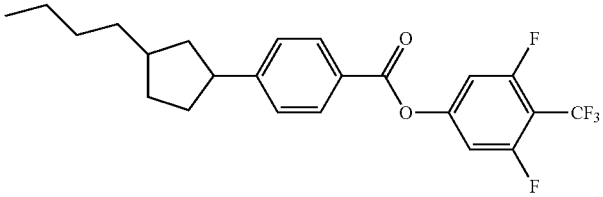 [SMILES: CCCCC1CCC(c2ccc(C(=O)Oc3cc(F)c(C(F)(F)F)c(F)c3)cc2)C1] |
| 121 | 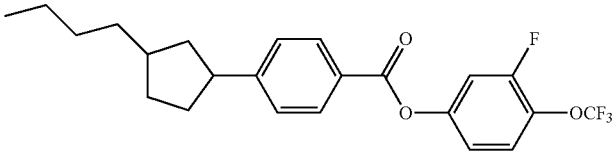 [SMILES: CCCCC1CCC(c2ccc(C(=O)Oc3ccc(OC(F)(F)F)c(F)c3)cc2)C1] |

| No. | |
|---|---|
| 122 | 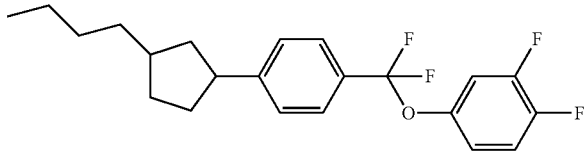 [SMILES: CCCCC1CCC(c2ccc(C(F)(F)Oc3ccc(F)c(F)c3)cc2)C1] |
| 123 | 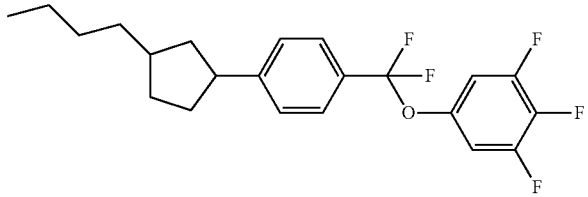 [SMILES: CCCCC1CCC(c2ccc(C(F)(F)Oc3cc(F)c(F)c(F)c3)cc2)C1] |
| 124 | 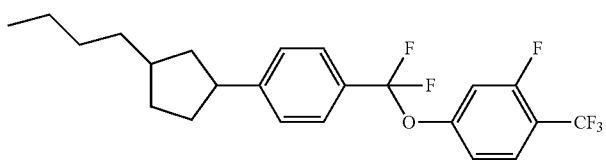 [SMILES: CCCCC1CCC(c2ccc(C(F)(F)Oc3ccc(C(F)(F)F)c(F)c3)cc2)C1] |
| 125 | 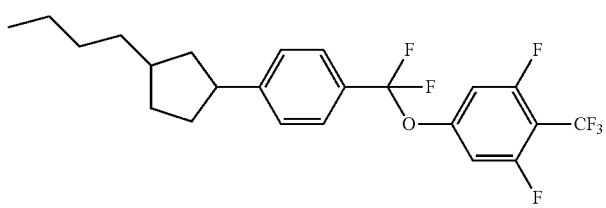 [SMILES: CCCCC1CCC(c2ccc(C(F)(F)Oc3cc(F)c(C(F)(F)F)c(F)c3)cc2)C1] |
| 126 | 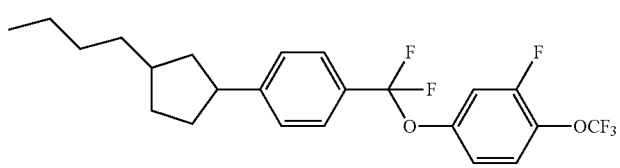 [SMILES: CCCCC1CCC(c2ccc(C(F)(F)Oc3ccc(OC(F)(F)F)c(F)c3)cc2)C1] |
| 127 | 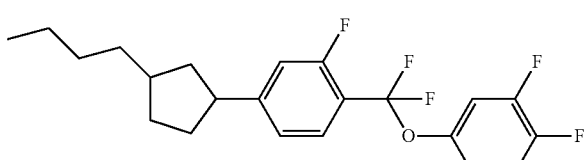 |
| 128 | 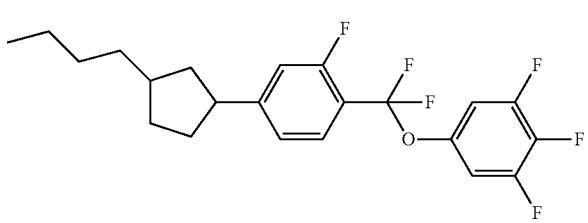 [SMILES: CCCCC1CCC(c2ccc(C(F)(F)Oc3cc(F)c(F)c(F)c3)c(F)c2)C1] |
| 129 | 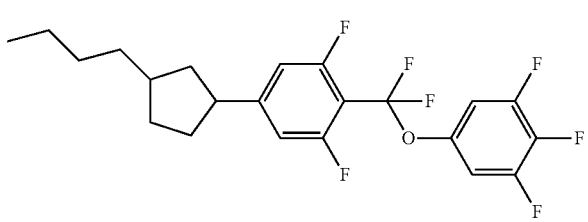 [SMILES: CCCCC1CCC(c2cc(F)c(C(F)(F)Oc3cc(F)c(F)c(F)c3)c(F)c2)C1] |

| No. | |
|---|---|
| 130 | 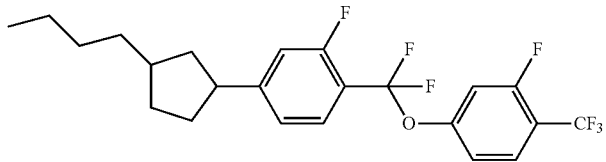 [SMILES: CCCCC1CCC(c2ccc(C(F)(F)Oc3ccc(C(F)(F)F)c(F)c3)c(F)c2)C1] |
| 131 | 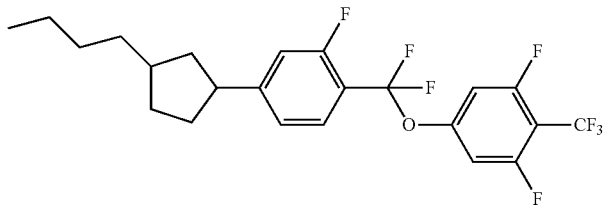 [SMILES: CCCCC1CCC(c2ccc(C(F)(F)Oc3cc(F)c(C(F)(F)F)c(F)c3)c(F)c2)C1] |
| 132 | 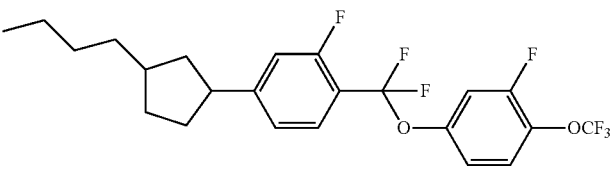 [SMILES: CCCCC1CCC(c2ccc(C(F)(F)Oc3ccc(OC(F)(F)F)c(F)c3)c(F)c2)C1] |
| 133 | 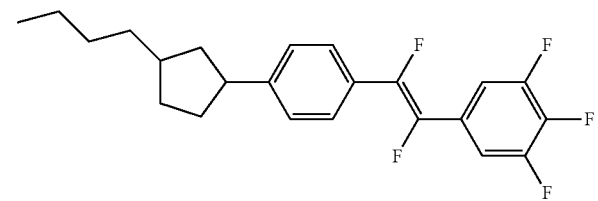 [SMILES: CCCCC1CCC(c2ccc(/C(F)=C(\F)c3cc(F)c(F)c(F)c3)cc2)C1] |
| 134 | 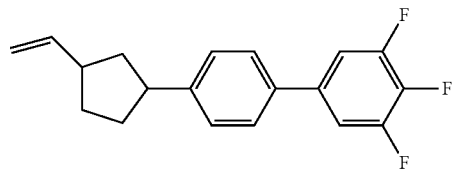 |
| 135 | 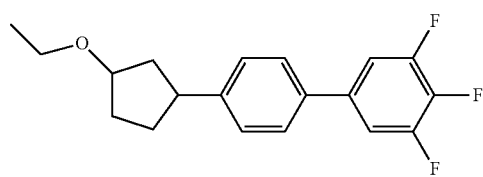 |
| 136 | 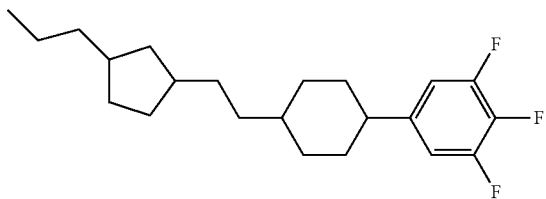 [SMILES: CCCC1CCC(CCC2CCC(c3cc(F)c(F)c(F)c3)CC2)C1] |
| 137 | 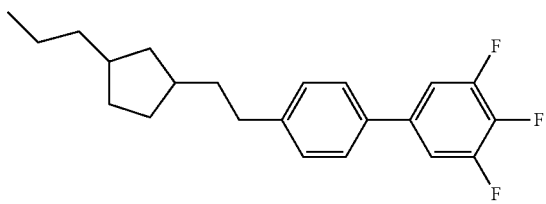 |

-continued
| No. | |
|---|---|
| 138 | 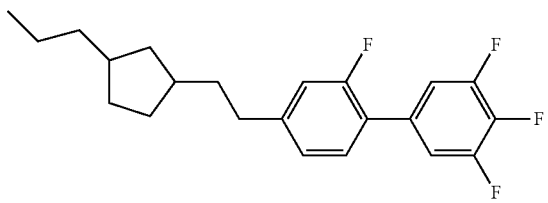 [SMILES: CCCC1CCC(CCc2ccc(-c3cc(F)c(F)c(F)c3)c(F)c2)C1] |
| 139 | 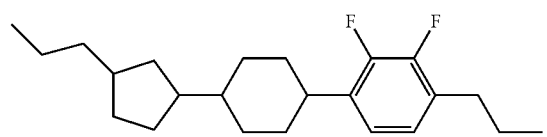 |
| 140 | 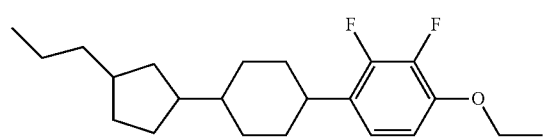 [SMILES: CCCc1ccc(C2CCC(C3CCC(CCC)C3)CC2)c(F)c1F] |
| 141 | 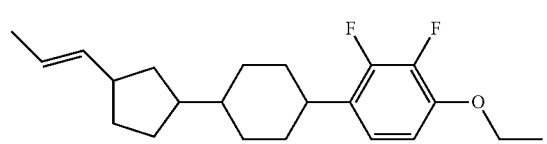 |
| 142 | 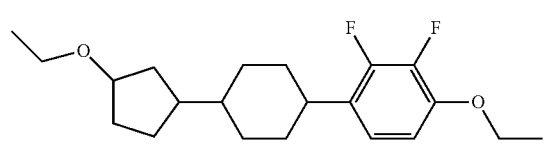 |
| 143 | 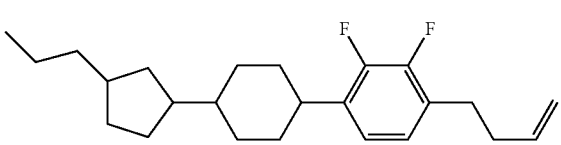 [SMILES: C=CCCc1ccc(C2CCC(C3CCC(CCC)C3)CC2)c(F)c1F] |
| 144 | 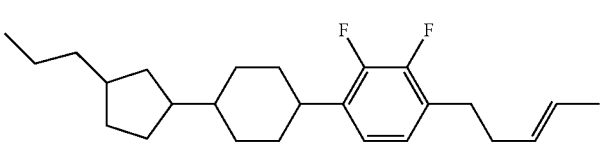 [SMILES: C/C=C/CCc1ccc(C2CCC(C3CCC(CCC)C3)CC2)c(F)c1F] |
| 145 | 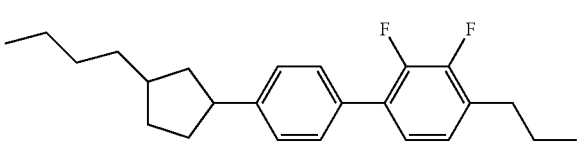 [SMILES: CCCCC1CCC(c2ccc(-c3ccc(CCC)c(F)c3F)cc2)C1] |
| 146 | 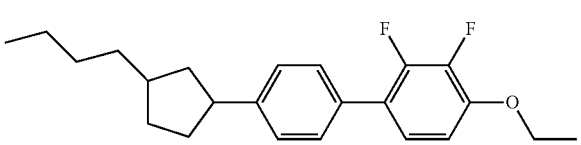 |
| 147 |  |

-continued
| No. | |
|---|---|
| 148 | 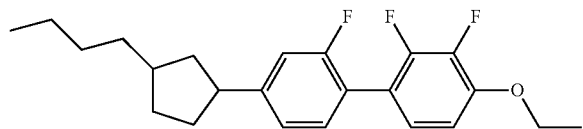 [SMILES: CCCCC1CCC(c2ccc(-c3ccc(OCC)c(F)c3F)c(F)c2)C1] |
| 149 | 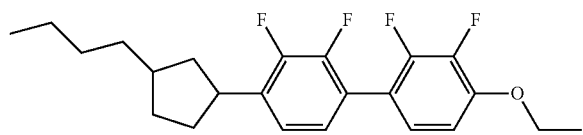 [SMILES: CCCCC1CCC(c2ccc(-c3ccc(OCC)c(F)c3F)c(F)c2F)C1] |
| 150 | 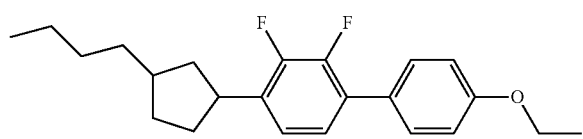 |
| 151 | 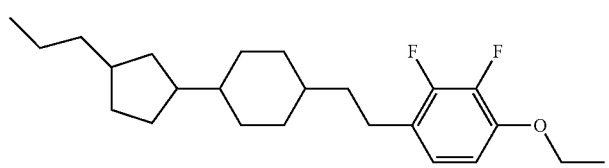 [SMILES: CCCC1CCC(C2CCC(CCc3ccc(OCC)c(F)c3F)CC2)C1] |
| 152 | 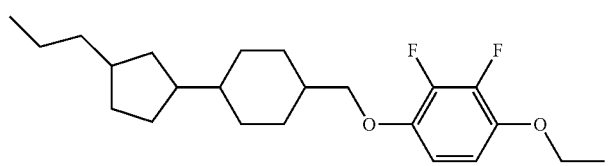 |
| 153 | 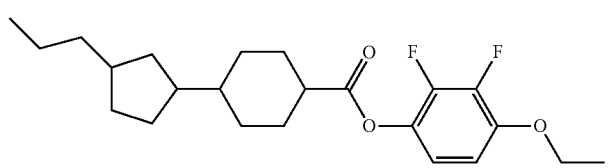 [SMILES: CCCC1CCC(C2CCC(C(=O)Oc3ccc(OCC)c(F)c3F)CC2)C1] |
| 154 | 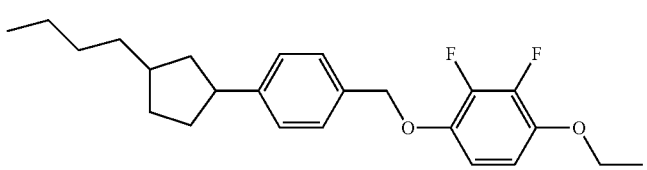 [SMILES: CCCCC1CCC(c2ccc(COc3ccc(OCC)c(F)c3F)cc2)C1] |
| 155 | 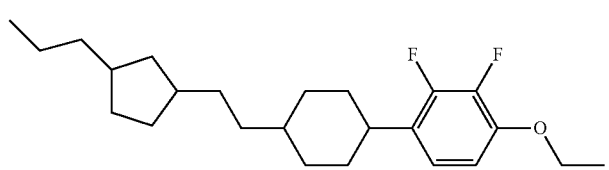 |
| 156 | 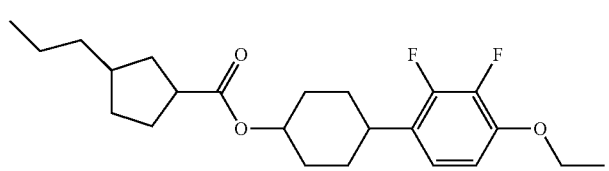 |
| 157 | 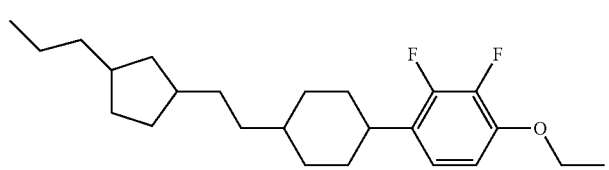 |

-continued
| No. |
|---|
| 158 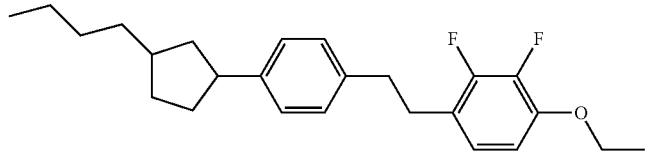 [SMILES: CCCCC1CCC(c2ccc(CCc3ccc(OCC)c(F)c3F)cc2)C1] |
| 159 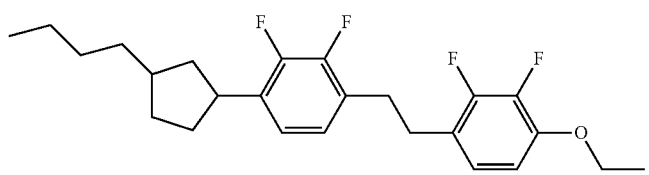 [SMILES: CCCCC1CCC(c2ccc(CCc3ccc(OCC)c(F)c3F)c(F)c2F)C1] |
| 160 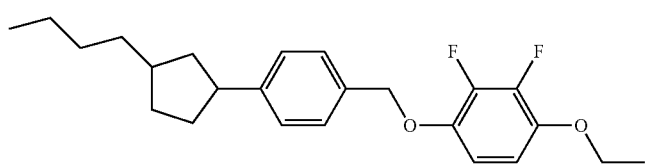 |
| 161 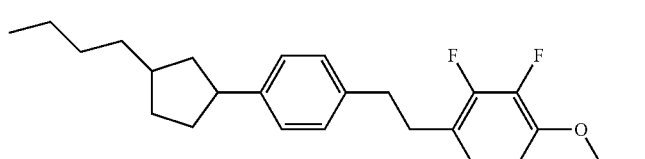 |
| 162 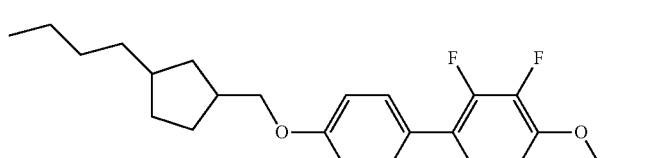 |
| 163 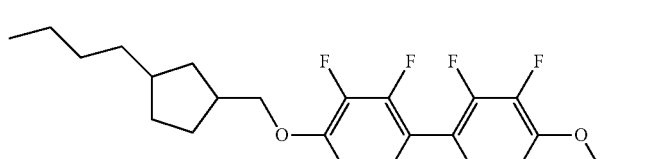 |
| 164 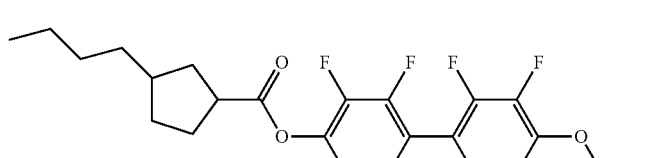 |
| 165 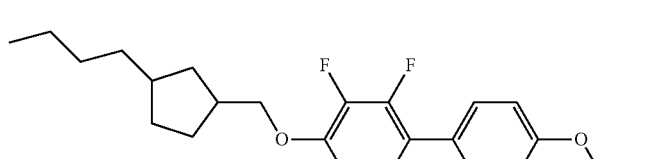 |
| 166 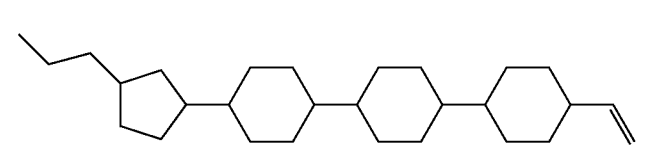 |

-continued
| No. | |
|---|---|
| 167 | 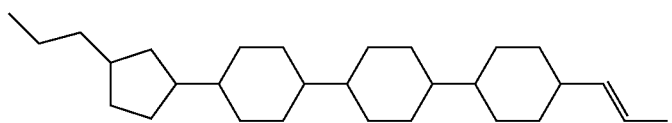 [SMILES: C/C=C/C1CCC(C2CCC(C3CCC(C4CCC(CCC)C4)CC3)CC2)CC1] |
| 168 | 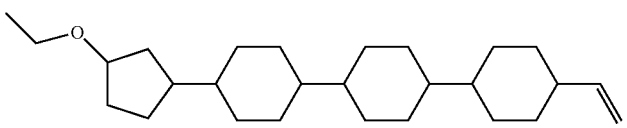 |
| 169 | 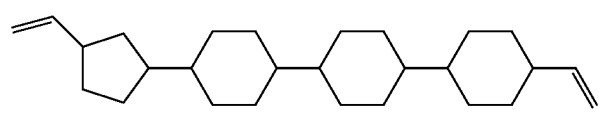 |
| 170 | 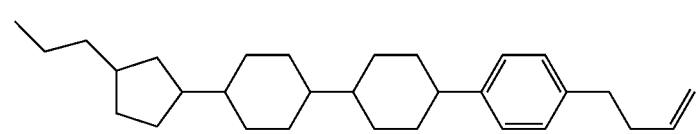 [SMILES: C=CCCc1ccc(C2CCC(C3CCC(C4CCC(CCC)C4)CC3)CC2)cc1] |
| 171 | 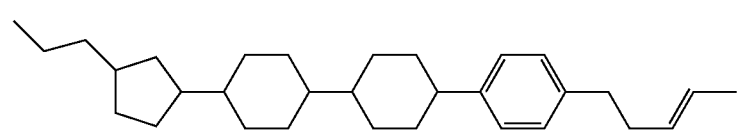 [SMILES: C/C=C/CCc1ccc(C2CCC(C3CCC(C4CCC(CCC)C4)CC3)CC2)cc1] |
| 172 | 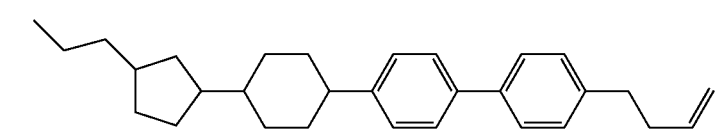 |
| 173 | 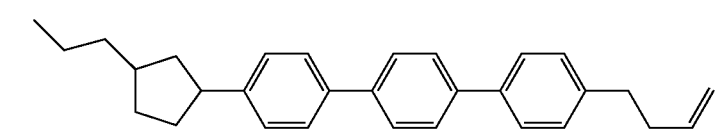 |
| 174 | 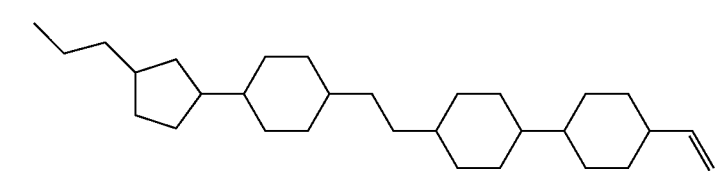 |
| 175 | 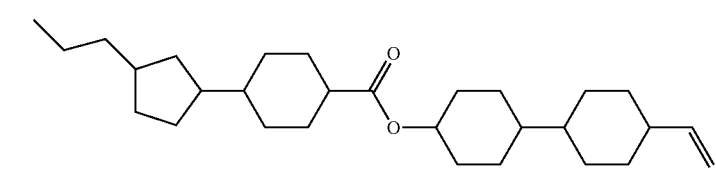 |
| 176 | 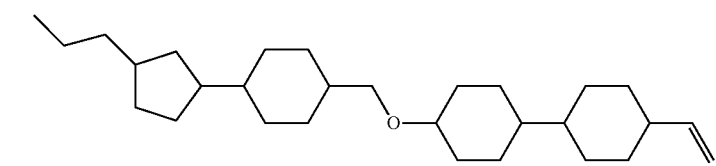 [SMILES: C=CC1CCC(C2CCC(OCC3CCC(C4CCC(CCC)C4)CC3)CC2)CC1] |
| 177 | 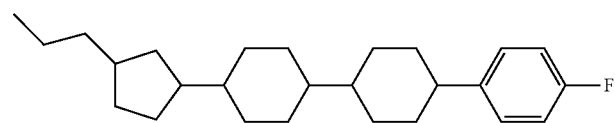 [SMILES: CCCC1CCC(C2CCC(C3CCC(c4ccc(F)cc4)CC3)CC2)C1] |

|No.| |
|---|---|
|178|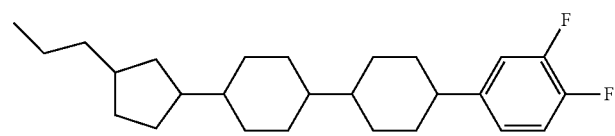|
|179|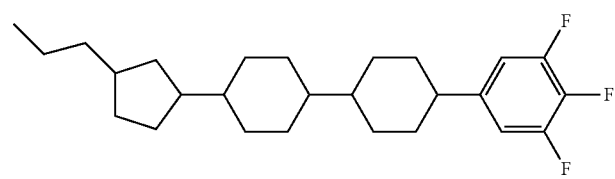 [SMILES: CCCC1CCC(C2CCC(C3CCC(c4cc(F)c(F)c(F)c4)CC3)CC2)C1]|
|180|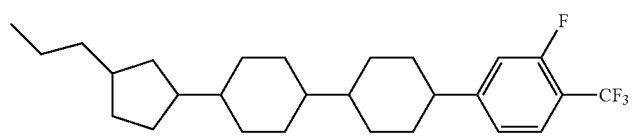 [SMILES: CCCC1CCC(C2CCC(C3CCC(c4ccc(C(F)(F)F)c(F)c4)CC3)CC2)C1]|
|181|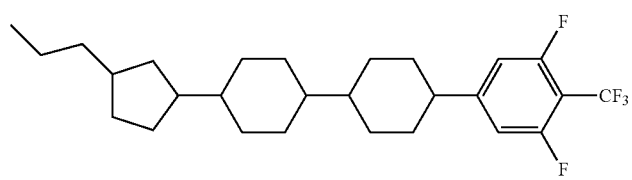|
|182|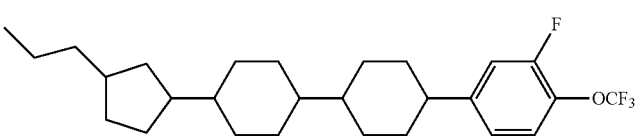 [SMILES: CCCC1CCC(C2CCC(C3CCC(c4ccc(OC(F)(F)F)c(F)c4)CC3)CC2)C1]|
|183|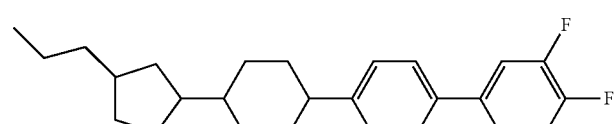|
|184|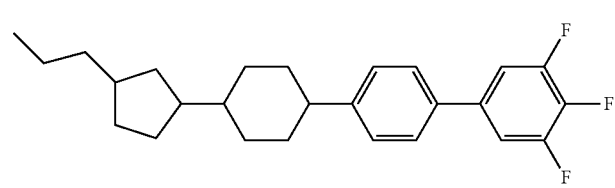|
|185|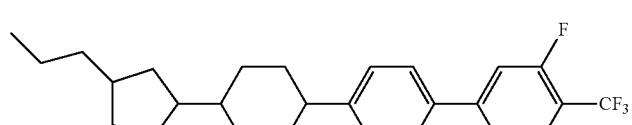|
|186|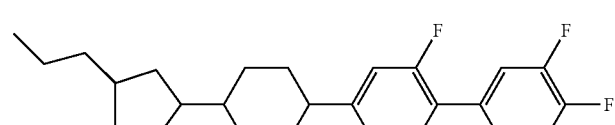|
|187|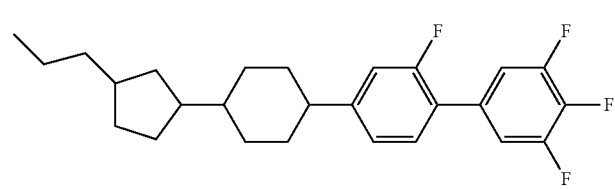|

| No. | |
|---|---|
| 188 | 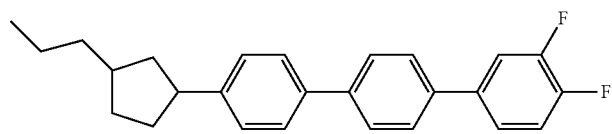 |
| 189 | 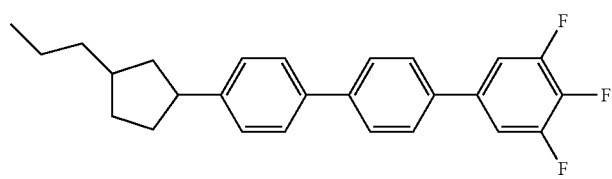 [SMILES: CCCC1CCC(c2ccc(-c3ccc(-c4cc(F)c(F)c(F)c4)cc3)cc2)C1] |
| 190 | 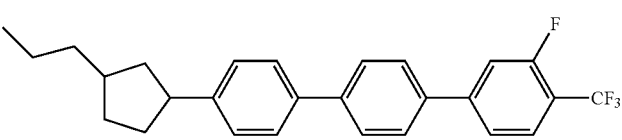 |
| 191 | 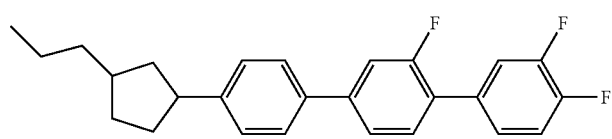 |
| 192 | 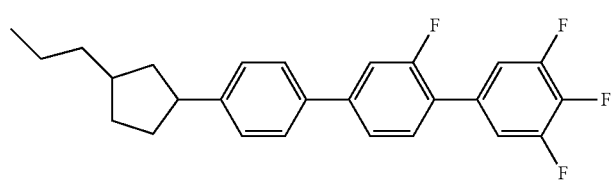 |
| 193 | 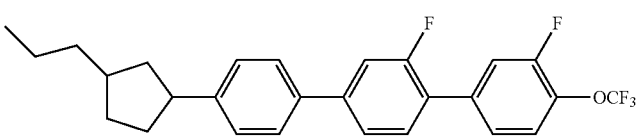 |
| 194 | 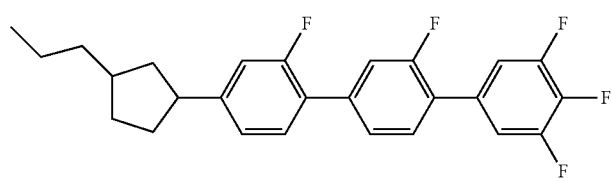 |
| 195 | 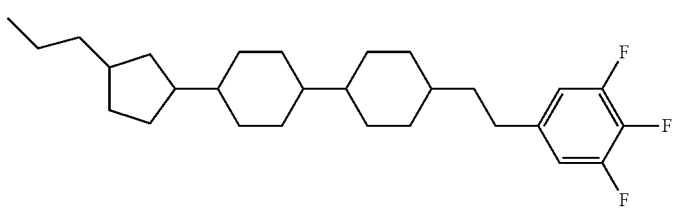 [SMILES: CCCC1CCC(C2CCC(C3CCC(CCc4cc(F)c(F)c(F)c4)CC3)CC2)C1] |
| 196 | 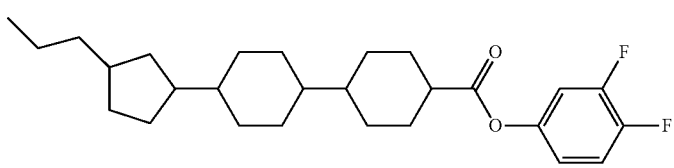 [SMILES: CCCC1CCC(C2CCC(C3CCC(C(=O)Oc4ccc(F)c(F)c4)CC3)CC2)C1] |

-continued
| No. | |
|---|---|
| 197 | 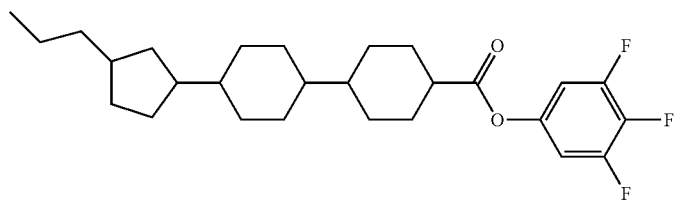 [SMILES: CCCC1CCC(C2CCC(C3CCC(C(=O)Oc4cc(F)c(F)c(F)c4)CC3)CC2)C1] |
| 198 | 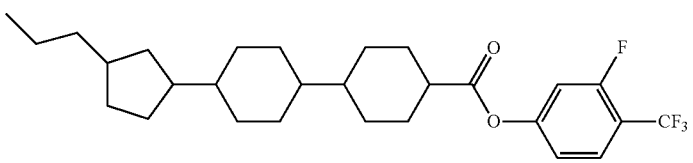 [SMILES: CCCC1CCC(C2CCC(C3CCC(C(=O)Oc4ccc(C(F)(F)F)c(F)c4)CC3)CC2)C1] |
| 199 | 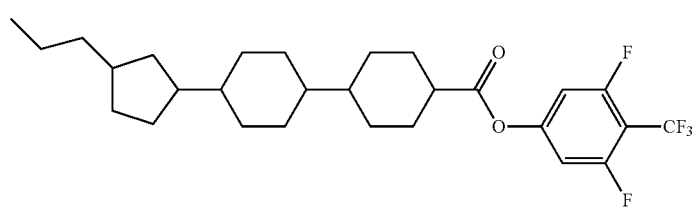 [SMILES: CCCC1CCC(C2CCC(C3CCC(C(=O)Oc4cc(F)c(C(F)(F)F)c(F)c4)CC3)CC2)C1] |
| 200 | 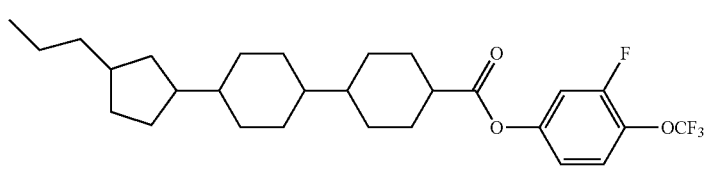 |
| 201 | 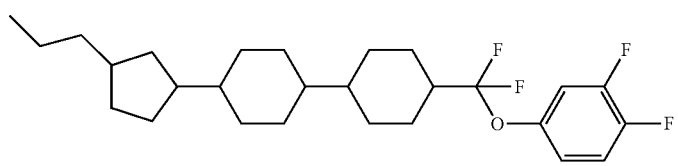 [SMILES: CCCC1CCC(C2CCC(C3CCC(C(F)(F)Oc4ccc(F)c(F)c4)CC3)CC2)C1] |
| 202 | 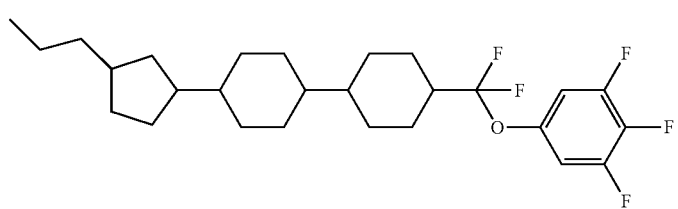 |
| 203 | 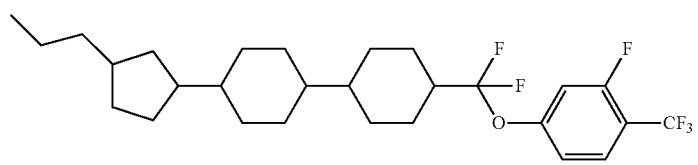 |
| 204 | 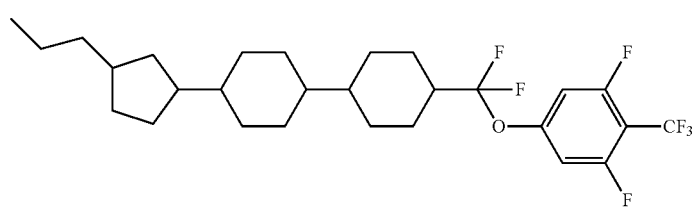 [SMILES: CCCC1CCC(C2CCC(C3CCC(C(F)(F)Oc4cc(F)c(C(F)(F)F)c(F)c4)CC3)CC2)C1] |

| No. | |
|---|---|
| 205 | 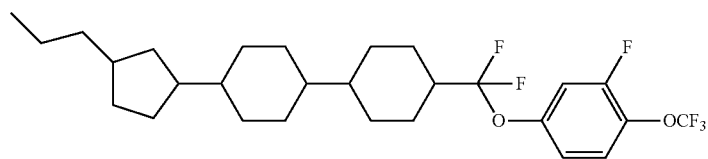 [SMILES: CCCC1CCC(C2CCC(C3CCC(C(F)(F)Oc4ccc(OC(F)(F)F)c(F)c4)CC3)CC2)C1] |
| 206 | 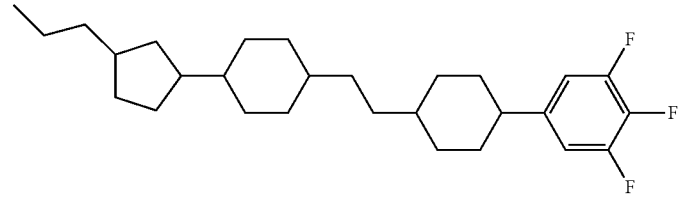 [SMILES: CCCC1CCC(C2CCC(CCC3CCC(c4cc(F)c(F)c(F)c4)CC3)CC2)C1] |
| 207 | 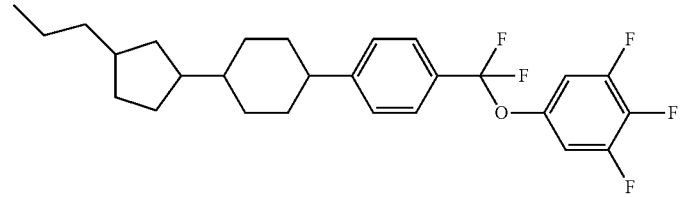 |
| 208 | 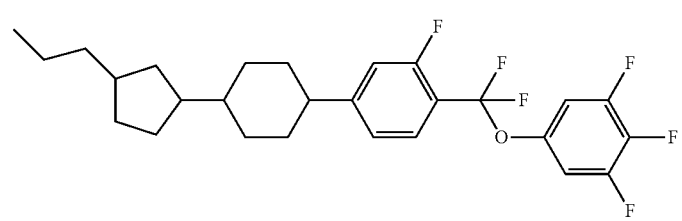 [SMILES: CCCC1CCC(C2CCC(c3ccc(C(F)(F)Oc4cc(F)c(F)c(F)c4)c(F)c3)CC2)C1] |
| 209 | 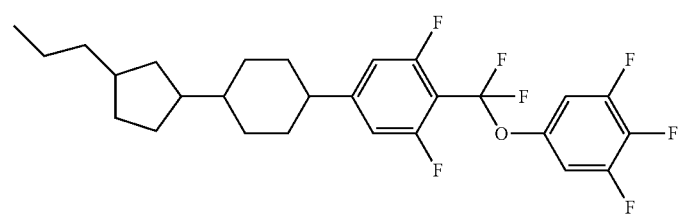 |
| 210 | 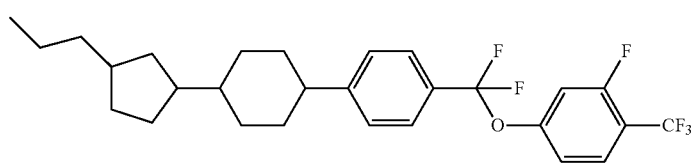 [SMILES: CCCC1CCC(C2CCC(c3ccc(C(F)(F)Oc4ccc(C(F)(F)F)c(F)c4)cc3)CC2)C1] |
| 211 | 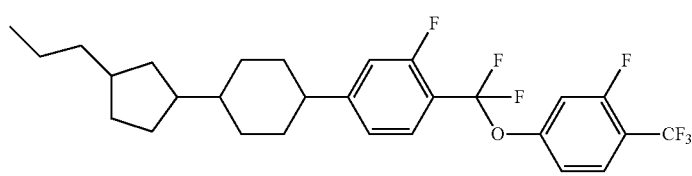 [SMILES: CCCC1CCC(C2CCC(c3ccc(C(F)(F)Oc4ccc(C(F)(F)F)c(F)c4)c(F)c3)CC2)C1] |
| 212 | 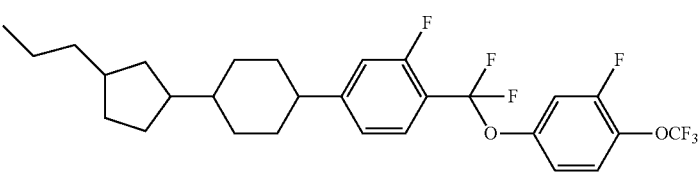 |

-continued
| No. | |
|---|---|
| 213 | 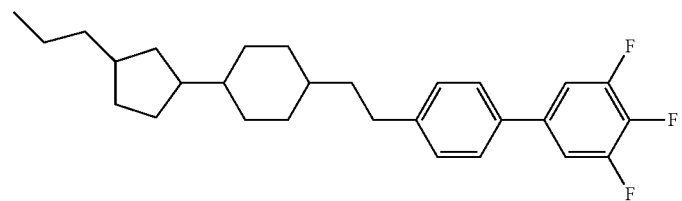 [SMILES: CCCC1CCC(C2CCC(CCc3ccc(-c4cc(F)c(F)c(F)c4)cc3)CC2)C1] |
| 214 | 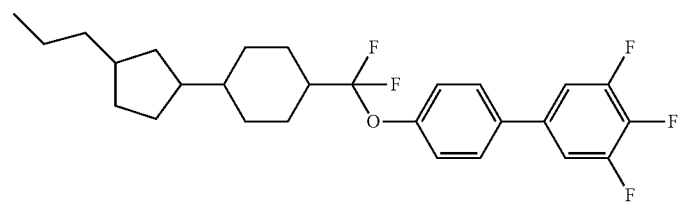 [SMILES: CCCC1CCC(C2CCC(C(F)(F)Oc3ccc(-c4cc(F)c(F)c(F)c4)cc3)CC2)C1] |
| 215 | 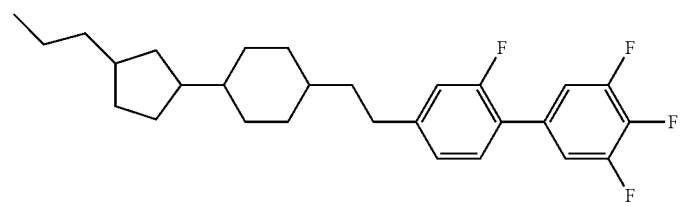 |
| 216 | 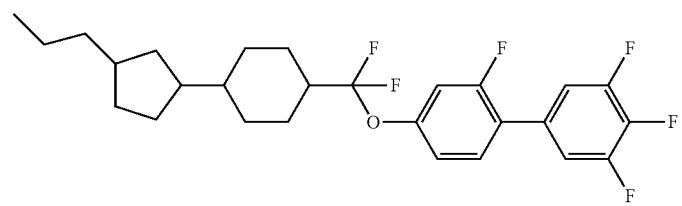 [SMILES: CCCC1CCC(C2CCC(C(F)(F)Oc3ccc(-c4cc(F)c(F)c(F)c4)c(F)c3)CC2)C1] |
| 217 | 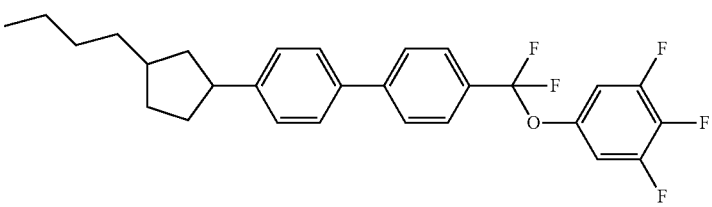 [SMILES: CCCCC1CCC(c2ccc(-c3ccc(C(F)(F)Oc4cc(F)c(F)c(F)c4)cc3)cc2)C1] |
| 218 | 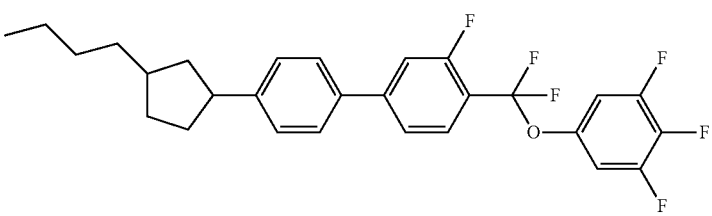 |
| 219 | 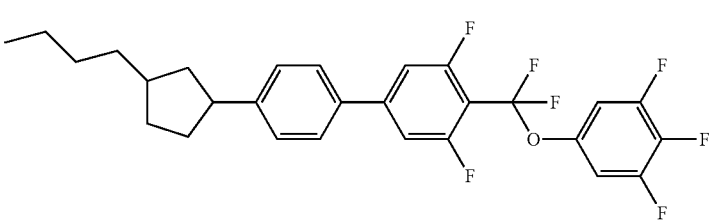 [SMILES: CCCCC1CCC(c2ccc(-c3cc(F)c(C(F)(F)Oc4cc(F)c(F)c(F)c4)c(F)c3)cc2)C1] |

| No. | |
|---|---|
| 220 | 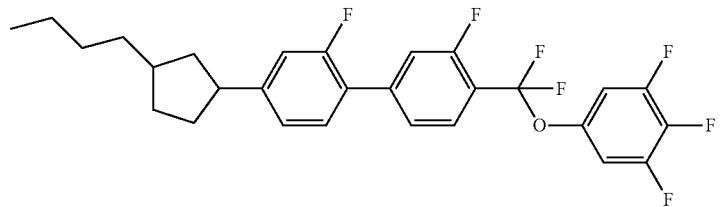 [SMILES: CCCCC1CCC(c2ccc(-c3ccc(C(F)(F)Oc4cc(F)c(F)c(F)c4)c(F)c3)c(F)c2)C1] |
| 221 | 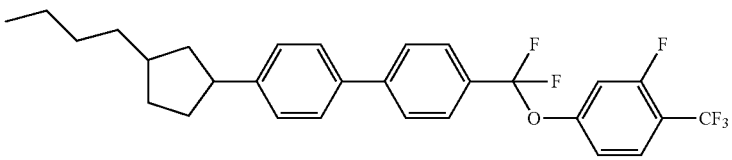 [SMILES: CCCCC1CCC(c2ccc(-c3ccc(C(F)(F)Oc4ccc(C(F)(F)F)c(F)c4)cc3)cc2)C1] |
| 222 | 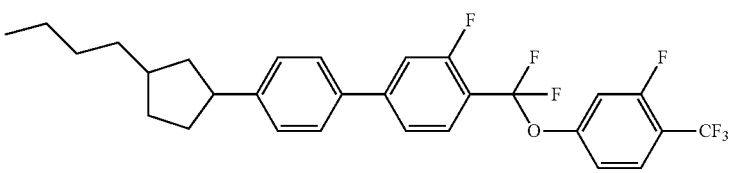 |
| 223 | 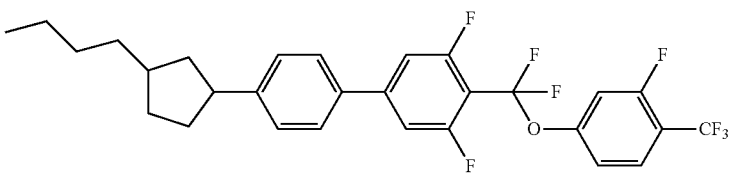 [SMILES: CCCCC1CCC(c2ccc(-c3cc(F)c(C(F)(F)Oc4ccc(C(F)(F)F)c(F)c4)c(F)c3)cc2)C1] |
| 224 | 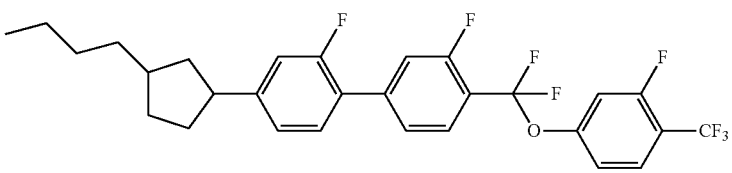 [SMILES: CCCCC1CCC(c2ccc(-c3ccc(C(F)(F)Oc4ccc(C(F)(F)F)c(F)c4)c(F)c3)c(F)c2)C1] |
| 225 | 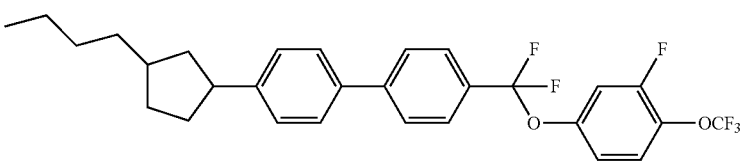 [SMILES: CCCCC1CCC(c2ccc(-c3ccc(C(F)(F)Oc4ccc(OC(F)(F)F)c(F)c4)cc3)cc2)C1] |
| 226 | 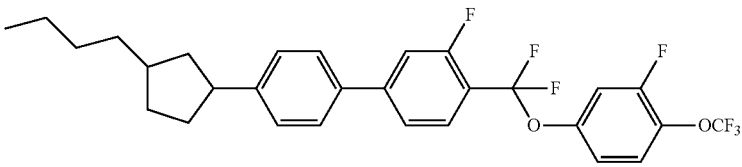 |
| 227 | 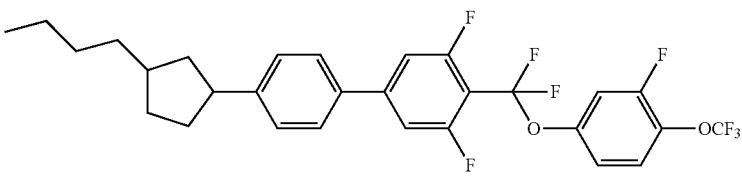 [SMILES: CCCCC1CCC(c2ccc(-c3cc(F)c(C(F)(F)Oc4ccc(OC(F)(F)F)c(F)c4)c(F)c3)cc2)C1] |

| No. | |
|---|---|
| 228 | 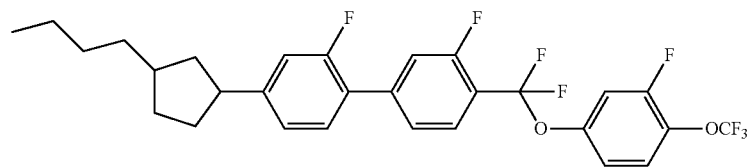 |
| 229 | 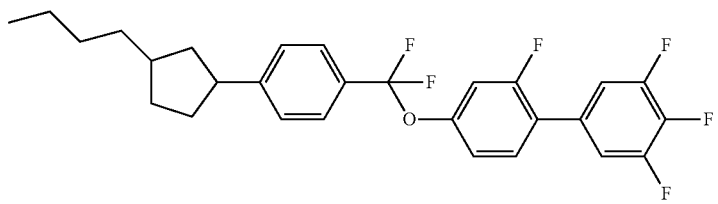 [SMILES: CCCCC1CCC(c2ccc(C(F)(F)Oc3ccc(-c4cc(F)c(F)c(F)c4)c(F)c3)cc2)C1] |
| 230 | 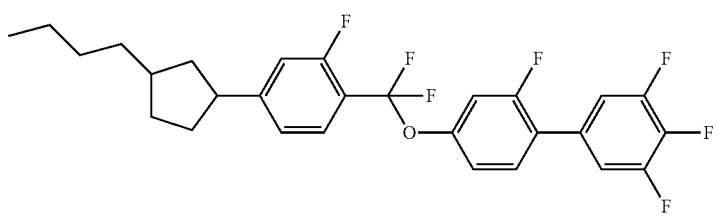 |
| 231 | 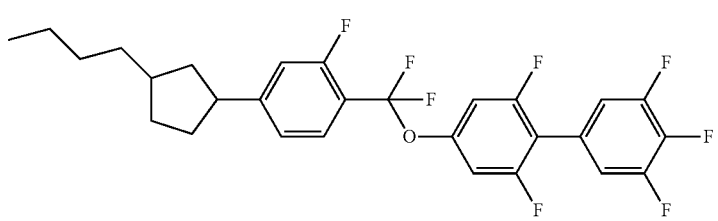 [SMILES: CCCCC1CCC(c2ccc(C(F)(F)Oc3cc(F)c(-c4cc(F)c(F)c(F)c4)c(F)c3)c(F)c2)C1] |
| 232 | 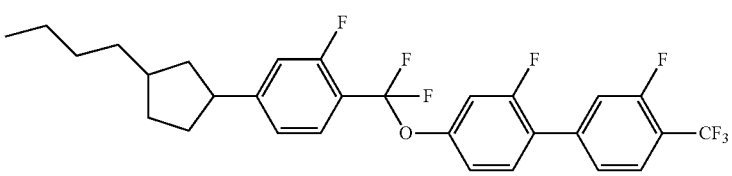 [SMILES: CCCCC1CCC(c2ccc(C(F)(F)Oc3ccc(-c4ccc(C(F)(F)F)c(F)c4)c(F)c3)c(F)c2)C1] |
| 233 | 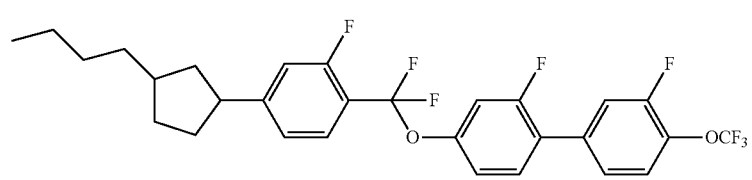 [SMILES: CCCCC1CCC(c2ccc(C(F)(F)Oc3ccc(-c4ccc(OC(F)(F)F)c(F)c4)c(F)c3)c(F)c2)C1] |
| 234 | 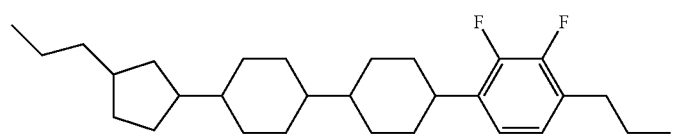 |
| 235 | 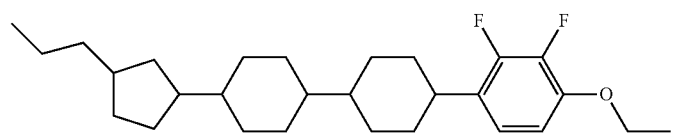 [SMILES: CCCC1CCC(C2CCC(C3CCC(c4ccc(OCC)c(F)c4F)CC3)CC2)C1] |
| 236 | 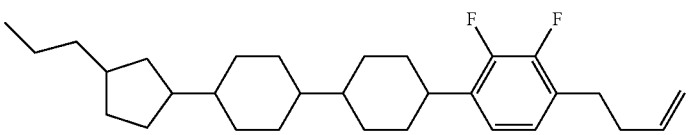 [SMILES: C=CCCc1ccc(C2CCC(C3CCC(C4CCC(CCC)C4)CC3)CC2)c(F)c1F] |

US 8,999,197 B2
| No. |
|---|
| 237 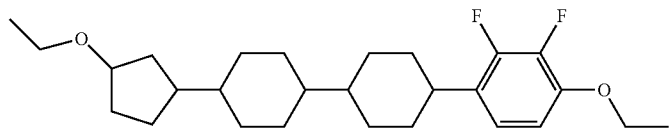 |
| 238 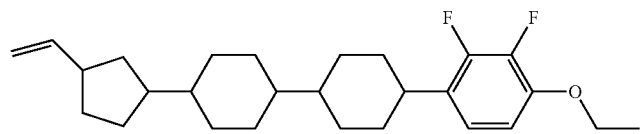 |
| 239 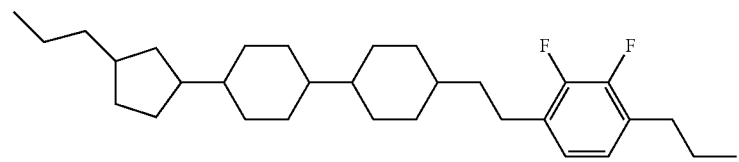 |
| 240 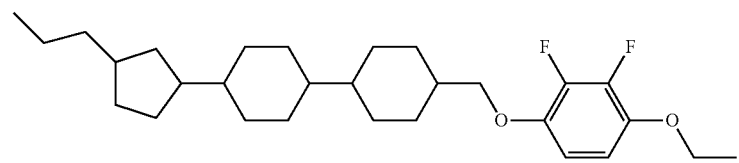 |
| 241 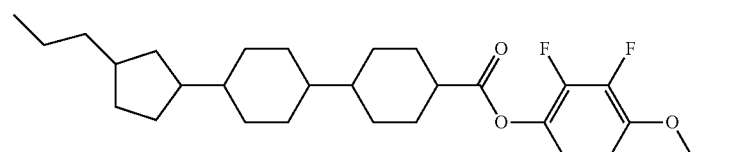 |
| 242 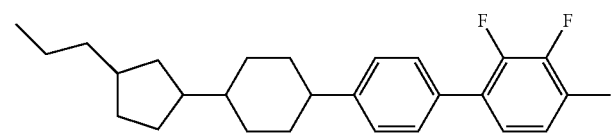 |
| 243 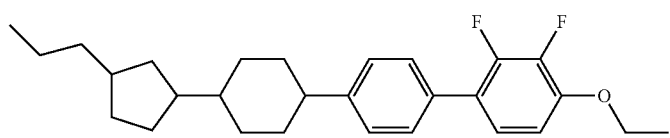 |
| 244 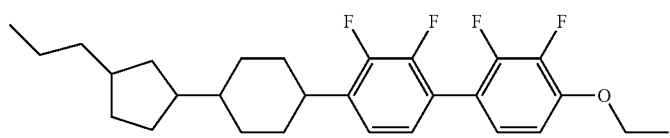 |
| 245 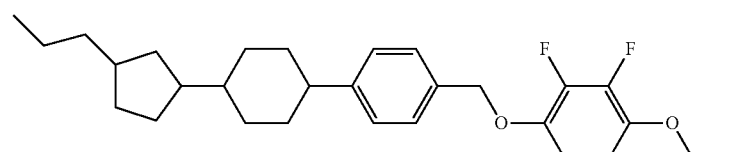 |
| 246 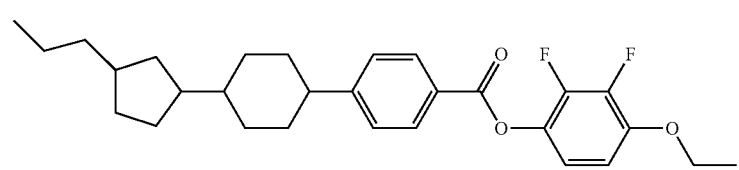 [SMILES: CCCC1CCC(C2CCC(c3ccc(C(=O)Oc4ccc(OCC)c(F)c4F)cc3)CC2)C1] |

| No. |
| --- |
| 247 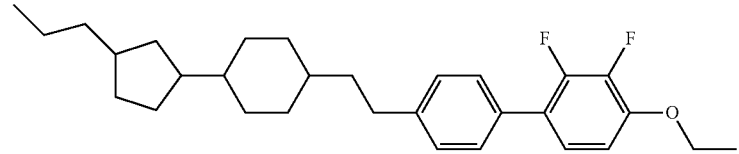 [SMILES: CCCC1CCC(C2CCC(CCc3ccc(-c4ccc(OCC)c(F)c4F)cc3)CC2)C1] |
| 248 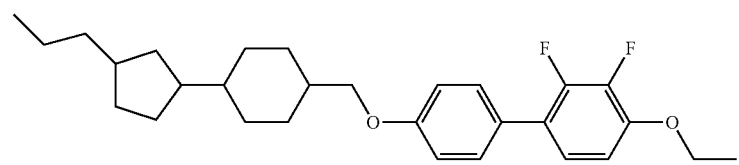 [SMILES: CCCC1CCC(C2CCC(COc3ccc(-c4ccc(OCC)c(F)c4F)cc3)CC2)C1] |
| 249 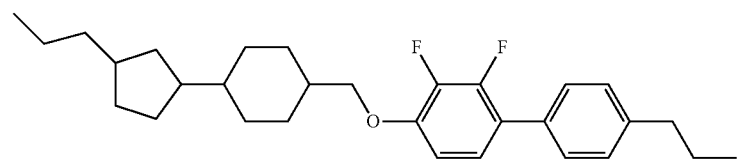 |
| 250 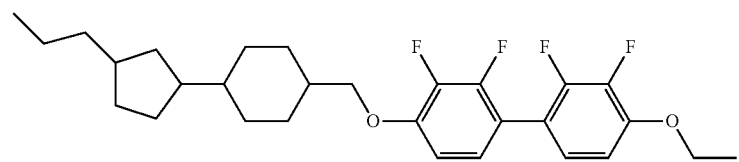 [SMILES: CCCC1CCC(C2CCC(COc3ccc(-c4ccc(OCC)c(F)c4F)c(F)c3F)CC2)C1] |
| 251 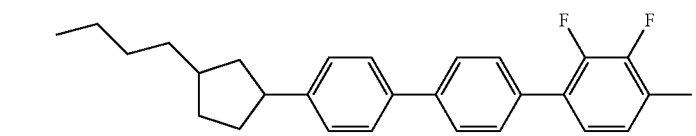 |
| 252 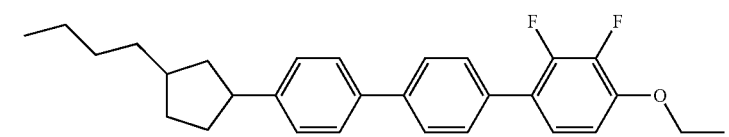 [SMILES: CCCCC1CCC(c2ccc(-c3ccc(-c4ccc(OCC)c(F)c4F)cc3)cc2)C1] |
| 253 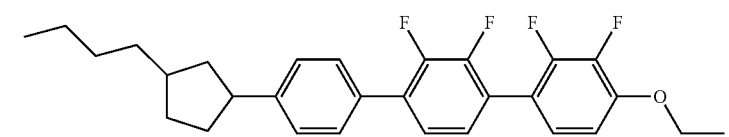 [SMILES: CCCCC1CCC(c2ccc(-c3ccc(-c4ccc(OCC)c(F)c4F)c(F)c3F)cc2)C1] |
| 254 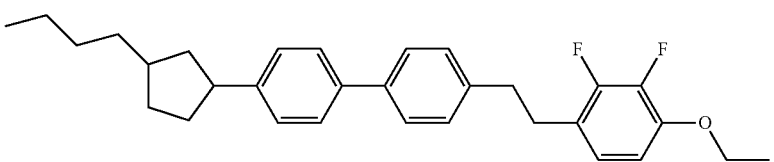 [SMILES: CCCCC1CCC(c2ccc(-c3ccc(CCc4ccc(OCC)c(F)c4F)cc3)cc2)C1] |
| 255 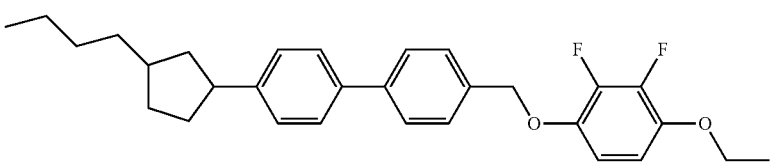 [SMILES: CCCCC1CCC(c2ccc(-c3ccc(COc4ccc(OCC)c(F)c4F)cc3)cc2)C1] |
| 256 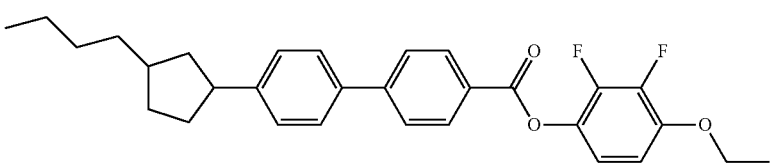 [SMILES: CCCCC1CCC(c2ccc(-c3ccc(C(=O)Oc4ccc(OCC)c(F)c4F)cc3)cc2)C1] |

| No. |
| --- |
| 257 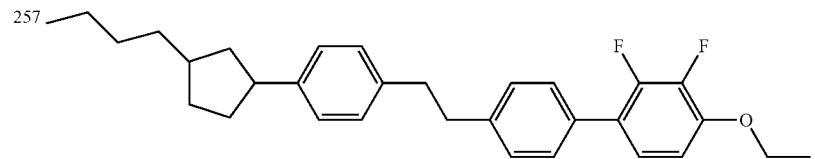 |
| 258 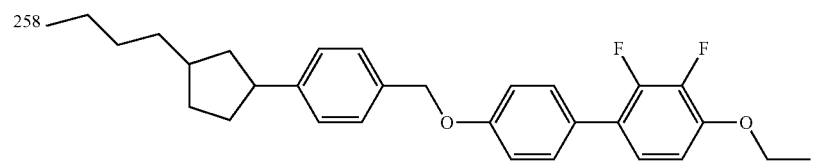 |
| 259 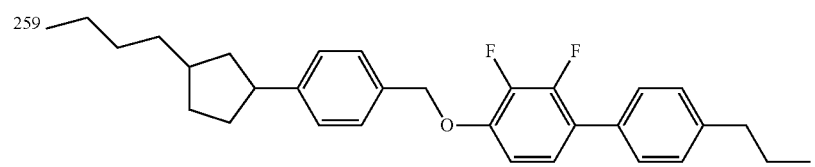 |
| 260 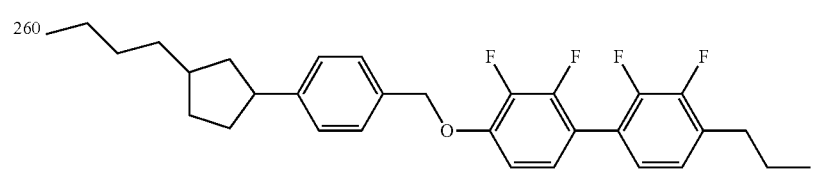 |
| 261 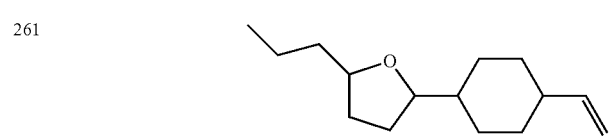 |
| 262 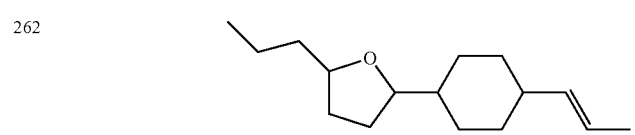 |
| 263 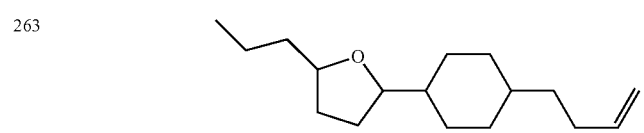 |
| 264 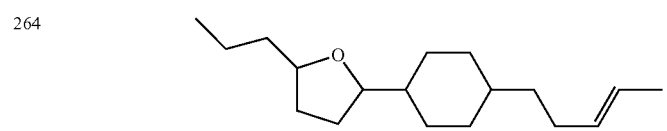 |
| 265 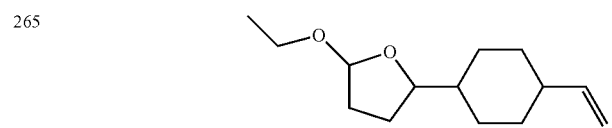 |
| 266 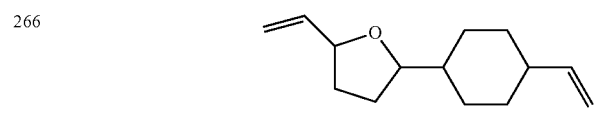 |
| 267 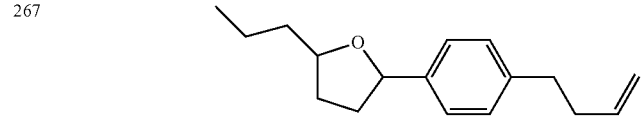 |

-continued
| No. | |
|---|---|
| 268 | 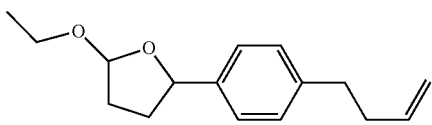 [SMILES: C=CCCc1ccc(C2CCC(CCC)O2)cc1] |
| 269 | 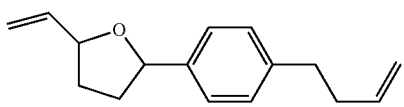 [SMILES: C=CCCc1ccc(C2CCC(C=C)O2)cc1] |
| 270 | 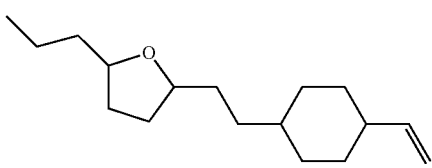 [SMILES: C=CC1CCC(CCC2CCC(CCC)O2)CC1] |
| 271 | 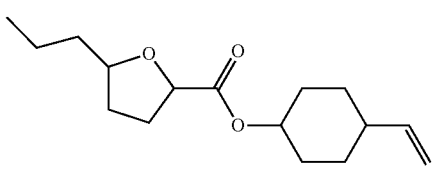 [SMILES: C=CC1CCC(OC(=O)C2CCC(CCC)O2)CC1] |
| 272 | 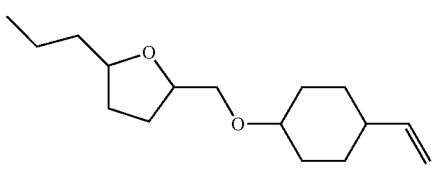 [SMILES: C=CC1CCC(OCC2CCC(CCC)O2)CC1] |
| 273 | 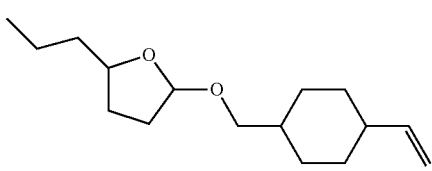 |
| 274 | 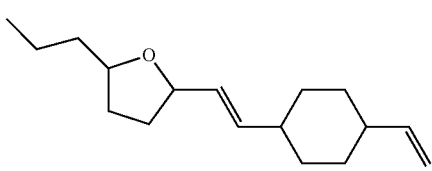 [SMILES: C=CC1CCC(/C=C/C2CCC(CCC)O2)CC1] |
| 275 | 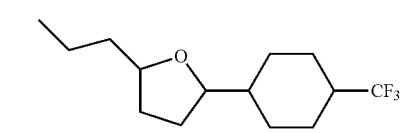 [SMILES: CCCC1CCC(C2CCC(C(F)(F)F)CC2)O1] |
| 276 | 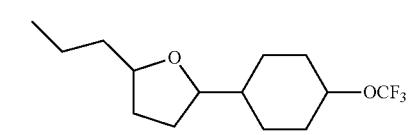 |
| 277 | 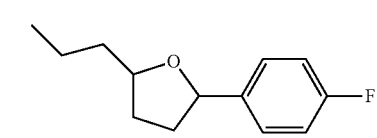 |

| No. | |
|---|---|
| 278 | 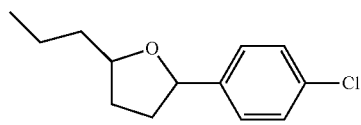 |
| 279 | 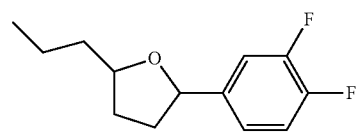 |
| 280 | 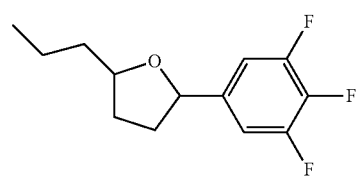 [SMILES: CCCC1CCC(c2cc(F)c(F)c(F)c2)O1] |
| 281 | 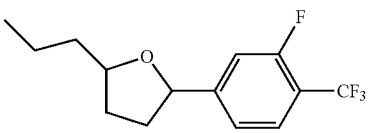 [SMILES: CCCC1CCC(c2ccc(C(F)(F)F)c(F)c2)O1] |
| 282 | 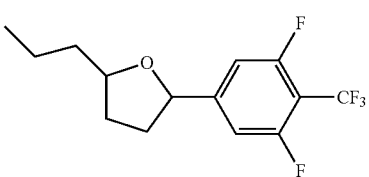 |
| 283 | 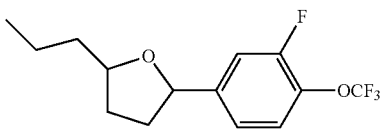 |
| 284 | 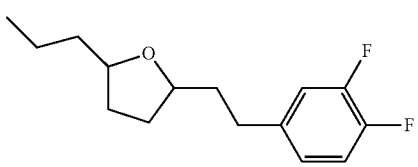 [SMILES: CCCC1CCC(CCc2ccc(F)c(F)c2)O1] |
| 285 | 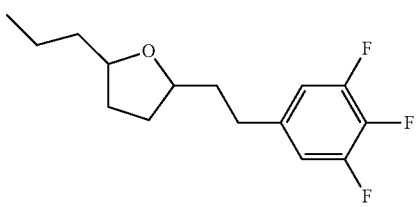 |
| 286 | 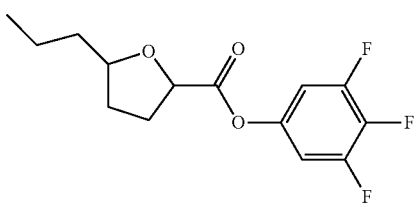 [SMILES: CCCC1CCC(C(=O)Oc2cc(F)c(F)c(F)c2)O1] |

-continued
| No. | |
|---|---|
| 287 | 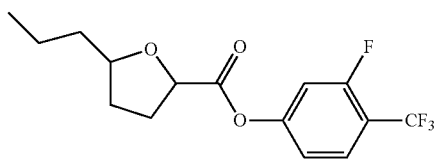 [SMILES: CCCC1CCC(C(=O)Oc2ccc(C(F)(F)F)c(F)c2)O1] |
| 288 | 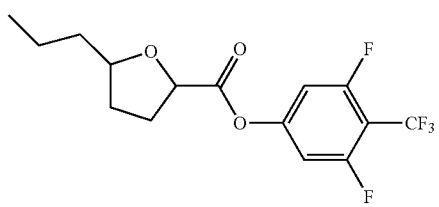 [SMILES: CCCC1CCC(C(=O)Oc2cc(F)c(C(F)(F)F)c(F)c2)O1] |
| 289 | 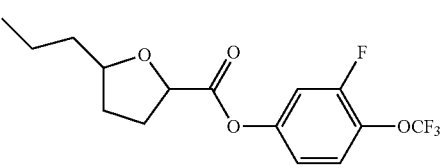 [SMILES: CCCC1CCC(C(=O)Oc2ccc(OC(F)(F)F)c(F)c2)O1] |
| 290 | 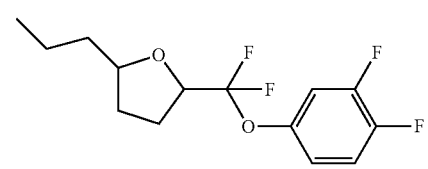 |
| 291 | 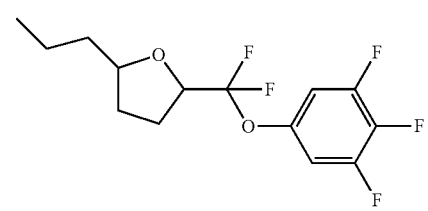 |
| 292 | 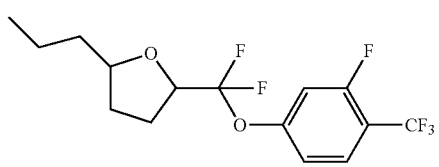 [SMILES: CCCC1CCC(C(F)(F)Oc2ccc(C(F)(F)F)c(F)c2)O1] |
| 293 | 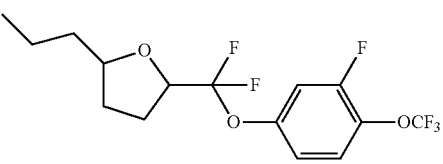 [SMILES: CCCC1CCC(C(F)(F)Oc2ccc(OC(F)(F)F)c(F)c2)O1] |
| 294 | 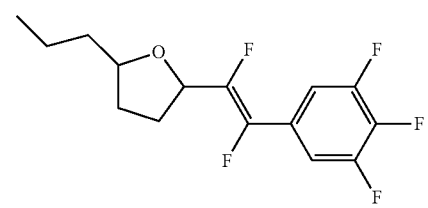 [SMILES: CCCC1CCC(/C(F)=C(\F)c2cc(F)c(F)c(F)c2)O1] |
| 295 | 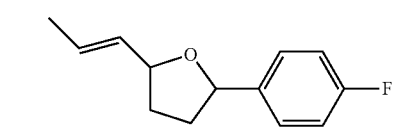 |

-continued
| No. | |
|---|---|
| 296 | 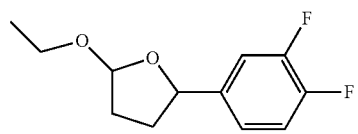 [SMILES: CCOC1CCC(c2ccc(F)c(F)c2)O1] |
| 297 | 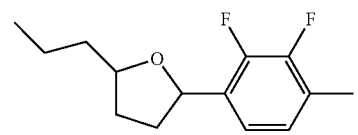 [SMILES: CCCC1CCC(c2ccc(C)c(F)c2F)O1] |
| 298 | 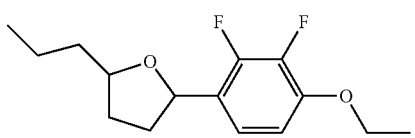 [SMILES: CCCC1CCC(c2ccc(OCC)c(F)c2F)O1] |
| 299 | 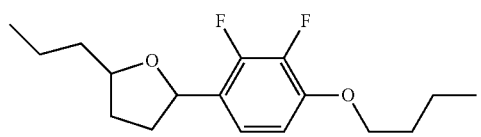 [SMILES: CCCCOc1ccc(C2CCC(CCC)O2)c(F)c1F] |
| 300 | 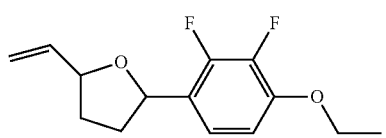 |
| 301 | 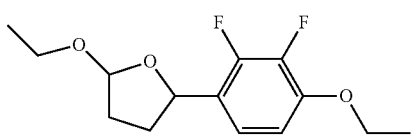 [SMILES: CCOc1ccc(C2CCC(OCC)O2)c(F)c1F] |
| 302 | 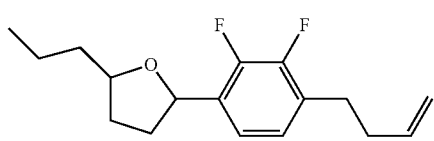 [SMILES: C=CCCc1ccc(C2CCC(CCC)O2)c(F)c1F] |
| 303 | 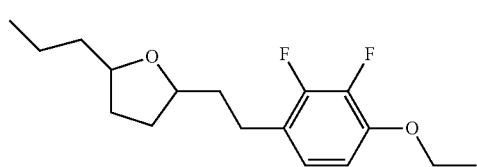 |
| 304 | 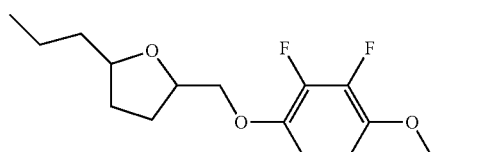 |
| 305 | 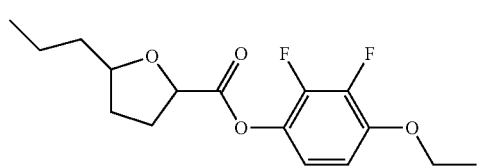 |

| No. | |
|---|---|
| 306 | 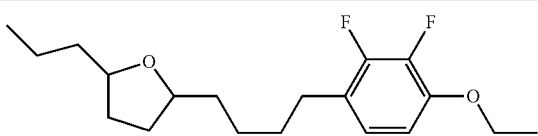 [SMILES: CCCC1CCC(CCCCc2ccc(OCC)c(F)c2F)O1] |
| 307 | 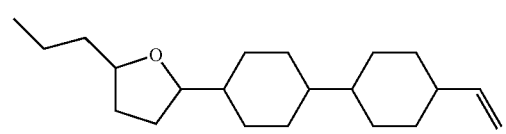 |
| 308 | 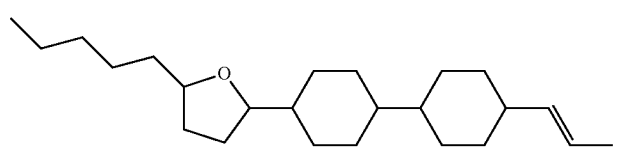 |
| 309 | 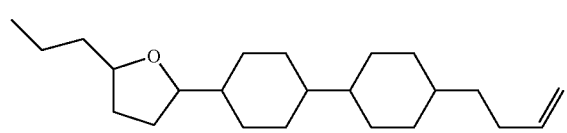 |
| 310 | 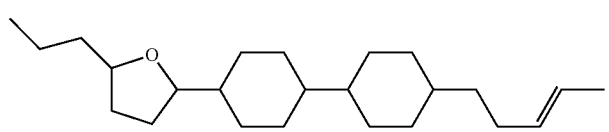 |
| 311 | 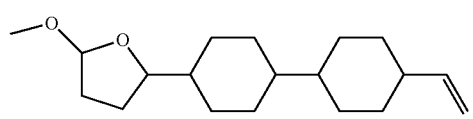 |
| 312 | 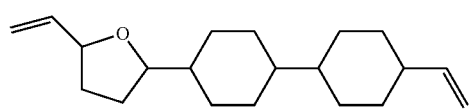 |
| 313 | 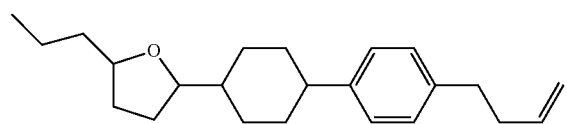 [SMILES: C=CCCc1ccc(C2CCC(C3CCC(CCC)O3)CC2)cc1] |
| 314 | 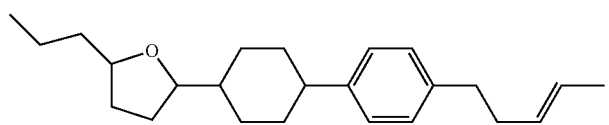 [SMILES: C/C=C/CCc1ccc(C2CCC(C3CCC(CCC)O3)CC2)cc1] |
| 315 | 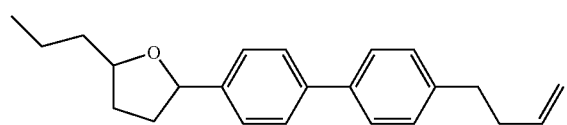 [SMILES: C=CCCc1ccc(-c2ccc(C3CCC(CCC)O3)cc2)cc1] |
| 316 | 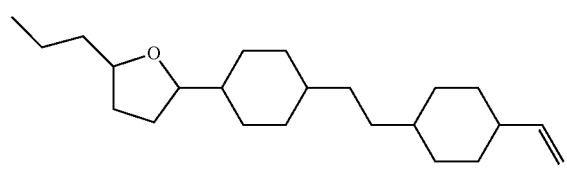 |

| No. | |
|---|---|
| 317 | 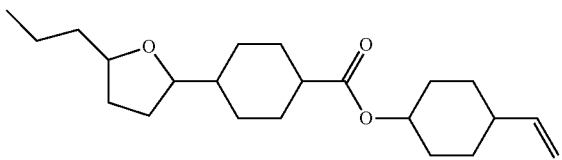 [SMILES: C=CC1CCC(OC(=O)C2CCC(C3CCC(CCC)O3)CC2)CC1] |
| 318 | 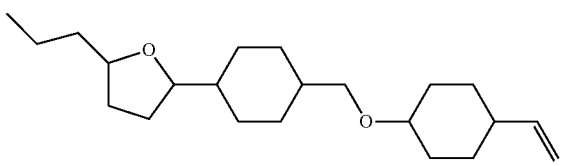 |
| 319 | 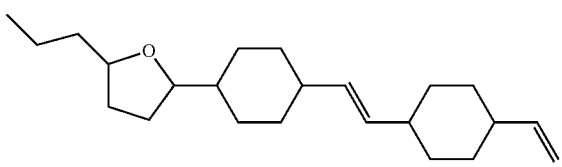 |
| 320 | 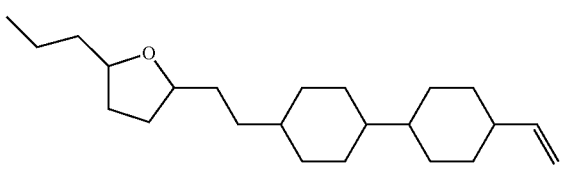 |
| 321 | 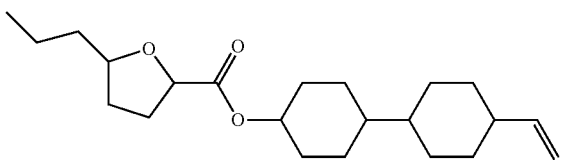 [SMILES: C=CC1CCC(C2CCC(OC(=O)C3CCC(CCC)O3)CC2)CC1] |
| 322 | 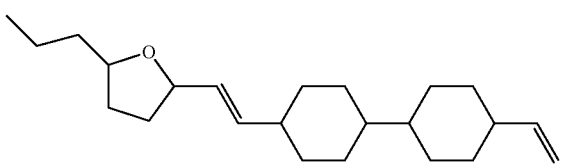 |
| 323 | 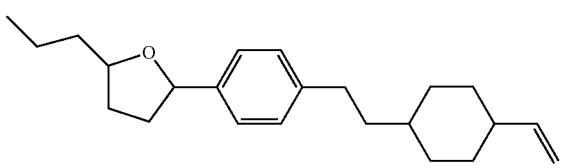 [SMILES: C=CC1CCC(CCc2ccc(C3CCC(CCC)O3)cc2)CC1] |
| 324 | 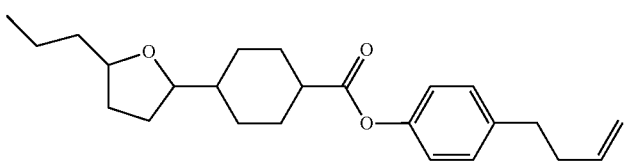 [SMILES: C=CCCc1ccc(OC(=O)C2CCC(C3CCC(CCC)O3)CC2)cc1] |
| 325 | 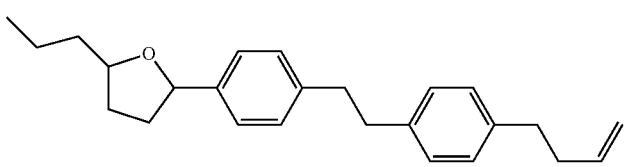 [SMILES: C=CCCc1ccc(CCc2ccc(C3CCC(CCC)O3)cc2)cc1] |

| No. | |
|---|---|
| 326 | 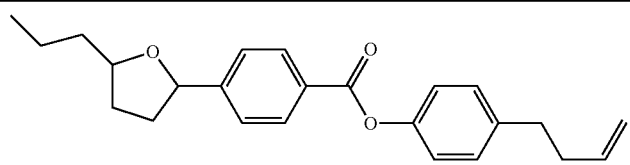 |
| 327 | 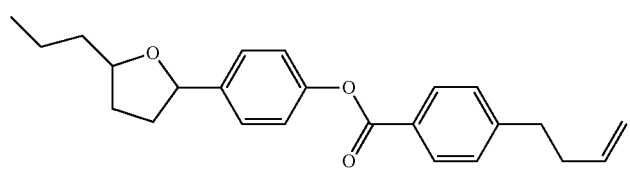 [SMILES: C=CCCc1ccc(C(=O)Oc2ccc(C3CCC(CCC)O3)cc2)cc1] |
| 328 | 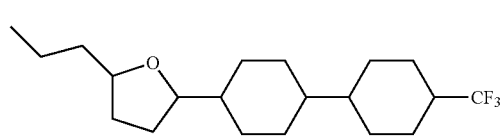 |
| 329 | 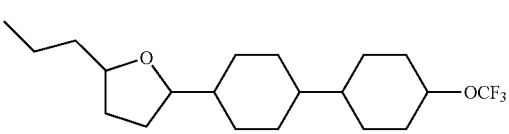 [SMILES: CCCC1CCC(C2CCC(C3CCC(OC(F)(F)F)CC3)CC2)O1] |
| 330 | 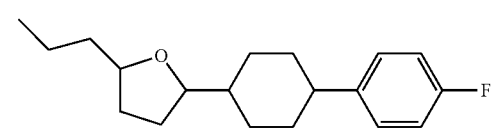 [SMILES: CCCC1CCC(C2CCC(c3ccc(F)cc3)CC2)O1] |
| 331 | 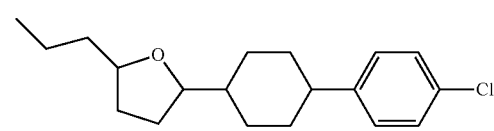 [SMILES: CCCC1CCC(C2CCC(c3ccc(Cl)cc3)CC2)O1] |
| 332 | 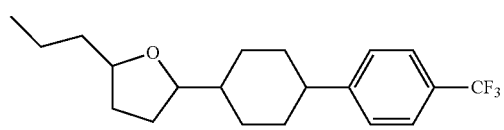 |
| 333 | 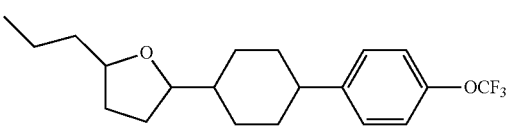 [SMILES: CCCC1CCC(C2CCC(c3ccc(OC(F)(F)F)cc3)CC2)O1] |
| 334 | 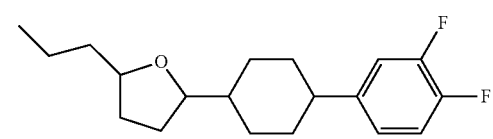 |
| 335 | 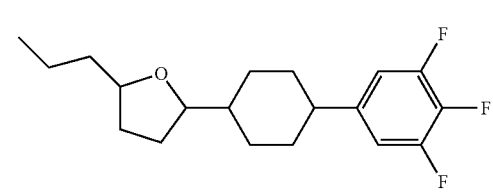 [SMILES: CCCC1CCC(C2CCC(c3cc(F)c(F)c(F)c3)CC2)O1] |
| 336 | 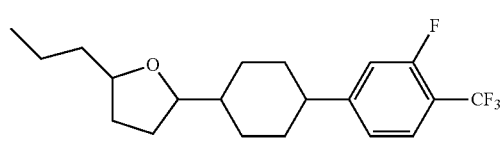 |

-continued
| No. | |
|---|---|
| 337 | 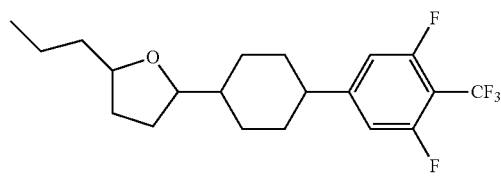 [SMILES: CCCC1CCC(C2CCC(c3cc(F)c(C(F)(F)F)c(F)c3)CC2)O1] |
| 338 | 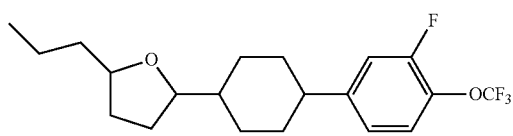 [SMILES: CCCC1CCC(C2CCC(c3ccc(OC(F)(F)F)c(F)c3)CC2)O1] |
| 339 | 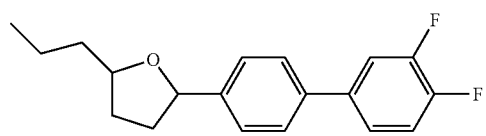 [SMILES: CCCC1CCC(c2ccc(-c3ccc(F)c(F)c3)cc2)O1] |
| 340 | 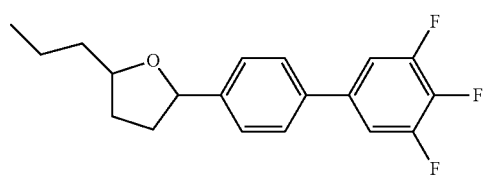 [SMILES: CCCC1CCC(c2ccc(-c3cc(F)c(F)c(F)c3)cc2)O1] |
| 341 | 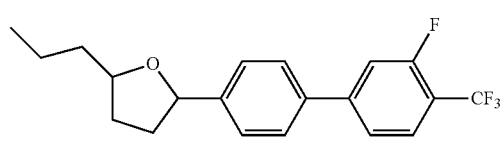 |
| 342 | 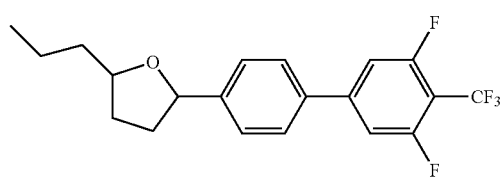 [SMILES: CCCC1CCC(c2ccc(-c3cc(F)c(C(F)(F)F)c(F)c3)cc2)O1] |
| 343 | 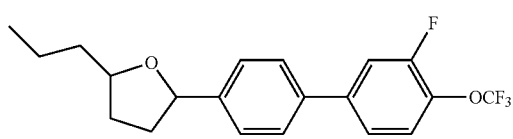 [SMILES: CCCC1CCC(c2ccc(-c3ccc(OC(F)(F)F)c(F)c3)cc2)O1] |
| 344 | 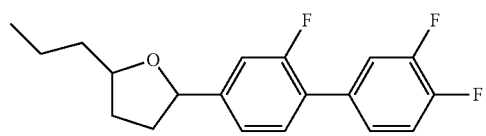 |
| 345 | 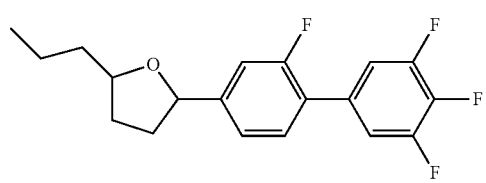 |

-continued
| No. | |
|---|---|
| 346 | 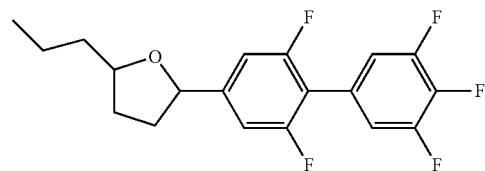 |
| 347 | 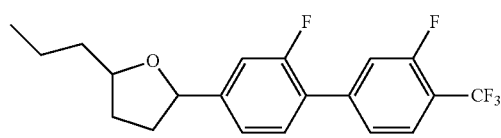 [SMILES: CCCC1CCC(c2ccc(-c3ccc(C(F)(F)F)c(F)c3)c(F)c2)O1] |
| 378 | 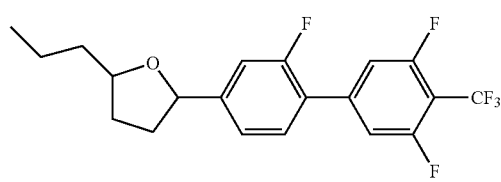 [SMILES: CCCC1CCC(c2ccc(-c3cc(F)c(C(F)(F)F)c(F)c3)c(F)c2)O1] |
| 349 | 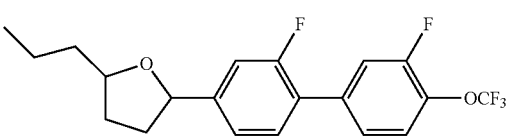 [SMILES: CCCC1CCC(c2ccc(-c3ccc(OC(F)(F)F)c(F)c3)c(F)c2)O1] |
| 350 | 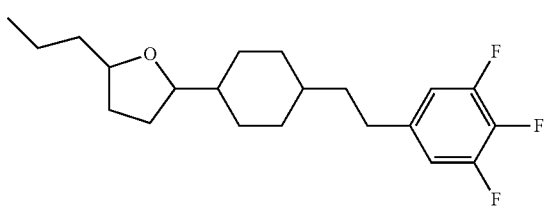 |
| 351 | 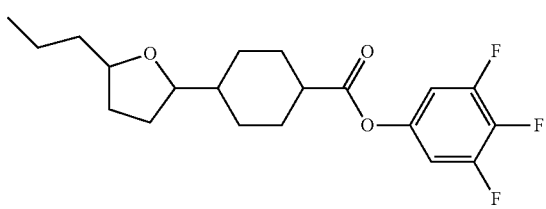 [SMILES: CCCC1CCC(C2CCC(C(=O)Oc3cc(F)c(F)c(F)c3)CC2)O1] |
| 352 | 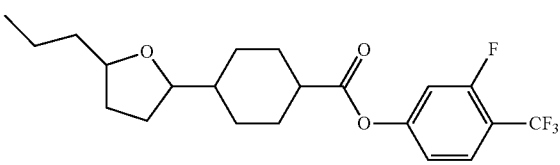 [SMILES: CCCC1CCC(C2CCC(C(=O)Oc3ccc(C(F)(F)F)c(F)c3)CC2)O1] |
| 353 | 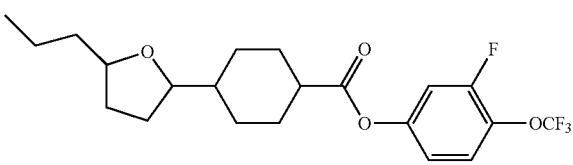 |
| 354 | 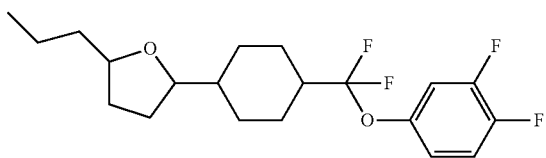 [SMILES: CCCC1CCC(C2CCC(C(F)(F)Oc3ccc(F)c(F)c3)CC2)O1] |

-continued
| No. | |
|---|---|
| 355 | 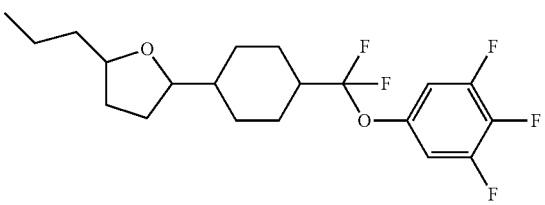 [SMILES: CCCC1CCC(C2CCC(C(F)(F)Oc3cc(F)c(F)c(F)c3)CC2)O1] |
| 356 | 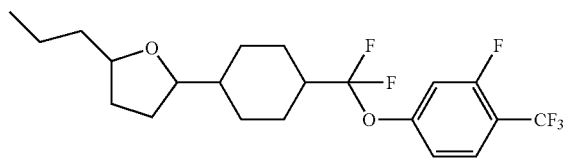 |
| 357 | 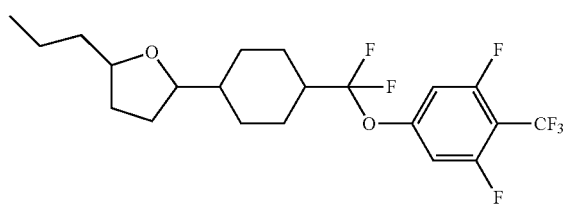 |
| 358 | 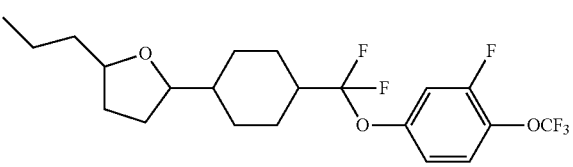 |
| 359 | 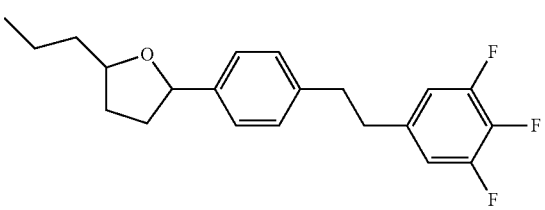 [SMILES: CCCC1CCC(c2ccc(CCc3cc(F)c(F)c(F)c3)cc2)O1] |
| 360 | 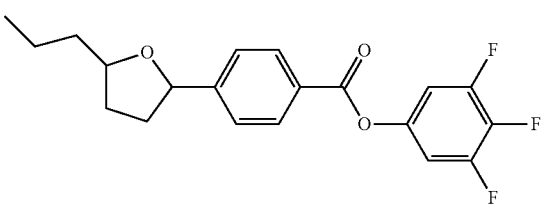 [SMILES: CCCC1CCC(c2ccc(C(=O)Oc3cc(F)c(F)c(F)c3)cc2)O1] |
| 361 | 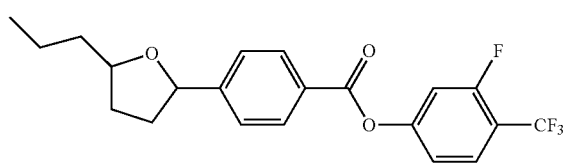 [SMILES: CCCC1CCC(c2ccc(C(=O)Oc3ccc(C(F)(F)F)c(F)c3)cc2)O1] |
| 362 | 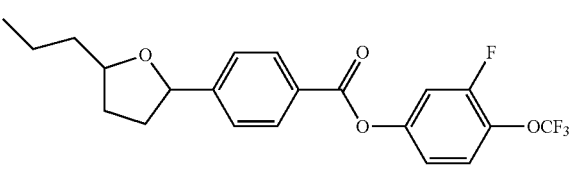 [SMILES: CCCC1CCC(c2ccc(C(=O)Oc3ccc(OC(F)(F)F)c(F)c3)cc2)O1] |

| No. | |
|---|---|
| 363 | 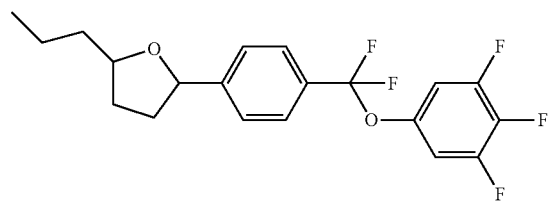 [SMILES: CCCC1CCC(c2ccc(C(F)(F)Oc3cc(F)c(F)c(F)c3)cc2)O1] |
| 364 | 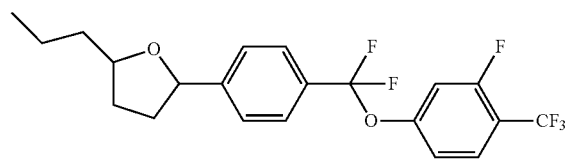 [SMILES: CCCC1CCC(c2ccc(C(F)(F)Oc3ccc(C(F)(F)F)c(F)c3)cc2)O1] |
| 365 | 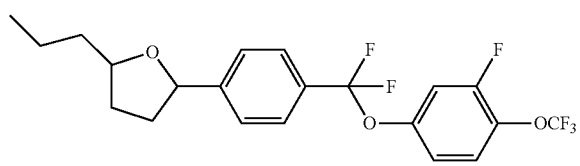 [SMILES: CCCC1CCC(c2ccc(C(F)(F)Oc3ccc(OC(F)(F)F)c(F)c3)cc2)O1] |
| 366 | 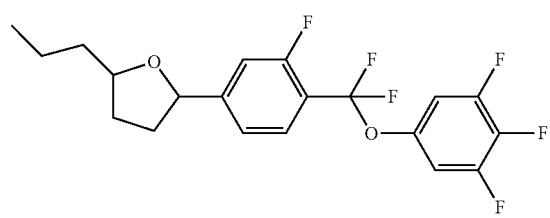 |
| 367 | 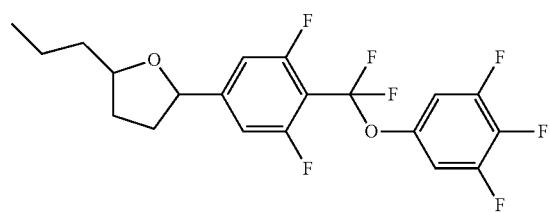 [SMILES: CCCC1CCC(c2ccc(C(F)(F)Oc3cc(F)c(F)c(F)c3)c(F)c2)O1] |
| 368 | 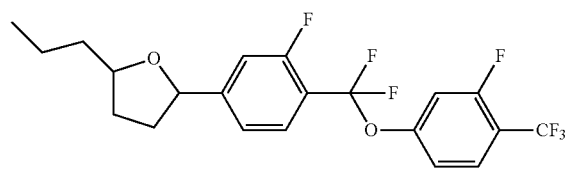 [SMILES: CCCC1CCC(c2ccc(C(F)(F)Oc3ccc(C(F)(F)F)c(F)c3)c(F)c2)O1] |
| 369 | 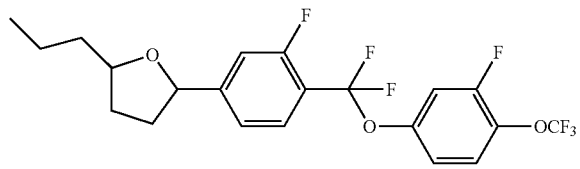 [SMILES: CCCC1CCC(c2ccc(C(F)(F)Oc3ccc(OC(F)(F)F)c(F)c3)c(F)c2)O1] |
| 370 | 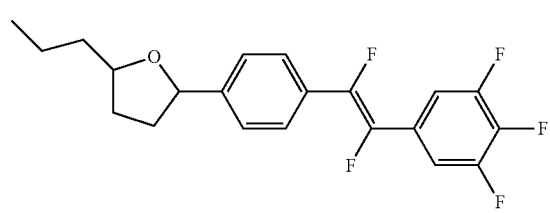 [SMILES: CCCC1CCC(c2ccc(/C(F)=C(\F)c3cc(F)c(F)c(F)c3)cc2)O1] |

-continued
| No. | |
|---|---|
| 371 | 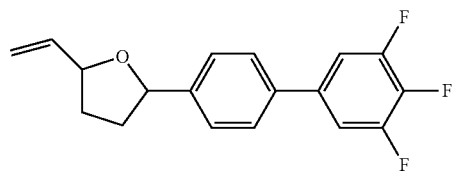 |
| 372 | 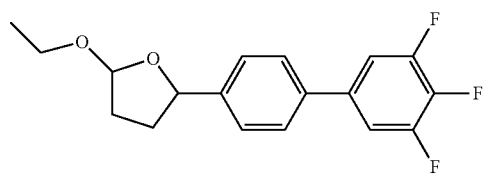 |
| 373 | 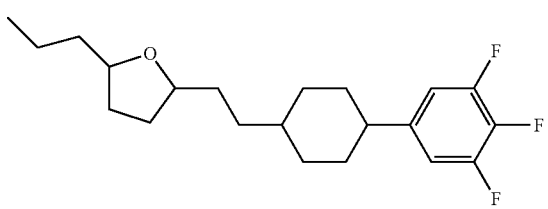 [SMILES: CCCC1CCC(CCC2CCC(c3cc(F)c(F)c(F)c3)CC2)O1] |
| 374 | 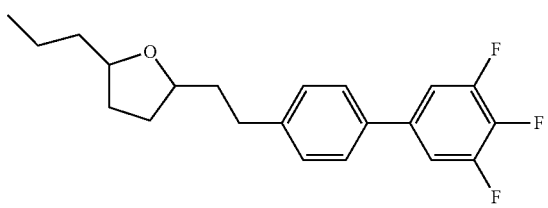 [SMILES: CCCC1CCC(CCc2ccc(-c3cc(F)c(F)c(F)c3)cc2)O1] |
| 375 | 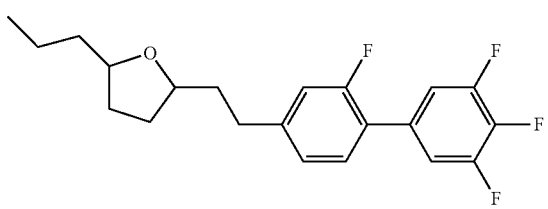 [SMILES: CCCC1CCC(CCc2ccc(-c3cc(F)c(F)c(F)c3)c(F)c2)O1] |
| 376 | 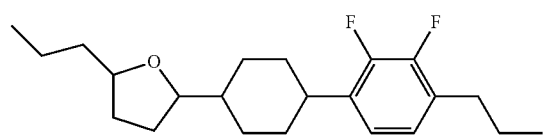 [SMILES: CCCc1ccc(C2CCC(C3CCC(CCC)O3)CC2)c(F)c1F] |
| 377 | 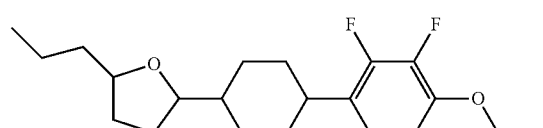 |
| 378 | 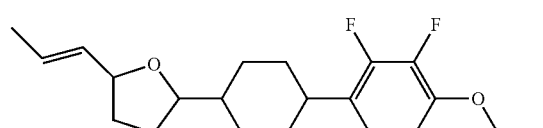 |
| 379 | 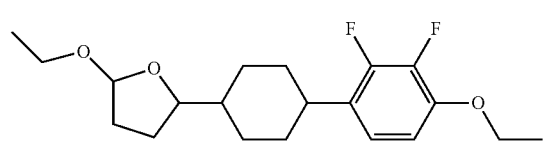 |

-continued
| No. | |
|---|---|
| 380 | 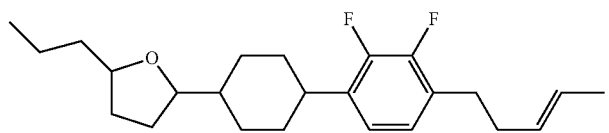 [SMILES: C/C=C/CCc1ccc(C2CCC(C3CCC(CCC)O3)CC2)c(F)c1F] |
| 381 | 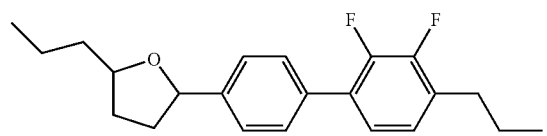 |
| 382 | 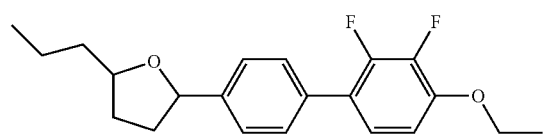 [SMILES: CCCC1CCC(c2ccc(-c3ccc(OCC)c(F)c3F)cc2)O1] |
| 383 | 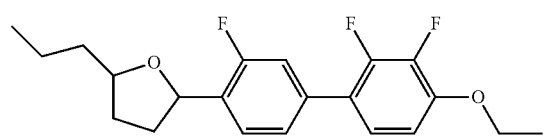 [SMILES: CCCC1CCC(c2ccc(-c3ccc(OCC)c(F)c3F)cc2F)O1] |
| 384 | 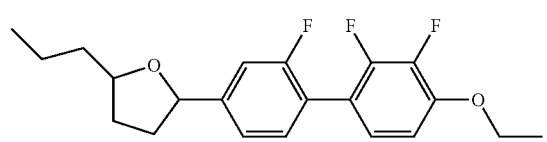 [SMILES: CCCC1CCC(c2ccc(-c3ccc(OCC)c(F)c3F)c(F)c2)O1] |
| 385 | 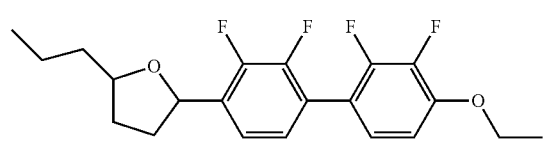 |
| 386 | 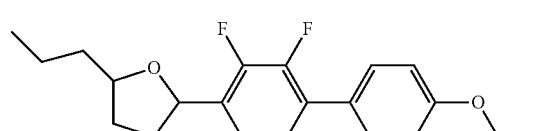 |
| 387 | 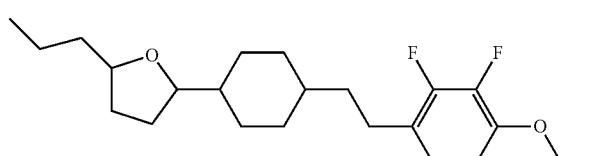 |
| 388 | 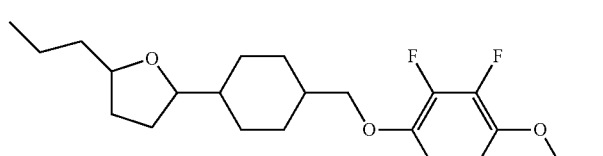 |
| 389 | 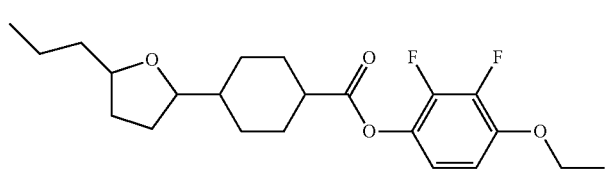 [SMILES: CCCC1CCC(C2CCC(C(=O)Oc3ccc(OCC)c(F)c3F)CC2)O1] |

-continued
| No. | |
|---|---|
| 390 | 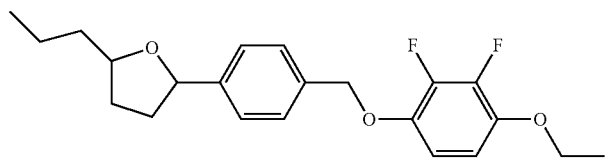 [SMILES: CCCC1CCC(c2ccc(COc3ccc(OCC)c(F)c3F)cc2)O1] |
| 391 | 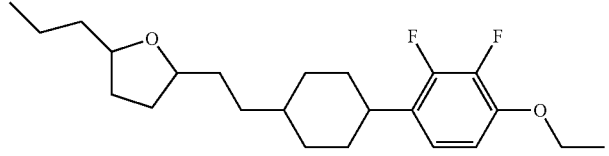 [SMILES: CCCC1CCC(CCC2CCC(c3ccc(OCC)c(F)c3F)CC2)O1] |
| 392 | 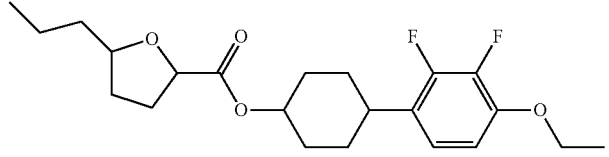 [SMILES: CCCC1CCC(C(=O)OC2CCC(c3ccc(OCC)c(F)c3F)CC2)O1] |
| 393 | 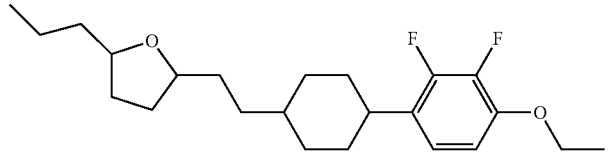 |
| 394 | 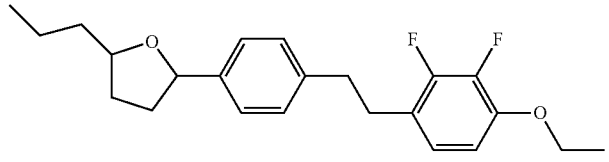 |
| 395 | 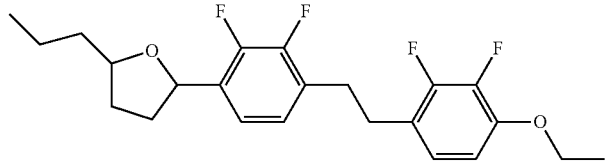 [SMILES: CCCC1CCC(c2ccc(CCc3ccc(OCC)c(F)c3F)c(F)c2F)O1] |
| 396 | 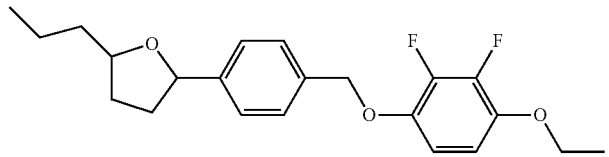 [SMILES: CCCC1CCC(c2ccc(COc3ccc(OCC)c(F)c3F)cc2)O1] |
| 397 | 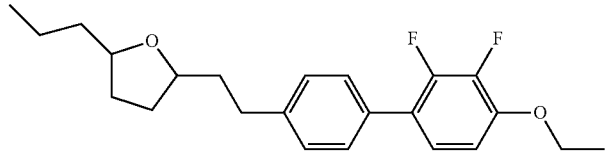 |
| 398 | 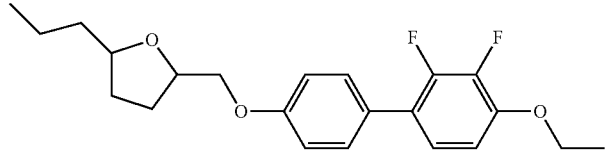 [SMILES: CCCC1CCC(COc2ccc(-c3ccc(OCC)c(F)c3F)cc2)O1] |

-continued
| No. | |
|---|---|
| 399 | 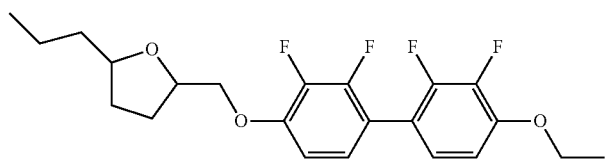 [SMILES: CCCC1CCC(COc2ccc(-c3ccc(OCC)c(F)c3F)c(F)c2F)O1] |
| 400 | 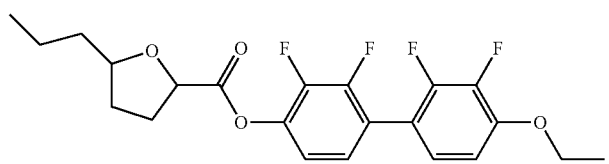 [SMILES: CCCC1CCC(C(=O)Oc2ccc(-c3ccc(OCC)c(F)c3F)c(F)c2F)O1] |
| 401 | 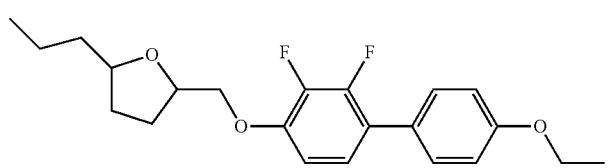 [SMILES: CCCC1CCC(COc2ccc(-c3ccc(OCC)cc3)c(F)c2F)O1] |
| 402 | 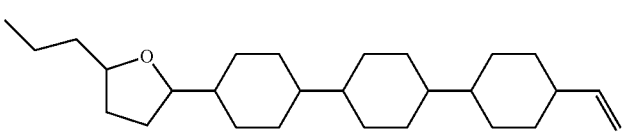 |
| 403 | 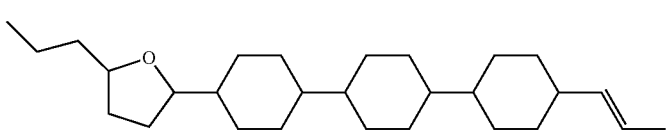 [SMILES: C/C=C/C1CCC(C2CCC(C3CCC(C4CCC(CCC)O4)CC3)CC2)CC1] |
| 404 | 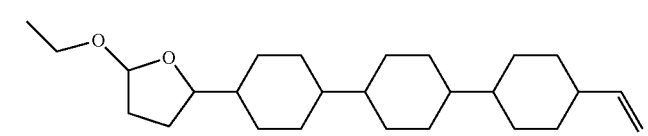 |
| 405 | 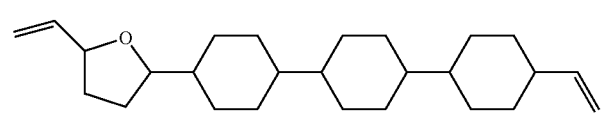 |
| 406 | 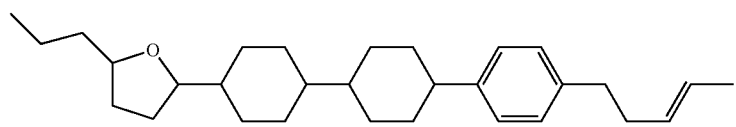 [SMILES: C/C=C/CCc1ccc(C2CCC(C3CCC(C4CCC(CCC)O4)CC3)CC2)cc1] |
| 407 | 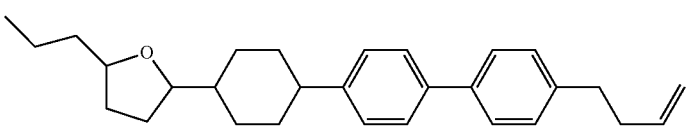 [SMILES: C=CCCc1ccc(-c2ccc(C3CCC(C4CCC(CCC)O4)CC3)cc2)cc1] |
| 408 | 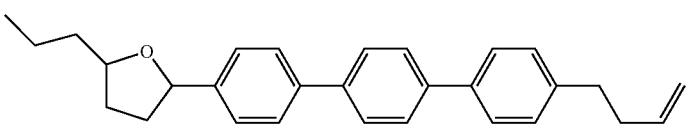 [SMILES: C=CCCc1ccc(-c2ccc(-c3ccc(C4CCC(CCC)O4)cc3)cc2)cc1] |
| 409 | 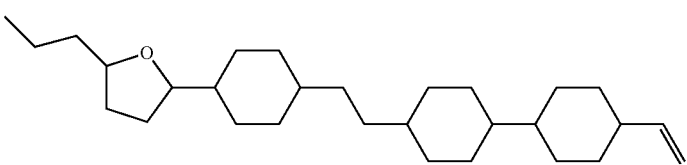 |

-continued
| No. | |
|---|---|
| 410 | 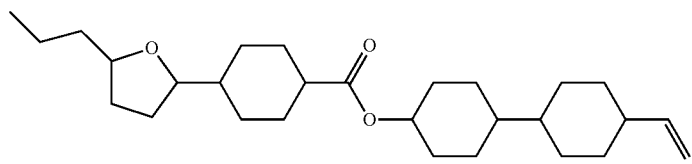 |
| 411 | 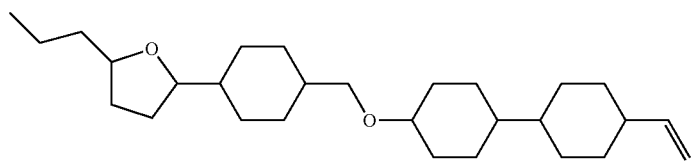 [SMILES: C=CC1CCC(C2CCC(CCC3CCC(C4CCC(CCC)O4)CC3)CC2)CC1] |
| 412 | 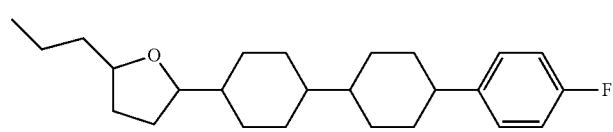 [SMILES: CCCC1CCC(C2CCC(C3CCC(c4ccc(F)cc4)CC3)CC2)O1] |
| 413 | 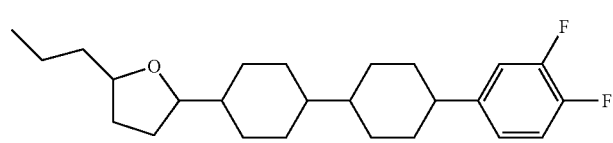 [SMILES: CCCC1CCC(C2CCC(C3CCC(c4ccc(F)c(F)c4)CC3)CC2)O1] |
| 414 | 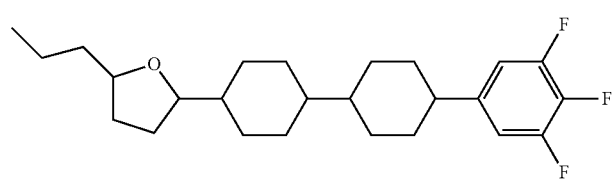 |
| 415 | 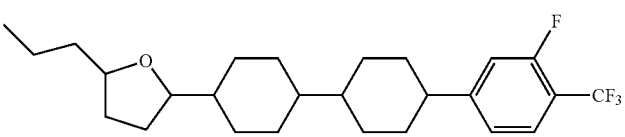 [SMILES: CCCC1CCC(C2CCC(C3CCC(c4ccc(C(F)(F)F)c(F)c4)CC3)CC2)O1] |
| 416 | 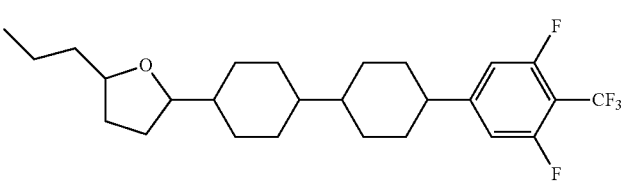 [SMILES: CCCC1CCC(C2CCC(C3CCC(c4cc(F)c(C(F)(F)F)c(F)c4)CC3)CC2)O1] |
| 417 | 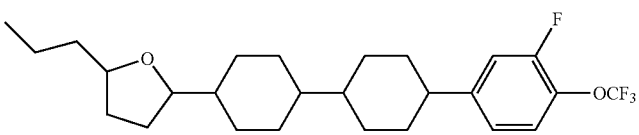 [SMILES: CCCC1CCC(C2CCC(C3CCC(c4ccc(OC(F)(F)F)c(F)c4)CC3)CC2)O1] |
| 418 | 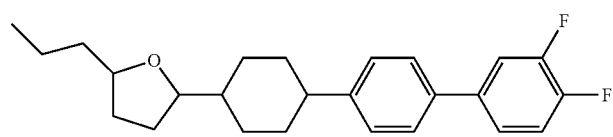 |
| 419 | 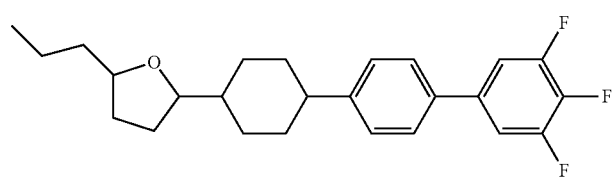 |

| No. | |
|---|---|
| 420 | 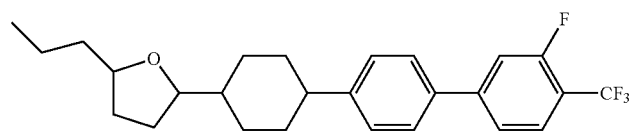 |
| 421 | 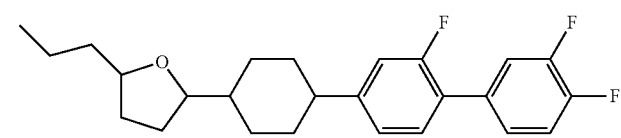 |
| 422 | 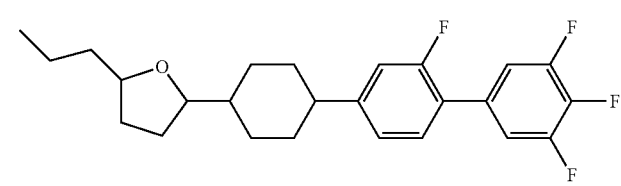 |
| 423 | 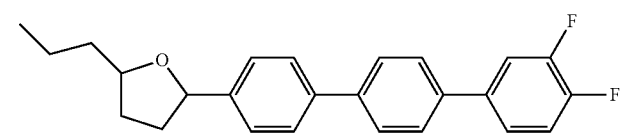 [SMILES: CCCC1CCC(c2ccc(-c3ccc(-c4ccc(F)c(F)c4)cc3)cc2)O1] |
| 424 | 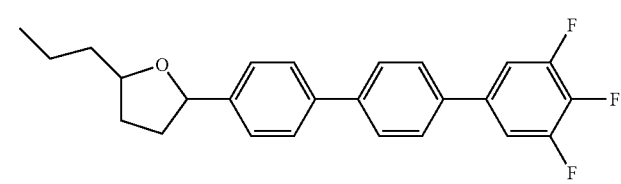 [SMILES: CCCC1CCC(c2ccc(-c3ccc(-c4cc(F)c(F)c(F)c4)cc3)cc2)O1] |
| 425 | 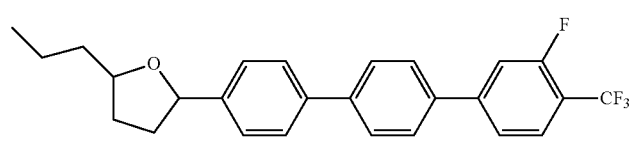 [SMILES: CCCC1CCC(c2ccc(-c3ccc(-c4ccc(C(F)(F)F)c(F)c4)cc3)cc2)O1] |
| 426 | 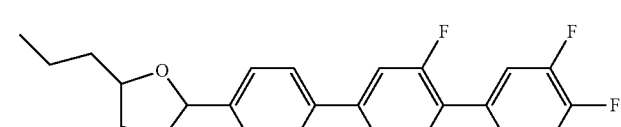 |
| 427 | 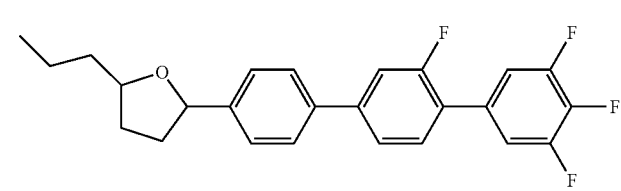 |
| 428 | 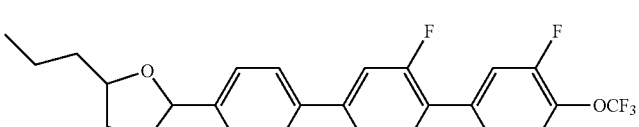 |
| 429 | 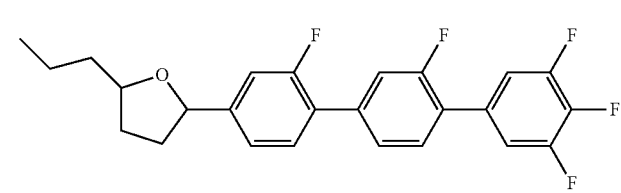 [SMILES: CCCC1CCC(c2ccc(-c3ccc(-c4cc(F)c(F)c(F)c4)c(F)c3)c(F)c2)O1] |

| No. | |
|---|---|
| 430 | 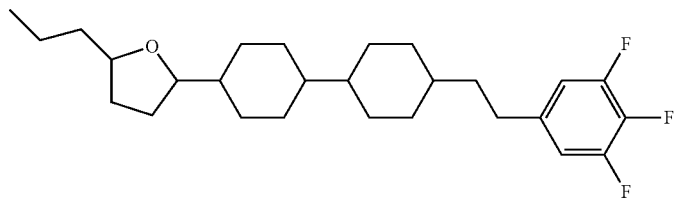 |
| 431 | 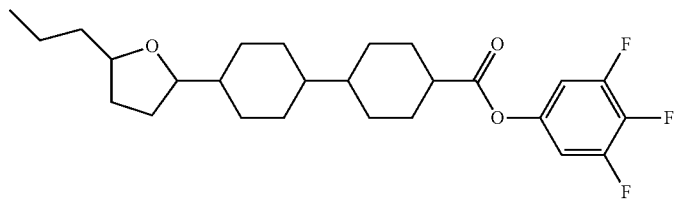 |
| 432 | 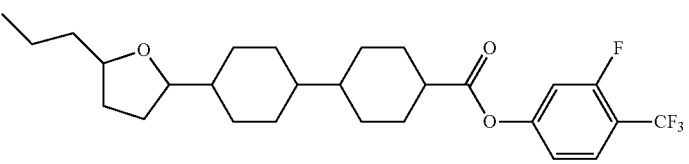 |
| 433 | 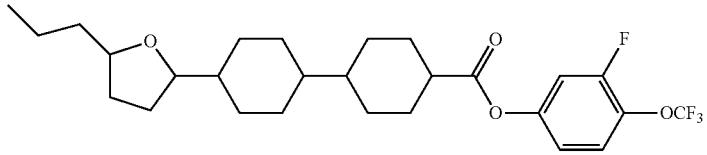 [SMILES: CCCC1CCC(C2CCC(C3CCC(C(=O)Oc4ccc(OC(F)(F)F)c(F)c4)CC3)CC2)O1] |
| 434 | 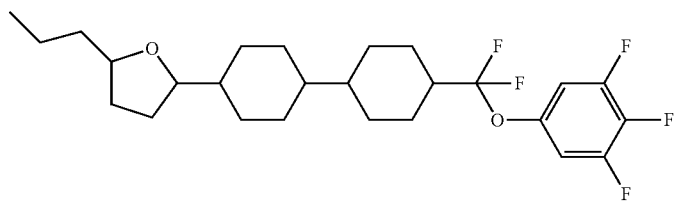 |
| 435 | 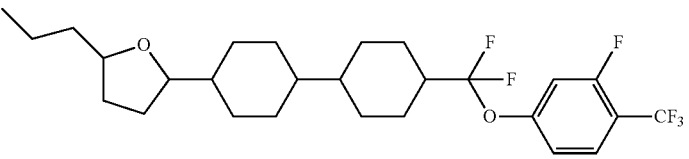 [SMILES: CCCC1CCC(C2CCC(C3CCC(C(F)(F)Oc4ccc(C(F)(F)F)c(F)c4)CC3)CC2)O1] |
| 436 | 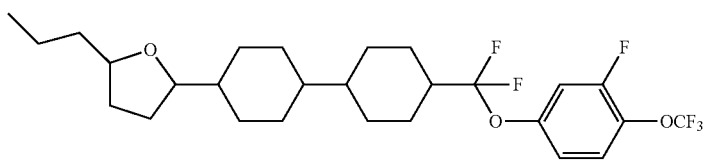 |
| 437 | 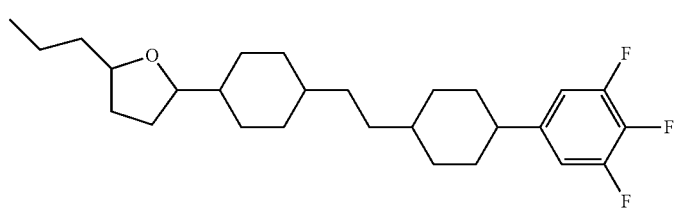 |

| No. | |
|---|---|
| 438 | 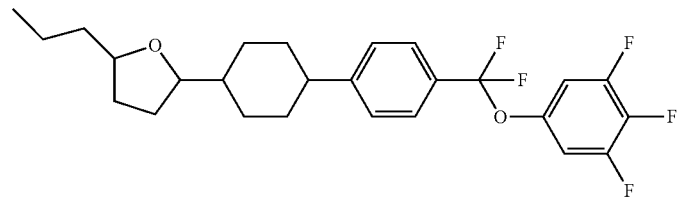 |
| 439 | 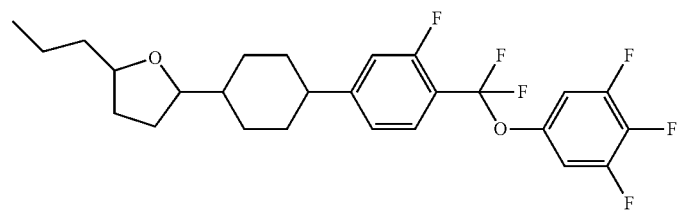 [SMILES: CCCC1CCC(C2CCC(c3ccc(C(F)(F)Oc4cc(F)c(F)c(F)c4)c(F)c3)CC2)O1] |
| 440 | 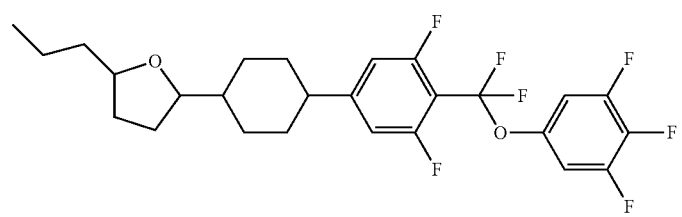 [SMILES: CCCC1CCC(C2CCC(c3cc(F)c(C(F)(F)Oc4cc(F)c(F)c(F)c4)c(F)c3)CC2)O1] |
| 441 | 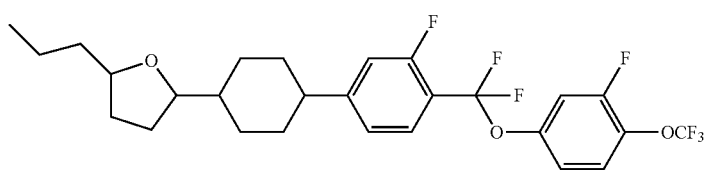 |
| 442 | 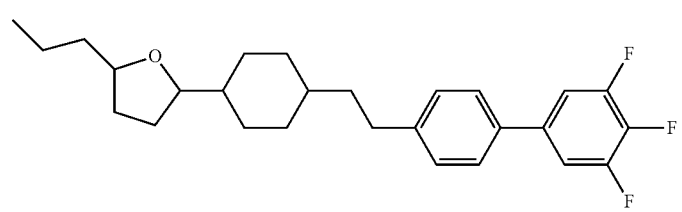 |
| 443 | 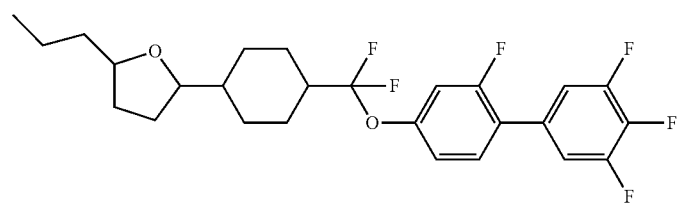 |
| 444 | 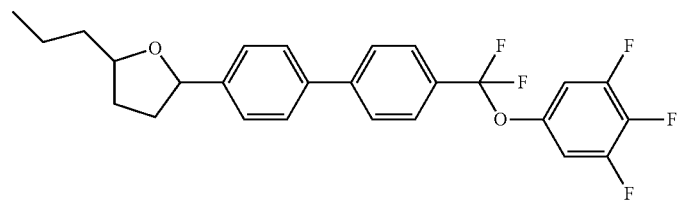 [SMILES: CCCC1CCC(c2ccc(-c3ccc(C(F)(F)Oc4cc(F)c(F)c(F)c4)cc3)cc2)O1] |

| No. |
| --- |
| 445 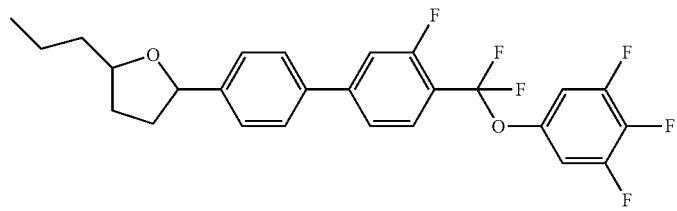 [SMILES: CCCC1CCC(c2ccc(-c3ccc(C(F)(F)Oc4cc(F)c(F)c(F)c4)c(F)c3)cc2)O1] |
| 446 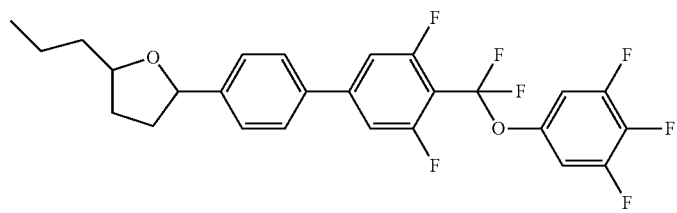 |
| 447 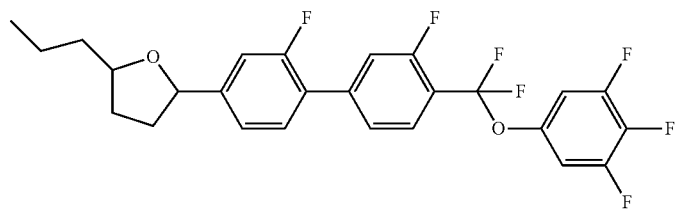 [SMILES: CCCC1CCC(c2ccc(-c3cc(F)c(C(F)(F)Oc4cc(F)c(F)c(F)c4)c(F)c3)cc2)O1] |
| 448 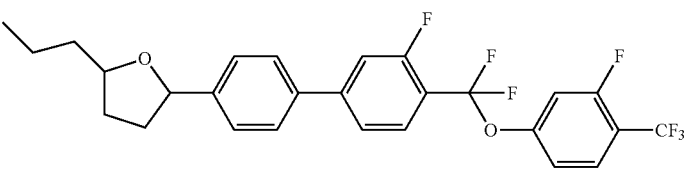 [SMILES: CCCC1CCC(c2ccc(-c3ccc(C(F)(F)Oc4ccc(C(F)(F)F)c(F)c4)c(F)c3)cc2)O1] |
| 449 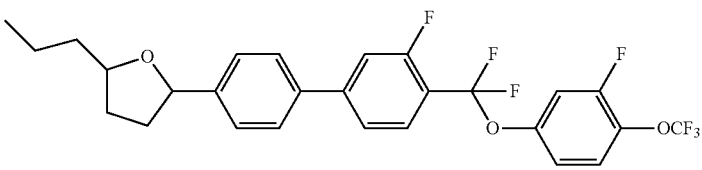 [SMILES: CCCC1CCC(c2ccc(-c3ccc(C(F)(F)Oc4ccc(OC(F)(F)F)c(F)c4)c(F)c3)cc2)O1] |
| 450 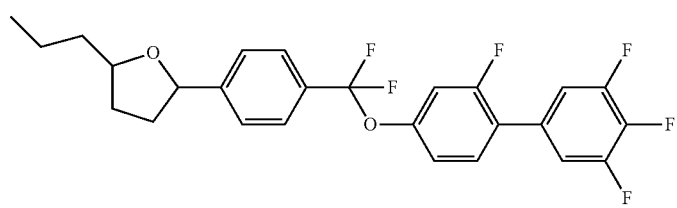 [SMILES: CCCC1CCC(c2ccc(C(F)(F)Oc3ccc(-c4cc(F)c(F)c(F)c4)c(F)c3)cc2)O1] |
| 451 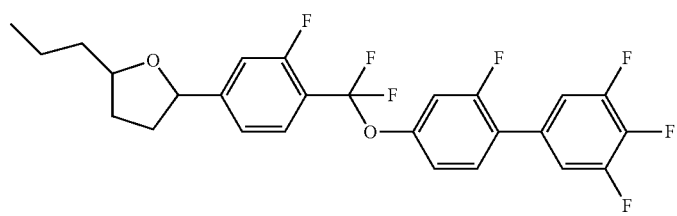 [SMILES: CCCC1CCC(c2ccc(C(F)(F)Oc3ccc(-c4cc(F)c(F)c(F)c4)c(F)c3)c(F)c2)O1] |
| 452 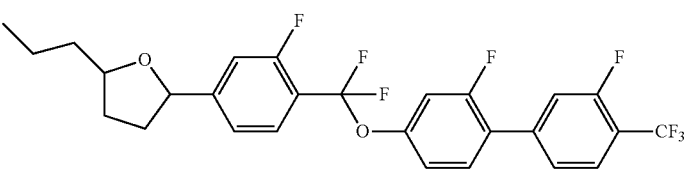 [SMILES: CCCC1CCC(c2ccc(C(F)(F)Oc3ccc(-c4ccc(C(F)(F)F)c(F)c4)c(F)c3)c(F)c2)O1] |

| No. | |
|---|---|
| 453 | 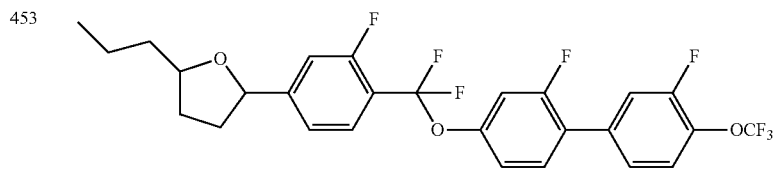 |
| 454 | 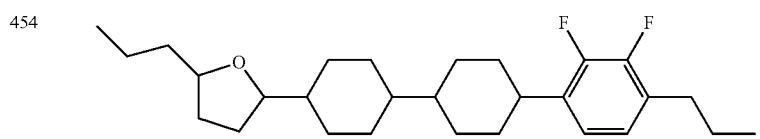 |
| 455 | 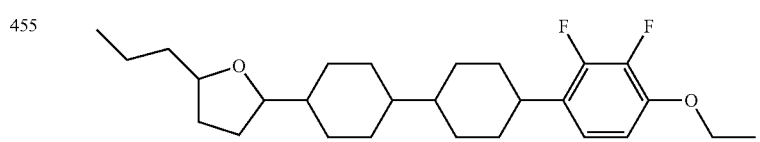 |
| 456 | 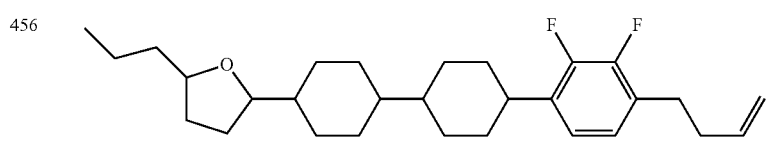 |
| 457 | 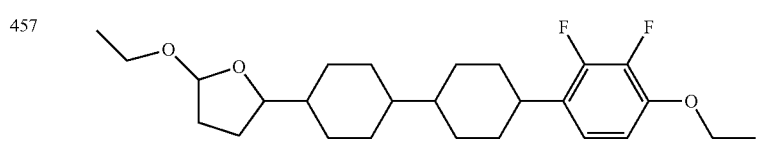 |
| 458 | 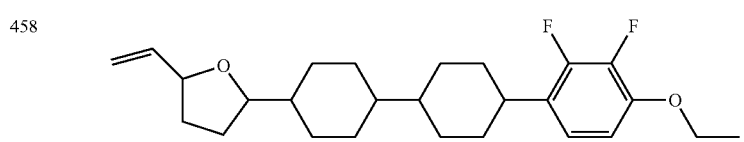 |
| 459 | 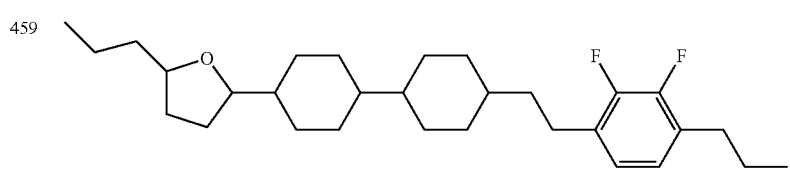 |
| 460 | 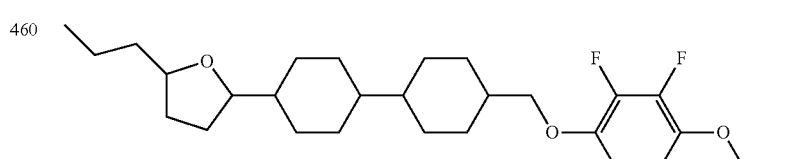 |
| 461 | 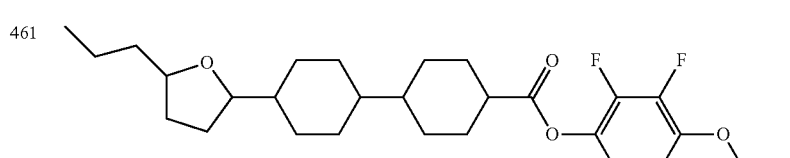 |
| 462 | 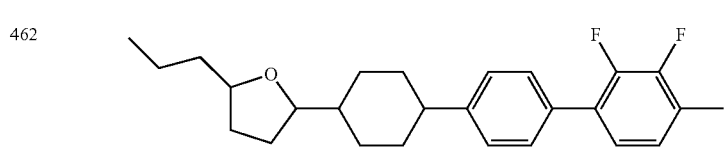 |

| No. | |
|---|---|
| 463 | 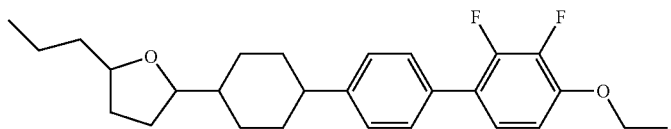 |
| 464 | 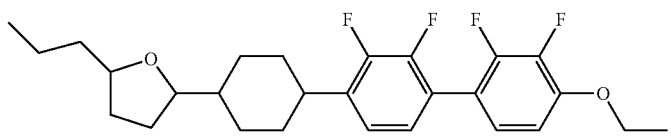 [SMILES: CCCC1CCC(C2CCC(c3ccc(-c4ccc(OCC)c(F)c4F)c(F)c3F)CC2)O1] |
| 465 | 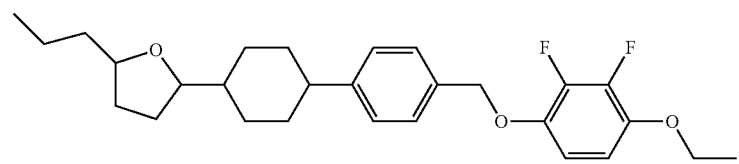 [SMILES: CCCC1CCC(C2CCC(c3ccc(COc4ccc(OCC)c(F)c4F)cc3)CC2)O1] |
| 466 | 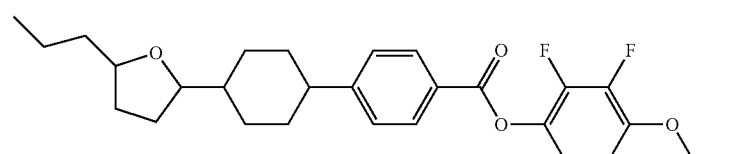 |
| 467 | 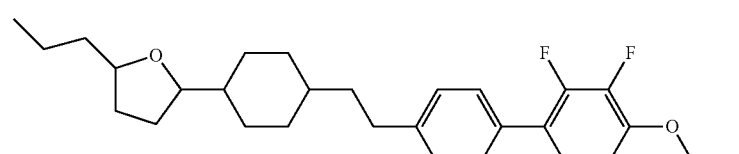 |
| 468 | 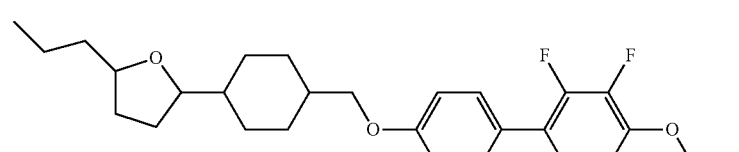 |
| 469 | 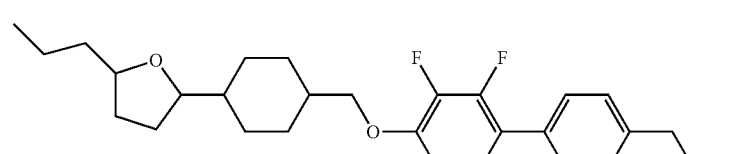 |
| 470 | 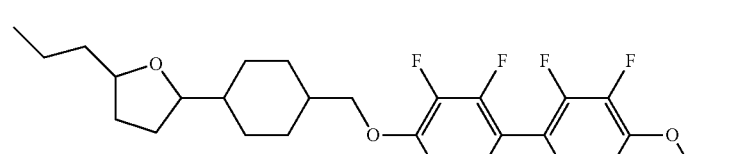 |
| 471 | 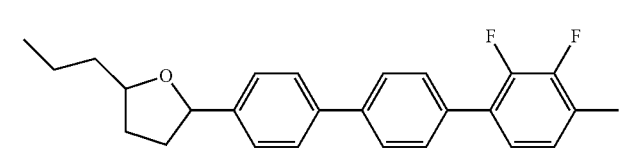 |
| 472 | 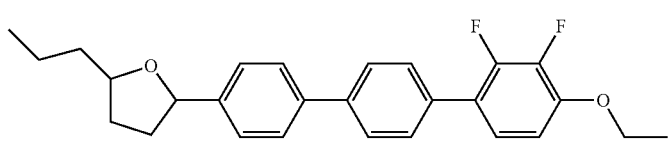 [SMILES: CCCC1CCC(c2ccc(-c3ccc(-c4ccc(OCC)c(F)c4F)cc3)cc2)O1] |

| No. | |
|---|---|
| 473 | 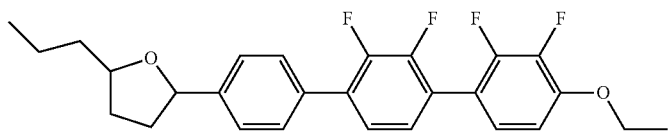 |
| 474 | 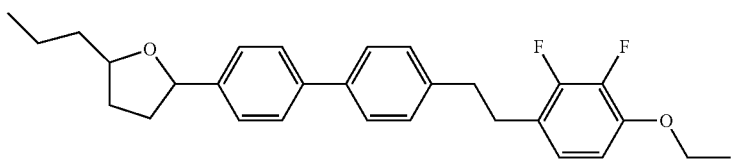 |
| 475 | 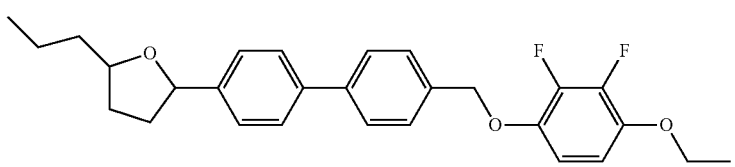 [SMILES: CCCC1CCC(c2ccc(-c3ccc(CCc4ccc(OCC)c(F)c4F)cc3)cc2)O1] |
| 476 | 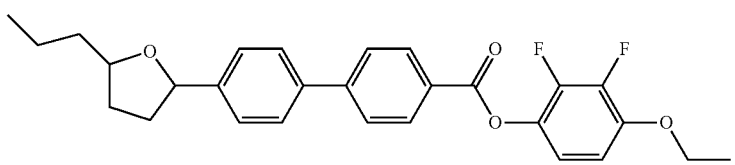 [SMILES: CCCC1CCC(c2ccc(-c3ccc(C(=O)Oc4ccc(OCC)c(F)c4F)cc3)cc2)O1] |
| 477 | 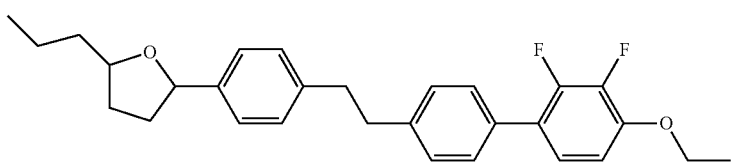 |
| 478 | 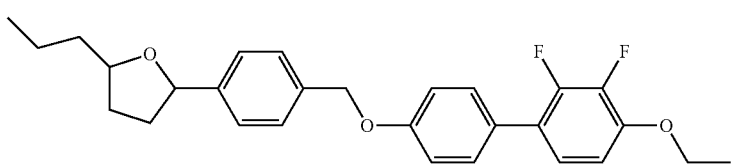 |
| 479 | 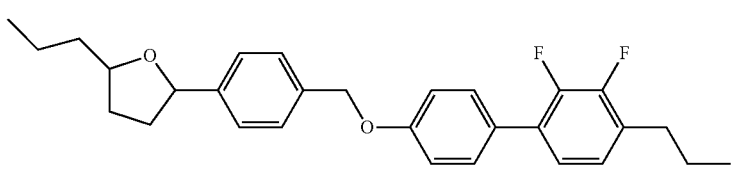 [SMILES: CCCc1ccc(-c2ccc(OCc3ccc(C4CCC(CCC)O4)cc3)cc2)c(F)c1F] |
| 480 | 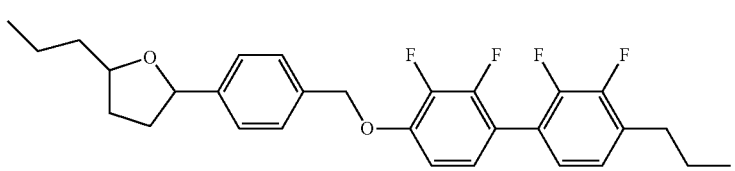 |

Example on the Liquid Crystal Composition

Representative compositions of the invention were summarized in Example 6. First, compounds that are the component of the composition and their ratio (% by weight) are shown. The compounds are expressed as symbols of a left-terminal group, a bonding group, a ring structure and a right-terminal group according to the definition in Table 1.

TABLE 1

Method of Description of Compounds using Symbols
R—(A$_1$)—Z$_1$—Z$_n$ ... Z$_n$—(A$_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2=CH$— | V— |
| $C_nH_{2n+1}$—CH=CH— | nV— |
| $CH_2=CH$—$C_nH_{2n}$— | Vn— |
| $C_mH_{2m+1}$—CH=CH—$C_nH_{2n}$— | mVn— |
| $CF_2=CH$— | VFF— |
| $CF_2=CH$—$C_nH_{2n}$— | VFFn— |

| 2) Right-terminal Group —R' | Symbol |
|---|---|
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | —nV |
| —CH=$CF_2$ | —VFF |
| —$COOCH_3$ | —EMe |
| —CN | —C |
| —F | —F |
| —Cl | —CL |
| —$OCF_3$ | —$OCF_3$ |

| 3) Bonding Group —Z$_n$— | Symbol |
|---|---|
| —$C_nH_{2n}$— | n |
| —COO— | E |
| —OCO— | e |
| —CH=CH— | V |
| —$CH_2O$— | 1O |
| —$CF_2O$— | X |
| —C≡C— | T |

| 4) Ring Structure —A$_n$— | Symbol |
|---|---|
|  | H |
| 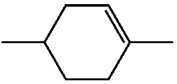 | Ch |
|  | Dh |
|  | dh |
| 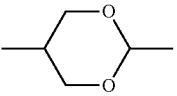 | G |
|  | B |

TABLE 1-continued

Method of Description of Compounds using Symbols
R—(A$_1$)—Z$_1$—Z$_n$ ... Z$_n$—(A$_n$)—R'

| | |
|---|---|
| 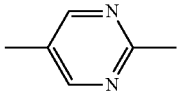 | Py |
| 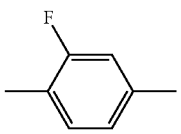 | B(2F) |
| 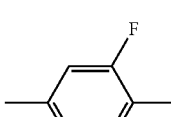 | B(F) |
| 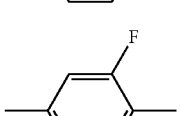 | B(F,F) |
| 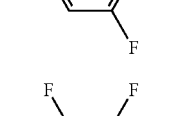 | B(2F,3F) |
| 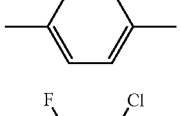 | B(2F,3CL) |
| 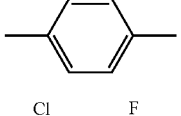 | B(2CL,3F) |
| 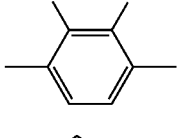 | Cp(3) |
| 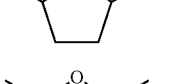 | Thf(2,5) |

5) Examples of Description

Example 1  3-Cp(3)H1OB(2F,3F)—O2

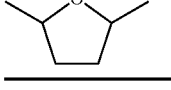

Example 2  3-Thf(2,5)H—V

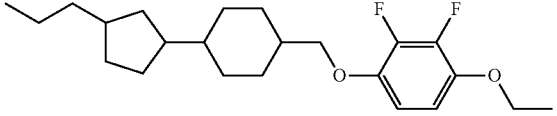 [SMILES: CCCC1CCC(C2CCC(COc3ccc(OCC)c(F)c3F)CC2)C1]

TABLE 1-continued

Method of Description of Compounds using Symbols
R—(A$_1$)—Z$_1$—Z$_n$...Z$_n$—(A$_n$)—R'

Example 3  3-HHB-3

Example 4  3-HHB(F)—F

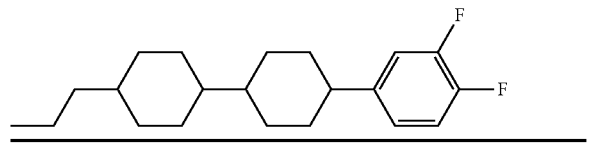

Comparative Example 1

| 3-HB-O1 | (12-5) | 15% |
|---|---|---|
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (13-1) | 6% |

NI = 86.5° C.; Tc < −20° C.; Δn = 0.090; η = 35.3 mPa·s; Δ∈ = −3.4.

Example 1

| 3-Cp(3)H1OB(2F,3F)-O2 | Compound No. 152 | 13% |
|---|---|---|
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 5-HHB(2F,3F)-O2 | (7-1) | 13% |
| 3-HHB-1 | (13-1) | 6% |

NI = 89.3° C.; Tc < −30° C.; Δn = 0.094; η = 41.9 mPa·s; Δ∈ = −3.5.

In the composition of Example 1, "3-HHB(2F,3F)—O2" in the composition of Comparative Example 1 was replaced by the compound No. 152. It was found that the composition in Example 1 is superior to that in Comparative Example 1 in view of a large negative dielectric anisotropy (Δ∈) and a low minimum temperature (Tc).

Example 2

| 3-Cp(3)H-V1 | Compound No. 4 | 5% |
|---|---|---|
| 3-HB-O1 | (12-5) | 15% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (13-1) | 6% |

NI = 89.3° C.; Δn = 0.094; η = 41.9 mPa·s; Δ∈ = −3.5.

In the composition of Example 2, "3-HH-4" in the composition of Comparative Example 1 was replaced by the compound No. 4. It was found that the composition in Example 2 is superior to that in Comparative Example 1 in view of a large negative dielectric anisotropy (Δ∈) and a small viscosity (η).

Example 3

| 4-Cp(3)B(2F,3F)-O2 | Compound No. 45 | 3% |
|---|---|---|
| 4-Cp(3)BB(2F,3F)-O2 | Compound No. 146 | 3% |
| 3-HH-4 | (12-1) | 2% |
| 3-H2B(2F,3F)-O2 | (6-4) | 22% |
| 5-H2B(2F,3F)-O2 | (6-4) | 22% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |
| 5-HHB(2F,3CL)-O2 | (7-12) | 2% |
| 3-HBB(2F,3F)-O2 | (7-7) | 9% |
| 5-HBB(2F,3F)-O2 | (7-7) | 9% |
| V-HHB-1 | (13-1) | 6% |
| 3-HHB-3 | (13-1) | 6% |
| 3-HHEBH-3 | (14-6) | 3% |
| 3-HHEBH-4 | (14-6) | 3% |
| 3-HHEBH-5 | (14-6) | 3% |

NI = 88.4° C.; Δn = 0.100; η = 32.3 mPa·s; Δ∈ = −4.3.

Example 4

| 3-Cp(3)HB(2F,3F)-O2 | Compound No. 140 | 3% |
|---|---|---|
| 3-Thf(2,5)HB(2F,3F)-O2 | Compound No. 377 | 3% |
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 6% |
| 3-HHB(2F,3F)-O2 | (7-1) | 13% |
| 5-HHB(2F,3F)-O2 | (7-1) | 13% |
| 6-HEB(2F,3F)-O2 | (6-6) | 6% |

NI = 73.3° C.; Δn = 0.084; η = 37.3 mPa·s; Δ∈ = −3.8.

The helical pitch was 61.6 micrometers when 0.25 weight parts of the optically active compound (Op-5) was added to 100 weight parts of the preceding composition.

Example 5

| 3-Thf(2,5)HB(2F,3F)-O2 | Compound No. 377 | 3% |
|---|---|---|
| 3-Cp(3)H-V | Compound No. 1 | 3% |
| 2-HH-5 | (12-1) | 3% |
| 3-HH-4 | (12-1) | 15% |
| 3-HH-5 | (12-1) | 4% |
| 3-HB-O2 | (12-5) | 12% |
| 3-H2B(2F,3F)-O2 | (6-4) | 9% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 9% |
| 3-HHB-1 | (13-1) | 3% |
| 3-HHB-3 | (13-1) | 4% |
| 3-HHB-O1 | (13-1) | 3% |

NI = 70.3° C.; Δn = 0.087; η = 19.8 mPa·s; Δ∈ = −4.0.

Example 6

| | | |
|---|---|---|
| 4-Cp(3)BB(2F,3F)-O2 | Compound No. 146 | 3% |
| 3-Thf(2,5)H-V | Compound No. 261 | 3% |
| 3-HB-O1 | (12-5) | 12% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 10% |
| 5-HHB(2F,3F)-O2 | (7-1) | 13% |
| 3-HHB-1 | (13-1) | 6% |

NI = 74.8° C.; Δn = 0.083; η = 35.9 mPa·s; Δ∈ = −3.8.

Example 7

| | | |
|---|---|---|
| 3-Cp(3)HB(2F,3F)-O2 | Compound No. 140 | 3% |
| 3-Cp(3)H-V | Compound No. 1 | 3% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 16% |
| 3-HB-O2 | (12-5) | 10% |
| 3-HH-4 | (12-1) | 3% |
| 3-HHB-F | (3-1) | 3% |
| 3-HHB-1 | (13-1) | 8% |
| 3-HHB-O1 | (13-1) | 4% |
| 3-HBEB-F | (3-37) | 4% |
| 3-HHEB-F | (3-10) | 5% |
| 5-HHEB-F | (3-10) | 3% |
| 3-H2BTB-2 | (13-17) | 4% |
| 3-H2BTB-3 | (13-17) | 4% |
| 3-H2BTB-4 | (13-17) | 4% |
| 3-HB(F)TB-2 | (13-18) | 5% |

NI = 73.1° C.; Δn = 0.134; Δ∈ = 27.6; η = 35.1 mPa·sec.

Example 8

| | | |
|---|---|---|
| 3-Cp(3)H1OB(2F,3F)-O2 | Compound No. 152 | 3% |
| 3-Thf(2,5)H-V | Compound No. 261 | 3% |
| 1V2-BEB(F,F)-C | (5-15) | 6% |
| 3-HB-C | (5-1) | 18% |
| 2-BTB-1 | (12-10) | 10% |
| 5-HH-VFF | (12-1) | 24% |
| 3-HHB-1 | (13-1) | 4% |
| VFF-HHB-1 | (13-1) | 8% |
| VFF2-HHB-1 | (13-1) | 11% |
| 3-H2BTB-2 | (13-17) | 5% |
| 3-H2BTB-3 | (13-17) | 4% |
| 3-H2BTB-4 | (13-17) | 4% |

NI = 72.0° C.; Δn = 0.124; Δ∈ = 5.8; η = 14.4 mPa·sec.

Example 9

| | | |
|---|---|---|
| 4-Cp(3)BB(2F,3F)-O2 | Compound No. 146 | 3% |
| 3-Cp(3)H-V1 | Compound No. 4 | 3% |
| 2-HB-C | (5-1) | 5% |
| 3-HB-C | (5-1) | 12% |
| 3-HB-O2 | (12-5) | 9% |
| 2-BTB-1 | (12-10) | 3% |
| 3-HHB-F | (3-1) | 4% |
| 3-HHB-1 | (13-1) | 8% |
| 3-HHB-O1 | (13-1) | 5% |
| 3-HHB-3 | (13-1) | 14% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

NI = 97.9° C.; Δn = 0.099; Δ∈ = 4.2; η = 19.6 mPa·sec.

Example 10

| | | |
|---|---|---|
| 4-Cp(3)B(2F,3F)-O2 | Compound No. 45 | 2% |
| 4-Cp(3)BB(2F,3F)-O2 | Compound No. 146 | 3% |
| 5-HB-CL | (2-2) | 11% |
| 3-HH-4 | (12-1) | 12% |
| 3-HH-5 | (12-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (14-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 113.6° C.; Δn = 0.091; Δ∈ = 3.3; η = 22.2 mPa·sec.

Example 11

| | | |
|---|---|---|
| 3-Cp(3)H1OB(2F,3F)-O2 | Compound No. 152 | 3% |
| 3-Thf(2,5)HB(2F,3F)-O2 | Compound No. 377 | 3% |
| 5-HB-CL | (2-2) | 3% |
| 7-HB(F)-F | (2-3) | 7% |
| 3-HH-4 | (12-1) | 9% |
| 3-HH-EMe | (12-2) | 23% |
| 3-HHEB-F | (3-10) | 8% |
| 5-HHEB-F | (3-10) | 8% |
| 3-HHEB(F,F)-F | (3-12) | 8% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 3% |

NI = 74.8° C.; Δn = 0.063; Δ∈ = 4.3; η = 20.9 mPa·sec.

INDUSTRIAL APPLICABILITY

The invention provides a new liquid crystal compound having an excellent compatibility with other liquid crystal compositions.

The invention also provides a new liquid crystal composition having the features described above that are desired physical properties, by including this liquid crystal compound as a component and by suitably selecting the ring, the substituent and bonding group that are composing the compound, and further provides a liquid crystal display device containing this liquid crystal composition. The liquid crystal display device can widely be utilized for displays of a computer, a television set and so forth.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A compound represented by formula (1):

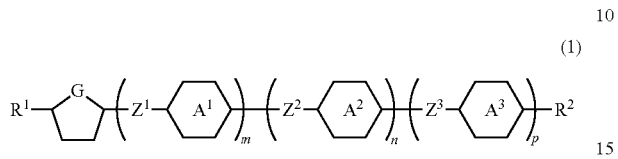

(1)

wherein
R$^1$ and R$^2$ are alkyl having 1 to 10 carbons, and in the alkyl, arbitrary —CH$_2$— may be replaced by —O— and arbitrary —(CH$_2$)$_2$— may be replaced by —CH═CH—;
the ring A$^1$, the ring A$^2$ and the ring A$^3$ are each independently 1,4-cyclohexylene or 1,4-phenylene, and in these rings, arbitrary hydrogen may be replaced by halogen, and at least one of the ring A$^1$, the ring A$^2$ and the ring A$^3$ is 2,3-difluoro-1,4-phenylene;
Z$^1$, Z$^2$ and Z$^3$ are each independently a single bond or alkylene having 1 to 4 carbons, and in the alkylene, arbitrary —CH$_2$— may be replaced by —O— or —CO— and arbitrary —(CH$_2$)$_2$— may be replaced by —CH═CH—, and in these groups, arbitrary hydrogen may be replaced by halogen;
G is —CH; and
m, n and p are each independently 0 or 1, and the sum of m, n and p is 1, 2 or 3.

2. The compound according to claim 1, wherein in formula (1),
R$^1$ is alkyl having 1 to 10 carbons, alkoxy having 1 to 9 carbons or alkenyl having 2 to 10 carbons; R$^2$ is alkyl having 1 to 10 carbons, alkoxy having 1 to 9 carbons, alkenyl having 2 to 10 carbons;
the ring A$^1$, the ring A$^2$ and the ring A$^3$ are each independently 1,4-cyclohexylene, 1,4-phenylene, 2-fluoro-1,4-phenylene, 3-fluoro-1,4-phenylene or 2,3-difluoro-1,4-phenylene and at least one of the ring A$^1$, the ring A$^2$ and the ring A$^3$ is 2,3-difluoro-1,4-phenylene; and
Z$^1$, Z$^2$ and Z$^3$ are each independently a single bond, —(CH$_2$)$_2$—, —(CH$_2$)$_4$—, —COO—, —OCO—, —CF$_2$O—, —OCF$_2$—, —CH═CH—, —CF═CF—, —CH$_2$O— or —OCH$_2$—.

3. The compound according to claim 2, wherein in formula (1),
R$^1$ is alkyl having 1 to 7 carbons, alkoxy having 1 to 6 carbons or alkenyl having 2 to 7 carbons; R$^2$ is alkyl having 1 to 7 carbons, alkoxy having 1 to 6 carbons, alkenyl having 2 to 7 carbons, —CF$_3$, —OCF$_3$, fluorine or chlorine; and
Z$^1$, Z$^2$ and Z$^3$ are each independently a single bond, —(CH$_2$)$_2$—, —COO—, —OCO—, —CF$_2$O—, —OCF$_2$—, —CH$_2$O— or —OCH$_2$—.

4. A liquid crystal composition comprising a first component and a second component, wherein the first component is at least one compound selected from the compounds according to claim 1.

5. The liquid crystal composition according to claim 4, wherein the second component is at least one compound selected from the group of compounds represented by formulas (2), (3) and (4):

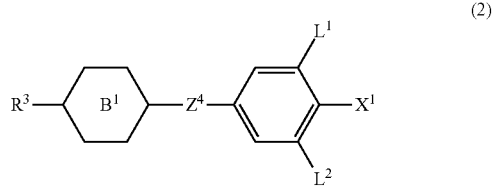

(2)

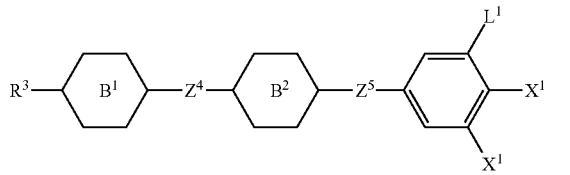

(3)

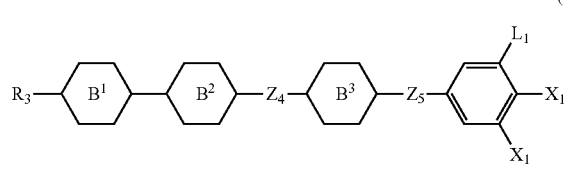

(4)

wherein
R$^3$ is alkyl having 1 to 10 carbons or alkenyl having 2 to 10 carbons, and in the alkyl and the alkenyl, arbitrary hydrogen may be replaced by fluorine and arbitrary —CH$_2$— may be replaced by —O—;
X$^1$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
the ring B$^1$, the ring B$^2$ and the ring B$^3$ are each independently 1,4-cyclohexylene, 1,3-dioxane-2,5-diyl, pyrimidine-2,5-diyl, 1-tetrahydropyran-2,5-diyl, or 1,4-phenylene in which arbitrary hydrogen may be replaced by fluorine;
Z$^4$ and Z$^5$ are each independently —(CH$_2$)$_2$—, —(CH$_2$)$_4$—, —COO—, —CF$_2$O—, —OCF$_2$—, —CH═CH—, —C≡C—, —CH$_2$O— or a single bond; and
L$^1$ and L$^2$ are each independently hydrogen or fluorine.

6. The liquid crystal composition according to claim 4, wherein the second component is at least one compound selected from the group of compounds represented by formula (5):

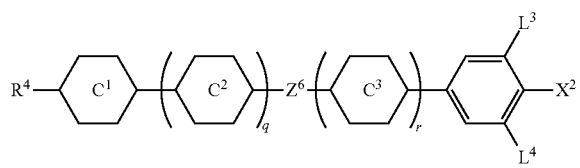

(5)

wherein
R$^4$ is alkyl having 1 to 10 carbons or alkenyl having 2 to 10 carbons, and in the alkyl and the alkenyl, arbitrary hydrogen may be replaced by fluorine and arbitrary —CH$_2$— may be replaced by —O—;
X$^2$ is —C≡N or —C≡C—CN;
the ring C$^1$, the ring C$^2$ and the ring C$^3$ are each independently 1,4-cyclohexylene, 1,4-phenylene in which arbitrary hydrogen may be replaced by fluorine, 1,3-dioxane-2,5-diyl, 1-tetrahydropyran-2,5-diyl or pyrimidine-2,5-diyl;

$Z^6$ is —(CH$_2$)$_2$—, —COO—, —CF$_2$ O—, —OCF$_2$—, —C≡C—, —CH$_2$ O— or a single bond;

L$^3$ and L$^4$ are each independently hydrogen or fluorine; and q is 0, 1 or 2, and r is 0 or 1.

7. The liquid crystal composition according to claim 4, wherein the second component is at least one compound selected from the group of compounds represented by formulas (6), (7), (8), (9), (10) and (11):

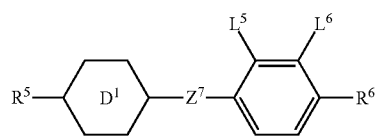
(6)

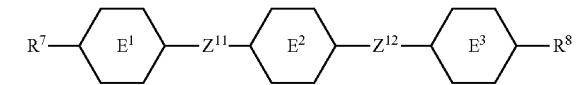
(7)

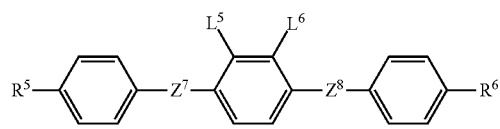
(8)

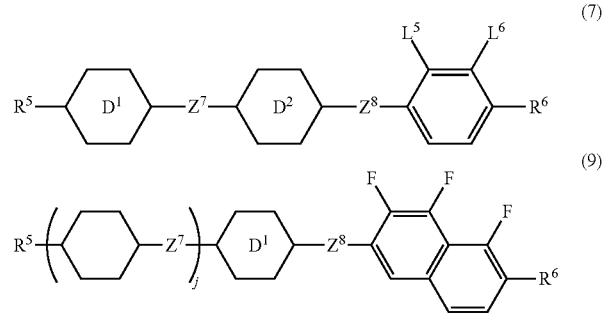
(9)

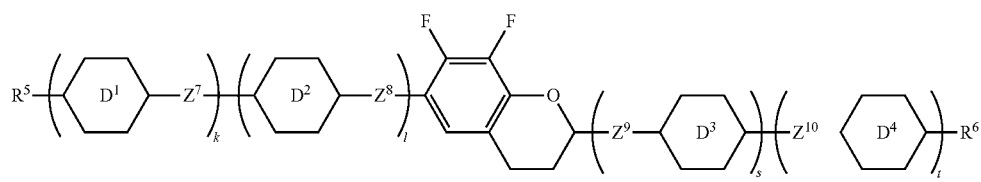
(10)

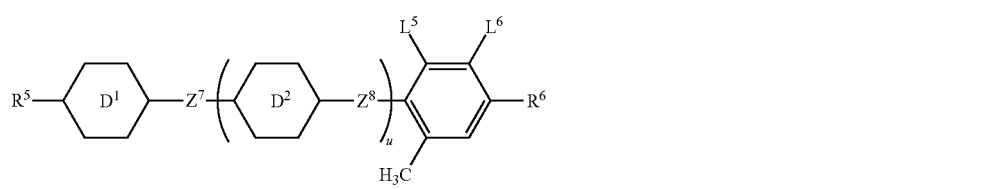
(11)

wherein

R$^5$ and R$^6$ are each independently alkyl having 1 to 10 carbons or alkenyl having 2 to 10 carbons, in the alkyl and the alkenyl, arbitrary —CH$_2$— may be replaced by —O—, and in the alkenyl, arbitrary hydrogen may be replaced by fluorine;

the ring D$^1$, the ring D$^2$, the ring D$^3$ and the ring D$^4$ are each independently 1,4-cyclohexylene, 1,4-cyclohexenylene, 1,4-phenylene in which arbitrary hydrogen may be replaced by fluorine, tetrahydropyran-2,5-diyl or decahydro-2,6-naphthalene;

Z$^7$, Z$^8$, Z$^9$ and Z$^{10}$ are each independently —(CH$_2$)$_2$—, —COO—, —CH$_2$ O—, —OCF$_2$—, —OCF$_2$ (CH$_2$)$_2$— or a single bond;

L$^5$ and L$^6$ are each independently fluorine or chlorine; and j, k, l, s, t and u are each independently 0 or 1, and the sum of k, l, s and t is 1 or 2.

8. The liquid crystal composition according to claim 4, wherein the second component is at least one compound selected from the group of compounds represented by formulas (12), (13) and (14):

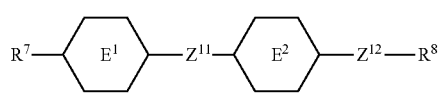
(12)

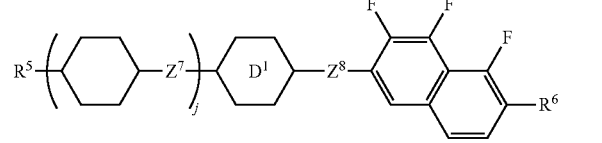
(13)

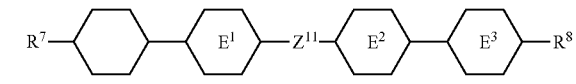
(14)

wherein

R$^7$ and R$^8$ are each independently alkyl having 1 to 10 carbons or alkenyl having 2 to 10 carbons, and in the alkyl and the alkenyl, arbitrary —CH$_2$— may be replaced by —O—, and in the alkenyl, arbitrary hydrogen may be replaced by fluorine;

the ring E$^1$, the ring E$^2$ and the ring E$^3$ are each independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z$^{11}$ and Z$^{12}$ are each independently —C≡C—, —COO—, —(CH$_2$)$_2$—, —CH═CH— or a single bond.

9. The liquid crystal composition according to claim 5, further comprising at least one compound selected from the group of compounds represented by formula (5):

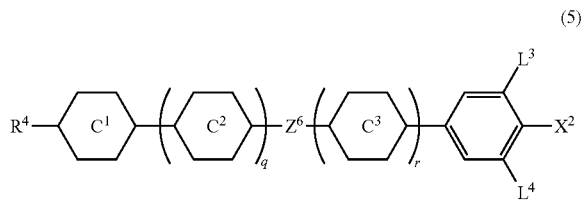
(5)

wherein
R⁴ is alkyl having 1 to 10 carbons or alkenyl having 2 to 10 carbons, and in the alkyl and the alkenyl, arbitrary hydrogen may be replaced by fluorine and arbitrary —CH₂— may be replaced by —O—;

X² is —C≡N or —C≡C—CN;

the ring C¹, the ring C² and the ring C³ are each independently 1,4-cyclohexylene, 1,4-phenylene in which arbitrary hydrogen may be replaced by fluorine, 1,3-dioxane-2,5-diyl, 1-tetrahydropyran-2,5-diyl or pyrimidine-2,5-diyl;

Z⁶ is —(CH₂)₂—, —COO—, —CF₂ O—, —OCF₂—, —C≡C—, —CH₂ O— or a single bond;

L³ and L⁴ are each independently hydrogen or fluorine; and q is 0, 1 or 2, and r is 0 or 1.

10. The liquid crystal composition according to claim 5, further comprising at least one compound selected from the group of compounds represented by formulas (12), (13) and (14):

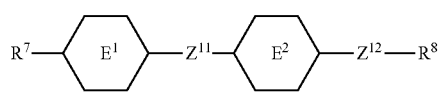
(12)

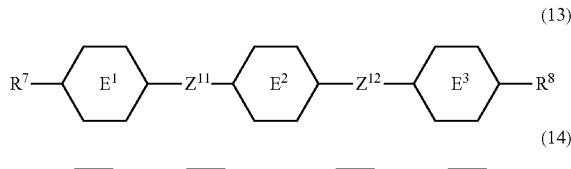
(13)

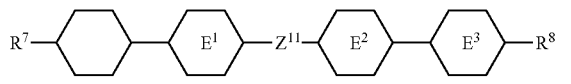
(14)

wherein
R⁷ and R⁸ are each independently alkyl having 1 to 10 carbons or alkenyl having 2 to 10 carbons, and in the alkyl and the alkenyl, arbitrary —CH₂— may be replaced by —O—, and in the alkenyl, arbitrary hydrogen may be replaced by fluorine;

the ring E¹, the ring E² and the ring E³ are each independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z¹¹ and Z¹² are each independently —C≡C—, —COO—, —(CH₂)₂—, —CH=CH— or a single bond.

11. The liquid crystal composition according to claim 6, further comprising at least one compound selected from the group of compounds represented by formulas (12), (13) and (14):

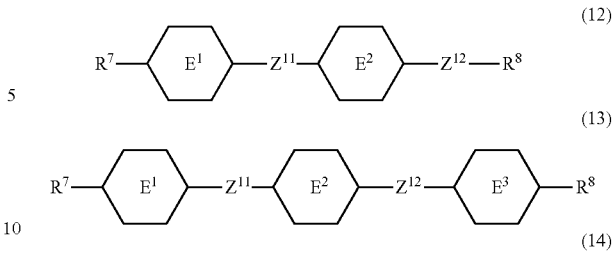
(12)
(13)
(14)

wherein
R⁷ and R⁸ are each independently alkyl having 1 to 10 carbons or alkenyl having 2 to 10 carbons, and in the alkyl and the alkenyl, arbitrary —CH₂— may be replaced by —O—, and in the alkenyl, arbitrary hydrogen may be replaced by fluorine;

the ring E¹, the ring E² and the ring E³ are each independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z¹¹ and Z¹² are each independently —C≡C—, —COO—, —(CH₂)₂—, —CH=CH— or a single bond.

12. The liquid crystal composition according to claim 7, further comprising at least one compound selected from the group of compounds represented by formulas (12), (13) and (14):

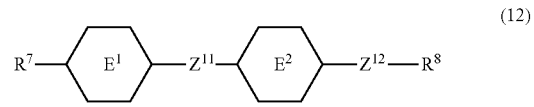
(12)

(13)

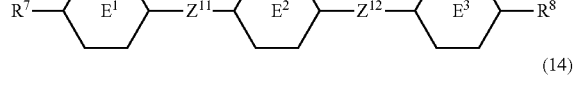
(14)

wherein
R⁷ and R⁸ are each independently alkyl having 1 to 10 carbons or alkenyl having 2 to 10 carbons, and in the alkyl and the alkenyl, arbitrary —CH₂— may be replaced by —O—, and in the alkenyl, arbitrary hydrogen may be replaced by fluorine;

the ring E¹, the ring E² and the ring E³ are each independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z¹¹ and Z¹² are each independently —C≡C—, —COO—, —(CH₂)₂—, —CH=CH— or a single bond.

13. The liquid crystal composition according to claim 4, further comprising at least one optically active compound and/or at least one polymerizable compound.

14. The liquid crystal composition according to claim 4, wherein further comprising at least one antioxidant and/or at least one ultraviolet light absorber.

15. A liquid crystal display device containing the liquid crystal composition according to claim 4.

* * * * *